US010856487B2

(12) United States Patent
Bennett

(10) Patent No.: US 10,856,487 B2
(45) Date of Patent: Dec. 8, 2020

(54) *BRASSICA CARINATA* CULTIVARS AGR044-312D AND AGR044-3A22

(71) Applicant: AGRISOMA BIOSCIENCES INC., Gatineau (CA)

(72) Inventor: Rick Allen Bennett, Saskatoon (CA)

(73) Assignee: NUSEED GLOBAL INNOVATION LTD., Manchester (GB)

( * ) Notice: Subject to any disclaimer, the term of this patent is extended or adjusted under 35 U.S.C. 154(b) by 0 days.

(21) Appl. No.: 16/165,266

(22) Filed: Oct. 19, 2018

(65) Prior Publication Data

US 2019/0045733 A1    Feb. 14, 2019

Related U.S. Application Data

(63) Continuation of application No. PCT/CA2017/050474, filed on Apr. 18, 2017.

(60) Provisional application No. 62/326,111, filed on Apr. 22, 2016.

(51) Int. Cl.
*A01H 5/10* (2018.01)
*A01H 6/20* (2018.01)
*A01H 5/12* (2018.01)

(52) U.S. Cl.
CPC ................. *A01H 6/20* (2018.05); *A01H 5/10* (2013.01); *A01H 5/12* (2013.01)

(58) Field of Classification Search
None
See application file for complete search history.

(56) References Cited

U.S. PATENT DOCUMENTS 7,749,549 B2    7/2010    Lazzeri et al.

OTHER PUBLICATIONS

Alcántara, C., et al. (2011). "Management of cruciferous cover crops by mowing for soil and water conservation in southern Spain." Agricultural Water Management 98(6): 1071-1080.
Babic V, Datla RS, Scoles GJ, Keller WA (1998) Development of an efficient Agrobacterium mediated transformation system for *Brassica carinata*. Plant Cell Rep 17:183-188.
Barro, F. and Martin A., 1999. "Response of different genotypes of *Brassica carinata* to microspore culture." Plant Breeding 118(1): 79-81.
Bevan, M. (1984) Binary Agrobacterium vectors for plant transformation. Nucl. Acids Res. 12, 8711-8721.
Blackshaw, R., et al. (2011). "Alternative oilseed crops for biodiesel feedstock on the Canadian prairies." Canadian Journal of Plant Science 91(5): 889-896.
Bouaid, A., et al. (2005). "Pilot plant studies of biodiesel production using *Brassica carinata* as raw material." Catalysis Today 106(1-4): 193-196.

Cardone, M., et al. (2002). "*Brassica carinata* as an alternative oil crop for the production of biodiesel in Italy: engine performance and regulated and unregulated exhaust emissions." Environ Sci Technol 36(21): 4656-4662.
Cardone, M., et al. (2003). "*Brassica carinata* as an alternative oil crop for the production of biodiesel in Italy: agronomic evaluation, fuel production by transesterification and characterization." Biomass and Bioenergy 25(6): 623-636.
Chan TW, Chishty WA, Canteenwalla P, Buote D, Davison CR. (2015) Characterization of Emissions From the Use of Alternative Aviation Fuels. ASME. J. Eng. Gas Turbines Power. 138(1):011506-011506-9.
Cheng, B., et al. (2009). "Towards the production of high levels of eicosapentaenoic acid in transgenic plants: the effects of different host species, genes and promoters." Transgenic Research 19(2): 221-229.
Datla, R. S., et al. (1992). "Modified binary plant transformation vectors with the wild-type gene encoding NPTII." Gene 122(2): 383-384.
Drenth, A. C., et al. (2014). "Compression ignition engine performance and emission evaluation of industrial oilseed biofuel feedstocks camelina, carinata, and pennycress across three fuel pathways." Fuel 136(0): 143-155.
Drenth, A. C., et al. (2015). "Fuel property quantification of triglyceride blends with an emphasis on industrial oilseeds camelina, carinata, and pennycress." Fuel 153: 19-30.
Fromm, M., et al. (1985). "Expression of genes transferred into monocot and dicot plant cells by electroporation." Proceedings of the National Academy of Sciences of the United States of America 82(17): 5824-5828.
Gasol, C. M., et al. (2009). "Feasibility assessment of poplar bioenergy systems in the Southern Europe." Renewable and Sustainable Energy Reviews 13(4): 801-812.
Gasol, C., et al. (2007). "Life cycle assessment of a *Brassica carinata* bioenergy cropping system in southern Europe." Biomass and Bioenergy 31(8): 543-555.
Gesch, R. W., et al. (2015). "Comparison of several *Brassica* species in the north central U.S. for potential jet fuel feedstock." Industrial Crops and Products 75b: 2-7.
Getinet, A, Rakow, G. and Downey, R.K. 1996. Agronomic performance and seed quality of Ethiopian mustard in Saskatchewan. Can. J. Plant Sci. 76: 387-392.
Getinet, A., Rakow, G. and Downey, R. K. 1987. Seed coat color inheritance in *Brassica carinata* A. Braun, Cultivar S-67. Plant Breed. 99: 80-82.
Gleba, Y., et al. (2004). "Engineering viral expression vectors for plants: the 'full virus' and the 'deconstructed virus' strategies." Curr Opin Plant Biol 7(2): 182-188.
Impallomeni, G., et al. (2011). "Synthesis and characterization of poly(3-hydroxyalkanoates) from *Brassica carinata* oil with high content of erucic acid and from very long chain fatty acids." International Journal of Biological Macromolecules 48(1): 137-145.

(Continued)

*Primary Examiner* — Elizabeth F McElwain
(74) *Attorney, Agent, or Firm* — Harness, Dickey & Pierce, P.L.C.

(57) ABSTRACT

The invention is in the field of *Brassica carinata* breeding (i.e. Ethiopian mustard breeding), specifically relating to the inbred *Brassica carinata* cultivars designated *Brassica carinata* AGR044-312D and *Brassica carinata* AGR044-3A22. The present invention relates to seeds, plants or parts thereof, cells, methods of making, and uses of these cultivars and their progeny. AGR044-312D and AGR044-3A22 may exhibit improved yields relative to existing *Brassica carinata* commercial varieties. Other properties of these cultivars may include reduced levels of seed glucosinolate, improved disease resistance, and reduced tendency to lodging and pod shatter relative to existing commercial *Brassica carinata* varieties.

10 Claims, No Drawings

(56) References Cited

OTHER PUBLICATIONS

Njadhav, A., et al. (2005). "Production of 22:2Δ5,Δ13 and 20:1Δ5 in *Brassica carinata* and soybean breeding lines via introduction of Limnanthes genes." Molecular Breeding 15(2): 157-167.
Johnson, C. M., et al. (1989). "Direct gene transfer via polyethylene glycol." Methods in Cell Science 12(4): 127-133.
Márquez-Lema, A., et al. (2007). Genetic study of very high glucosinolate content in Ethiopian mustard seeds. Proceedings 12th International Rapeseed Congress, Wuhan, China, GCIRC.
Márquez-Lema, A., et al. (2008). "Development and characterisation of a *Brassica carinata* inbred line incorporating genes for low glucosinolate content from *B. juncea*." Euphytica 164(2): 365-375.
Miki, B. L., H. Labbe, J. Hattori, T. Ouellet, G. Sunohara, P. J. Charest, and V. N. Iyer, 1990: Transformation of *Brassica napus* canola cultivars with *Arabidopsis thaliana* acetohydroxyacid synthase genes and analysis of herbicide resistance. Theor. Appl. Genet. 80, 449-458.
Mourato, M. P., et al. (2015). "Effect of Heavy Metals in Plants of the Genus *Brassica*." Int J Mol Sci 16(8): 17975-17998.
Nagaharu, U. 1935. "Genome analysis in *Brassica* with special reference to the experimental formation of *B. napus* and peculiar mode of fertilization." Japanese Journal of Botany 7: 389-452.
Newson, W. R., et al. (2014). "Effect of additives on the tensile performance and protein solubility of industrial oilseed residual based plastics." J Agric Food Chem 62(28): 6707-6715.
Ogura H. (1968) Studies on the new male-sterility in Japanese radish, with special reference to the utilization of this sterility towards the practical raising of hybrid seeds. Mem. Fac. Agric. Kagoshima Univ. 6: 39-78.
Pan, X., et al. (2012). "The effect of cultivar, seeding rate and applied nitrogen on *Brassica carinata* seed yield and quality in contrasting environments." Canadian Journal of Plant Science 92(5): 961-971.
Pane, C., et al. (2013). "Screening of plant-derived antifungal substances useful for the control of seedborne pathogens." Archives of Phytopathology and Plant Protection 46(13): 1533-1539.
Petolino, J. F., et al. (2010). "Zinc finger nuclease-mediated transgene deletion." Plant Molecular Biology 73(6): 617-628.
Prakash, S, Wu, X, Bhat S.R. 2012. History, evolution and domestication of *Brassica* crops. Plant Breed Rev. 35:19-84.
Rahman, M. and Tahir, M. 2010. Inheritance of seed coat color of Ethiopian mustard (*Brassica carinata* A. Braun). Can. J Plant Sci. 90: 279-281.
Rothstein, S. J.; Lahners, K. N.; Lotstein, R. L., et al. (1987) Promoter cassettes, antibiotic-resistance genes, and vectors for plant transformation. Gene 53:153-161.
Sauer, N. J., et al. (2016). "Oligonucleotide-mediated genome editing provides precision and function to engineered nucleases and antibiotics in plants." Plant Physiol.
Schulmeister, T.M. et al (2015) Evaluation of *Brassica carinata* as a Protein Supplement for Growing Beef Heifers. 2015 Florida Beef Research Report 137-142.
Tang, G. and G. Galili (2004). "Using RNAi to improve plant nutritional value: from mechanism to application." Trends Biotechnol 22(9): 463-469.
Taylor, D. C., et al. (2010). "*Brassica carinata*—a new molecular farming platform for delivering bio-industrial oil feedstocks: case studies of genetic modifications to improve very long-chain fatty acid and oil content in seeds." Biofuels, Bioproducts and Biorefining 4(5): 538-561.
Thompson, C, N. R., Movva, R. Tizard, R. Crameri, J. E. Davies, M. Lauwereys,and J. Botterman, 1987: Characterization of the herbicide-resistance gene bar from Streptomyces hygroscopicus. EMBO J. 6, 2519-2523.
Warwick, S. I., Francis, A. and Gugel, R. K. 2009. Guide to wild germplasm *Brassica* and allied crops (Tribe Brassiceae, Brassicaceae). 3rd ed. Agriculture and Agri-Food Canada Research Branch Publication, ECORC, Ottawa. [Online] Available:http://www.brassica.info/info/publications/guide-wild-germplasm.php [Jul. 10, 2013].
Wohlleben, W., W. Arnold, W. Broer, D. Hillemann, E. Strauch, and A. Puhler, 1988: Nucleotide sequence of the phosphotrinocin Nacetyl transferase gene from Streptomyces viridochromogenes Tu494 and its expression in Nicotiana tahacum. Gene 70, 25-37.
Woo, J. W., et al. (2015). "DNA-free genome editing in plants with preassembled CRISPR-Cas9 ribonucleoproteins." Nat Biotechnol 33(11): 1162-1164.
Zanetti, F., et al. (2006). "Can We "Cultivate" Erucic Acid in Southern Europe?" Ital. J. Agron. / Riv. Agron. 1: 3-10.
Zanetti, F., et al. 2013. "Challenges and opportunities for new industrial oilseed crops in EU-27: A review." Industrial Crops and Products 50: 580-595.

BRASSICA CARINATA CULTIVARS AGR044-312D AND AGR044-3A22

CROSS REFERENCE TO RELATED APPLICATION

The present application is a Continuation of International Patent Application No. PCT/CA2017/050474 filed on Apr. 18, 2017 which in turn claims priority from U.S. Provisional Patent Application No. 62/326,211 filed Apr. 22, 2016, the contents of which are incorporated herein by reference in their entirety.

FIELD

The invention is in the field of *Brassica carinata* breeding (i.e. Ethiopian mustard breeding), specifically relating to the inbred *Brassica carinata* cultivar designated *Brassica carinata* AGR044-312D and *Brassica carinata* AGR044-3A22.

BACKGROUND

*Brassica carinata* is a member of the Brassicaceae (formerly Cruciferae) family, commonly known as the mustard family. In Canada, *Brassica carinata* is commonly known as *carinata*, Ethiopian mustard or Abyssinian mustard. It is also referred to as gomenzer (Getinet 1996).

The genus *Brassica* is a member of the tribe Brassiceae in the mustard family (Brassicaceae; Warwick et al. 2009). In addition to *B. carinata*, the *Brassica* genus includes several economically important oilseed crop species: *B. juncea* (L). Czern. (brown mustard), *B. napus* L. (rape, Argentine canola), *B. nigra* (L.) W. D. J. Koch (black mustard), and *B. rapa* L. (field mustard, Polish canola). The genus *Brassica* also includes *B. oleracea* L. food crops, including cabbage, broccoli, cauliflower, Brussels sprouts, kohlrabi and kale.

The six *Brassica* species are closely related genetically, as described in the Triangle of U (U 1935). *Brassica carinata* is an amphidiploid (BBCC, 2n=34) thought to be derived from interspecific hybridization of the diploid species *B. nigra* L. (BB, 2n=16) and *B. oleracea* L. (CC, 2n=18; Prakash et al. 2012). The native range of *Brassica carinata* comprises the central highland region of Ethiopia. All of the naturally occurring *carinata* in these regions is cultivated; there do not appear to be wild populations

*Brassica carinata* is an herbaceous annual with a determinate growth habit (Zanetti et al. 2013). *Carinata* plants have an erect, upright bearing, averaging 1.4 m in height. Plants are highly branching, with well-developed and aggressive tap root systems (Barro and Martin 1999).

Seeds are globose, 1-1.5 mm in diameter and finely reticulated (Mnzava and Schippers 2004). They vary from yellow to yellow-brown to brown in colour (Getinet 1987; Rahman and Tahir 2010). The seeds are rich in oil, containing 37-44% depending on the cultivar and growing conditions, and the seed protein content is high, at 25-30% epressed as seed dry weight (Pan et al, 2012)

In Spain and Italy, seed oil is used for biofuel (Bouaid et al. 2005; Cardone et al. 2002, 2003; Gasol et al. 2007, 2009) and as a bio-industrial feedstock with many uses (i.e., in lubricants, paints, cosmetics, plastics). In North America, *carinata* has been assessed as a biofuel feedstock (Blackshaw et al. 2011), and crude oil produced from *B. carinata* seed has been used for the production of green bio-diesel and bio-jet fuel. In October 2012, experimental aviation flights by the National Research Council of Canada using the world's first 100% bio-jet fuel were successful ("ReadiJet 100% biofuels flight—one of 2012's 25 most important scientific events", Popular Science Magazine, 2012(12).

*Carinata* is grown as a cover crop to reduce soil erosion and herbicide use, and promote water conservation in orchards (Alcantara et al. 2011); it can be plowed into the soil for use as a green manure soil amendment, or as a bio-fumigant (Lazzarini et al; Pane et al. 2013). *Carinata* plants also have utility in heavy metal phytoremediation (Mourato et al 2015). Also, *carinata* seed meal can be used as a high protein animal feed when mixed with other protein sources fed to beef cattle (Schulmeister et al, 2015)

(A) *Brassica carinata* Breeding

*Carinata* breeding has focused on the improvement of seed quality traits, agronomic performance (e.g., early maturity, higher yield) and disease resistance. *Carinata* varieties optimized for production of feedstock for biofuels (i.e. biodiesel, bio-jet fuel), bio-industrial uses such as for manufacturing of bio-plastics (Newson et al, 2014, Impallomeni et al. 2011), lubricants (Zannetti et al; 2006) and specialty fatty acids such as 5, 13-docosadienoic acid, 5-eicosenoic acid (Jadhav et al. 2005), eicosapentaenoic acid (Cheng et al. 2009) and nervonic acid (Taylor et al 2010) have been developed. In some cases, modification of the seed oil profile has involved the use of transgenic technologies to introduce specific genes encoding enzymes of the fatty acid biosynthesis pathways (Taylor 2010).

Breeding to improve *carinata* seed quality has led to development of lines with lower meal glucosinolate content with potential for use as a protein rich additive for additive in animal diets (Xin and Yu 2014; Getinet et al. 1997; Márquez-Lema et al. 2006, 2008). *Carinata* bred for very high levels of glucosinolates in seed meal is of use in biofumigation (Márquez-Lema et al. 2009).

Critical to the development and breeding of any crop is the ability to make use of genetic and phenotypic diversity. For a newly developing crop such as *carinata*, it is necessary to be able to obtain a sufficient pool of genetic material to identify genetic backgrounds more adapted to target geographies (i.e. a better starting point), as well as variation for traits of interest. This allows for crossing or other modifications to be done, to identify genetic combinations superior to the types already tested. Thus, an important initial objective is the collection and characterization of as large of a collection of genetic backgrounds as possible, for each target geography.

Characterization of accessions or breeding lines of *carinata* generally takes place in the field in the geography of interest, where phenotypic data collected is generally more reflective of actual performance that would be realized by a seed producer. Traits collected focus on those that would be of agronomic or economic benefit in the crop. Examples of traits characterized in a *carinata* breeding program are early plant vigor, plant height, branching habit, days to flower, silique density, flower petal color, pod size, reaction to heat and water stress, disease susceptibility, shatter tolerance, etc.

Breeding nurseries are often the first cycle of evaluation of new material, whether from sources external to the breeding program, or new genetic combinations generated within the breeding program. Generally, nurseries utilize single or paired rows with frequent checks (i.e. the best available commercial germplasm for a specified geography), to evaluate overall agronomic potential as well as specific traits of the experimental material. For material that is somewhat heterogeneous but displays traits of interest, often multiple single plants will be self-pollinated, and carried forward to the next breeding cycle. In this way, multiple streams of inbred parents are in simultaneous development each year. These inbred lines can be yield tested to become an open-pollinated (OP) variety if sufficiently improving on the checks; however, the more usual scenario is they are used as parents in crossing or as parents in hybrid testing. When inbred lines are developed in this way as a result of a planned cross, this is referred to as pedigree breeding. In the case that they are developed from a collection or accession, it is usually referred to as inbred line development. Self-pollination is also done in completely inbred lines to preserve a pure seed supply of those lines that may warrant further testing.

Crossing of inbred lines, by sexual hybridization, is typically done manually in controlled conditions. The selection of parents of these crosses is critical to the effectiveness of a breeding program. Parental lines are selected based on breeding priorities and the unique combination of traits available in potential crossing parents. Often, two or three rounds of crossing are needed to accumulate beneficial alleles into a single genetic background. This includes evaluating offspring of a cross, selecting the most desirable inbred lines as future parents, and making the next round of parental selection based on priority targets.

Doubled Haploid (DH) Technology:

DH technology allows for the generation of completely homozygous lines, which are a combination of genes of the parental lines, in a single generation. This accelerates the process of inbred line development dramatically; as the process from seeding of parental lines to obtaining seed for a resulting inbred population from those parents will generally take about 18 months. To achieve a highly homozygous line using traditional self-pollination generally will take five or six growth cycles; which in the case of *carinata* would represent three years or six growth cycles, with two cycles completed per year. In this technique, using appropriate in vitro conditions, haploid microspores from an F1 plant can be induced to differentiate into diploid embryos and subsequently plantlets. This technique typically relies on a percentage of regenerated plants to undergo spontaneous doubling (usually in the range of 20 to 60% of plants, depending on a number of factors), whereas the remaining plants will remain haploid and sterile. To increase the efficiency of space used for seed increase, such as in the greenhouse or field, a flow cytometer is used to distinguish at an early stage the chromosome content "n" or "2n" of each plant. Thus, the sterile plants can be discarded at an early stage.

Molecular Markers:

A breeding program can make use of marker assisted breeding (MAB) to accelerate the successful outcome of a breeding project. This allows the identification of lines carrying a trait of interest in the laboratory, while other lines not containing a marker of interest can then be discarded at an early stage. This increases the efficiency of a program, as the lines being evaluated in the field have a greater probability of meeting seed quality or other criteria. MAB relies on the existence of a dense set of genetic markers for the species of interest. Genetic markers are the unique sequences that may be found in allelic forms of genes, distinguishing one allele from another. Like genes themselves they can be transmitted to progeny in a Mendelian fashion and can thus be used to follow the movement of specific alleles from parents to progeny. There are several types of genetic markers in common use, including:

i. Restriction fragment length polymorphisms (RFLP): where a mutation may create or eliminate a restriction site, creating restriction fragments of unique size. These are detected by electrophoresis and transfer onto membranes (Southern blotting) followed by hybridization with specific labeled probes;

ii. Random Amplified Polymorphic DNA (RAPD): where a single primer is used to PCR amplify random segments of genomic DNA, sequence polymorphisms which diminish the primers ability to hybridize at a locus will cause the disappearance of specific bands, polymorphisms which result in improved hybridization can result in new amplified bands;

iii. Amplified Fragment Length Polymorphism (AFLP): where genomic DNA is digested with a pair of restriction enzymes, one rare cutting and the other frequent cutting. Fragments are then annealed to synthetic adaptors and then PCR carried out using primers complementary to the adaptor sequence and adjacent restriction sites. The PCR products can be separated by gel or capillary electrophoresis and the pattern of bands produced constitutes a unique fingerprint for a particular genotype;

iv. Simple Sequence Repeats (SSRs): repeat sequences called microsatellites (from 2 nt to 6 nt in length) are found randomly distributed in plant genomes. The copy numbers of these repeats at their sites of occurrence can vary greatly and constitutes a source of considerable allelic polymorphism. Primers homologous with regions that flank known microsatellite-containing regions are used to amplify the genomic DNA and the variation in size of the polymorphic products can be used to demonstrate the local allelic variations;

v. Single Nucleotide Polymorphism (SNP): are single base changes, deletions or insertions that can occur in coding noncoding or intergenic DNA. These can be detected in a number of ways, for example by NGS sequencing, differential hybridization etc.

The most useful markers are those that are co-dominant—they allow a researcher to distinguish whether the plant is homozygous, heterozygous or null for a particular marker. The utility of a marker is also increased if it can be detected using very little DNA and if the methodology of detection is relatively simple, sensitive and reproducible. Allelic markers are also more valuable if their presence is linked to the expression of a particular phenotypic trait and molecular markers that co-segregated with alleles that are linked to quantitative trait loci (QTL) afford the opportunity to use these markers in marker assisted breeding.

Wide Crossing (Interspecific Crossing):

In some instances, a trait may not reside within the species of interest. In that case, it may be possible to transfer the trait via interspecific or wide crossing. The methodology for performing the cross is similar to that described for within-species crosses described above. However, unlike intraspecific crosses, the likelihood of the cross producing viable seed is very low and thus represents a formidable challenge to the success of this technique. In order to overcome this potential block, embryo rescue techniques are often employed to recover viable offspring from the cross. Essentially this relies on the progeny surviving until the embryogenic stage at which point it can be dissected from the silique and placed into artificial growth medium. Under appropriate conditions the cultured embryo can survive and be induced to differentiate into a plantlet, which can be grown into a mature plant. Successive rounds of embryo rescue may be needed until inbred progeny, or backcross-derived progeny, are stable and can produce fertile offspring without intervention. Often molecular markers, where available, are used to trace a specific allele from a related species into an adapted background in the target species, using repeated cycles of backcrossing.

Hybrid Cultivar Testing:

*Brassica* species have been shown to display significant levels of heterosis, or hybrid vigor. Most of the *B. napus* varieties available today are hybrid varieties. It is very probable that similar levels of heterosis for seed yield and vigorous plant development can be exploited in *B. carinata*. This breeding technique may allow the crop to achieve yield potentials, which would allow the resulting biofuels to be more price competitive with traditional petroleum. However, not much research has been done to date on testing hybrid combinations of *carinata*. Thus, there may be a large forum for exploiting heterosis in this crop and increasing productivity on farm, as well as profitability to producers.

In order to produce and test hybrid combinations, some form of pollination control system must be employed. The most widely used pollination control system to achieve this in *Brassica* species is the method of Ogura (1968) based on male cytoplasmic sterility. In cytoplasmic male sterile (cms) plants, a mitochondrial gene mutation interferes with the flowers ability to produce viable pollen but does not affect the functionality of the flower's female components. Because the mutation is within the mitochondrial genome, it is transmitted maternally through the cytoplasm. The Ogura cms trait is derived from a Japanese radish variety and has been successfully transferred to *Brassica juncea* and *B. napus* through interspecific crossing. While the mitochondrial gene mutation eliminates the ability of the cms variety to self-pollinate, it does not interfere with its ability to outcross via pollination from non-cms varieties and thus produce $F_1$ seed. However, the resulting hybrid $F_1$ produced in such a cross would be male sterile, as this trait is maternally transmitted. The cms phenotype in the $F_1$ can be overcome by the expression of a nuclear genome encoded restorer (Rf) gene in the male variety used in the cross to produce the $F_1$. The nuclear Rf gene of radish has also been successfully introgressed in *Brassica napus* (ref) and *Brassica juncea* (ref) varieties. More recently, both the CMS and Rf traits have been developed and are being validated in *B. carinata*. The development of a set of genetically diverse cms and Rf lines in *carinata* will allow the testing of a large number of combinations for the first time in this *Brassica* species.

In a hypothetical production scheme based on the Ogura CMS system the following steps are carried out:

i. Based on genetic diversity and groupings, key morphological traits, and agronomic potential, female (A-lines) carrying the cms trait, and male (R-lines) carrying the restorer gene, are developed;

ii. Test hybrids are produced and evaluated typically in replicated small plot trials, for evaluation of yield potential and other characteristics;

iii. Patterns of heterosis between parental "pools" are identified, combinations using these pools are tested more extensively;

iv. Specific combinations are also selected for potential commercial release as a new variety;

v. Parental seed is increased for commercial production scheme of best hybrid variety. In order to do so, a maintainer (B-line) of the cms parent is also necessary for seed increase.

Mutagenesis:

Another method of creating genetic variation, and capturing beneficial changes in a heritable fashion, is through mutagenesis breeding. This method is often carried out via chemical means or ionizing radiation, and is typically focused either on a microspore or on a whole seed level. In *Brassica* breeding, some common forms of mutagens used have been chemical agents such as Ethyl methanesulfonate (EMS) or N-ethyl-N-nitrosourea (ENU), high levels of ionizing (x-ray or gamma) irrradiation or exposure to UV light. EMS produces random point mutations via low frequency methylation of guanine residues in genomic DNA. This results in altered Watson-Crick base pairing such that the affected base pairing is converted from G-C to A-T. ENU is also an alkylating agent that preferentially modifies thymine residues converting A-T to G-C. Ionizing radiation may affect DNA in many ways but more often than not the mutations are double strand breaks leading to deletions and frameshift mutations that are frequently inactivating.

To carry out this technique, seedlings or microspores are exposed to the mutagenic agent and the surviving fraction are allowed to develop into mature plants. In some cases, the mutagenized plantlets or embryos (in the case of microspore mutagenesis) may be exposed to selection in order to enrich for a particular phenotype. For example, mutagenesis has been used to develop plants that are resistant to the actions of specific herbicides; in this instance the developing plantlets or microspores can be grown in vitro in the presence of the herbicide(s) of interest in order to select for those plants with the appropriate mutations conferring resistance. The advantage of the microspore mutagenesis of the seed approach is that the resultant DH plants can be used to derive pure and homozygous plant lines, where all induced mutations, whether dominant or recessive, would be expressed. Mutagenesis has been used to develop *brassica* varieties with resistance to various herbicides, altered seed oil profiles and increased tolerance to disease and abiotic stress.

Genetic Transformation: In instances where unique and valuable traits are known to be available in distant plant or in non-plant species that cannot be transferred to *Brassica carinata* via classical breeding, and where the genes for those traits have been cloned, a breeding program may resort to genetic transformation techniques to stably transfer those genes into this species. Transfer of cloned genetic elements into *B. carinata* have been achieved via a number of means, including PEG mediated DNA uptake into protoplasts (Johnson, C M. et al. 1989), electroporation into protoplasts (Fromm, M et al 1985), ballistic infiltration using DNA coated microprojectiles (Finer, J. et al 1999), *Agrobacterium*-based vector infiltration (Babic et al, 1997), infection using plant virus based vectors (Gleba et al 2014). Aside from having the genes of interest in cloned form, the other requirements include having the genes cloned into a suitable vector to allow for their propagation in an appropriate bacterial system as well as their packaging, in appropriate viral and agrobacterial strains to allow for their infectious route of transfer. Once transferred they would also require appropriate plant based promoters, enhancers and terminators to allow for the correct temporal and tissue specific pattern of expression for the heterologous gene. Finally, in order to select those rare events where the heterologous gene expression unit has been successfully transferred into the plant genome, a selectable marker may be introduced, either physically linked to the heterologous gene of interest or co-transformed with the gene of interest at a suitable ratio so as to favor co-insertion.

The selectable marker may consist of a gene that can confer resistance to a particular herbicide or antibiotic that would otherwise kill the plant, or a gene that may confer a growth advantage, a gene that may alter a response to plant hormones, or may express a fluorescent protein that can allow transformed cells to be easily visualized. Examples of selectable markers based on conferring resistance to antibiotics, successfully used in *brassica* transformation are the NPTII gene (Bevan, 1984; Datla et al, 1992, encoding an enzyme conferring resistance to the antibiotic kanamycin and the HPT gene encoding an enzyme conferring resistance to the antibiotic Hygromycin (Rothstein et al, 1987). Examples of selection markers based on conferring tolerance to herbicides and successfully used in *brassica* transformation are the BAR (Thompson et al, 1987) and PAT (Wohlleben et al, 1988) gene products which confer resistance to glufosinate (bialaphos) or L-PPT and the AHAS gene product conferring resistance to imidazolinones (Miki et al. 1990). Other plant selectable markers have been developed whose actions are not based on conferring resistance to toxic compounds per se but instead allow survival in the presence of nutrients not normally metabolized by the wildtype organism.

Transformation cannot only be used to introduce heterologous genes into the genome of *carinata* plants, it can also be used to introduce DNA constructs that are designed to modulate the expression of endogenous genes. Genes encoding antisense RNA or RNAI sequences (Tang and Galil, 2004) can be used to interfere or knock down the expression of endogenous genes to extremely low levels, simulating the effect of a null mutation at the endogenous locus. This of course relies on the continuous stable expression of the antisense or RNAi to be effective. In amphidiploid *brassica* species such as *napus, juncea* and *carinata* multiple copies of genes from the contributing ancestral species may create a high level of functional redundancy such that a single mutation in one of the homologues may not be sufficient to confer a phenotype. However, by using an RNAi or antisense approach, where the interfering RNA is derived from conserved sequences, one may conceivably be capable of targeting all of the expressed homologues and achieving a functional knockdown effect.

More recently several novel approaches have been developed which offer the ability to manipulate the plant genome in a targeted way. Collectively known as gene editing technology, (Petolino et al, 2010; Sauer et al 2014, Woo et al, 2015) the technologies share several important similarities:

i. They offer the ability to introduce small or large gene deletions in the plant genome by means of targeted double strand breaks at precise genomic locations
ii. They allow for the insertion of small inactivating mutations into specific genes of interest
iii. They permit the replacement of an entire gene or gene segment by a modified counterpart
iv. They allow for the insertion of a heterologous gene in a specific genomic location which may represent a preferred site for regulated gene expression. (i.e. downstream of a known endogenous promoter/enhancer)

As is evident by the examples cited and to those skilled in the art, there are numerous methods available to the *carinata* breeder to assemble a unique collection of traits into a singular cultivar. The skill lies in the ability of the breeder to select for the combination of traits through successive generations, and ultimately obtaining a unique, homogeneous and homozygous cultivar breeding true for the selected combination of traits, a necessary requirement for commercial crop production.

SUMMARY

According to the present invention, there are provided novel *Brassica carinata* varieties designated *Brassica carinata* AGR044-312D and AGR044-3A22. This invention thus relates to the seeds of the AGR044-312D and AGR044-3A22 varieties, to plants of the AGR044-312D and AGR044-3A22 varieties, methods for producing a *Brassica carinata* plant produced by self-crossing of AGR044-312D or AGR044-3A22 or outcrossing said varieties with other *Brassica carinata* lines as well as producing DH varieties from F1 of said crosses, methods for producing a *Brassica carinata* plant by outcrossing the AGR044-312D and AGR044-3A22 with other *brassica* species, such as *Brassica napus, Brassica juncea, Brassica oleracea, Brassica rapa, Brassica nigra*, followed by backcrossing with AGR044-312D and AGR044-3A22 as well as producing DH varieties from said interspecific crosses. The invention also relates to the use of the AGR044-312D and AGR044-3A22 varieties as a background for chemical and/or radiation induced mutagenesis or for targeted gene editing, for modulation of traits via RNA interference or antisense RNA expression or for introduction of traits via genetic transformation. The invention may also encompass the use of the AGR044-312D and AGR044-3A22 line in a hybrid variety production scheme as described above.

In the embodiments described below, "essentially all of the physiological and morphological characteristics" can mean, for example, the quantitative physiological and morphological characteristics described in Tables 1 and 3-7 for AGR044-3A22 or in Tables 1, 2, and 4-14 for AGR044-312D when grown in the same location under the same environmental conditions, as determined at the 5% significance level.

In the embodiments described below, "essentially all of the physiological and morphological characteristics" can also mean the quantitative physiological and morphological characteristics described in Tables 1, 3 and 5-7 for AGR044-3A22 or in Tables 1, 2, 5-10, and 12-14 for AGR044-312D when grown in the same location under the same environmental conditions, as determined at the 5% significance level.

In particular embodiments, there is provided:

1. A seed of *Brassica carinata* cultivar designated AGR044-312D, wherein a representative sample of the seed has been deposited under ATCC Accession number PTA-123015.
2. A plant of *Brassica carinata* cultivar AGR044-312D, or a part thereof, produced from the seed of embodiment 1.
3. The plant part of embodiment 2, wherein the plant part is an ovule, a leaf, pollen, a seed, an embryo a root, a root tip, a pod, a flower, a stalk, a cell, or a protoplast.
4. The plant part of embodiment 3, wherein the plant part is pollen.
5. The plant part of embodiment 3, wherein the plant part is an ovule.
6. A *Brassica carinata* plant, or parts thereof, having essentially all of the physiological and morphological characteristics of the plant of embodiment 2 when grown in the same location under the same environmental conditions.
7. A tissue culture of protoplasts or regenerable cells of the plant, or part thereof, of embodiment 2.
8. The tissue culture according to embodiment 7, wherein the protoplasts or regenerable cells are produced from a tissue selected from the group consisting of leaves, pollen, embryos, roots, root tips, pods, flowers, ovules, and stalks.
9. A *Brassica carinata* plant regenerated from the tissue culture of embodiment 7 or 8, wherein the plant has essentially all of the morphological and physiological characteristics of cultivar AGR044-312D, the seed of which has been deposited under ATCC Accession number PTA-123015, when grown in the same location under the same environmental conditions.
10. A regenerated *Brassica carinata* plant having essentially all of the physiological and morphological characteristics of the cultivar AGR044-312D when grown in the same location under the same environmental conditions, the regenerated plant having been produced using a tissue culture, wherein the tissue culture is produced from the plant or part thereof of embodiment 2.
11. A method for producing *Brassica carinata* seed comprising crossing *Brassica carinata* plants and harvesting the resulting *Brassica carinata* seed, wherein at least one *Brassica carinata* plant is the plant of embodiment 2.
12. A *Brassica carinata* seed produced by the method of embodiment 11.
13. A method for producing a first generation (F1) hybrid *Brassica carinata* seed comprising crossing the plant of embodiment 2 with a different *Brassica carinata* plant and harvesting the resultant F1 hybrid *carinata* seed, and wherein the plant of embodiment 2 is either a female parent or a male parent.
14. The method of embodiment 13 wherein the plant of embodiment 2 is the female parent.
15. The method of embodiment 13 wherein the plant of embodiment 2 is the male parent.
16. An F1 hybrid seed produced by the method of any one of embodiments 13 to 15.
17. An F1 hybrid plant grown from the F1 hybrid seed produced by the method of any one of embodiments 13 to 15.
18. A method for producing a Doubled Haploidy variety comprising:
   (a) isolating a flower bud of the F1 plant of embodiment 17;
   (b) dissecting out a haploid microspore;
   (c) placing the haploid microspore in culture;
   (d) inducing the microspore to differentiate into an embryo and subsequently into a plantlet;
   (e) identifying whether the plantlet contains a diploid chromosome number, wherein the diploid chromosome number occured through chromosome doubling; and
   (f) continuing to grow the plantlet if it contains a diploid chromosome number.
19. The method of embodiment 18 further comprising inducing chromosome doubling by chemical or physical means.
20. A plant, or part thereof, or seed of a Doubled Haploidy variety produced by the method of embodiment 18 or 19.
21. A method of producing a *Brassica carinata* variety produced from the plant of embodiment 2, wherein the *Brassica carinata* variety comprises a desired trait, the method comprising the steps of:
   (a) crossing a plant of cultivar AGR044-312D with another *Brassica carinata* variety comprising the desired trait;
   (b) growing the resultant F1 hybrid seed and selecting one or more progeny plants that have the desired trait;
   (c) backcrossing the selected progeny plants that have the desired trait with plants of cultivar AGR044-312D to produce backcross progeny seed; and
   (d) growing the resultant backcross progeny seed and selecting backcross progeny plants that have the desired trait to produce the *Brassica carinata* variety produced from cultivar AGR044-312D.
22. The method of embodiment 21, wherein steps (c) and (d) are repeated until the *Brassica carinata* variety produced from cultivar AGR044-312D has the desired trait and essentially all of the physiological and morphological characteristics of cultivar AGR044-312D when grown in the same location under the same environmental conditions.
23. The method of embodiment 21 or 22, wherein the desired trait is selected from the group consisting of male sterility, disease resistance, fungal resistance, pest resistance, herbicide tolerance, abiotic stress tolerance, and altered metabolism.
24. The method of embodiment 23, wherein the desired trait is herbicide tolerance and the tolerance is conferred to a herbicide selected from but not limited to the group consisting of glyphosate, glufosinate, imidazolinones, and auxin analogues such as 2,4-D and dicamba.
25. A plant, or part thereof, or seed of a *Brassica carinata* variety produced by the method of any one of embodiments 22 to 24.
26. A method of producing a *Brassica carinata* variety produced from the plant of embodiment 2, wherein the *Brassica carinata* variety comprises a desired trait, the method comprising introducing a DNA construct conferring the desired trait into a plant of cultivar AGR044-312D.
27. The method of embodiment 26, wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector.
28. The method of embodiment 26 or 27, wherein the DNA construct comprises a transgene.
29. The method of embodiment 26 or 27, wherein the DNA construct comprises an RNAi construct.
30. The method of any one of embodiments 26 to 29, wherein the *Brassica carinata* variety comprises the desired trait and essentially all of the physiological and morphological characteristics of cultivar AGR044-312D, when grown in the same location under the same environmental conditions.
31. The method of any one of embodiments 26 to 30, wherein the desired trait is selected from the group consisting of male sterility, disease resistance, fungal resistance, pest resistance, herbicide tolerance, abiotic stress tolerance, and altered metabolism.
32. The method of embodiment 31, wherein the desired trait is herbicide tolerance and the tolerance is conferred to a herbicide selected from but not limited to the group consisting of glyphosate, glufosinate, imidazolinones, and auxin analogues such as 2,4-D and dicamba.
33. A plant, or part thereof, or seed of a *Brassica carinata* variety produced by the method of any one of embodiments 26 to 32.
34. A method of producing a *Brassica carinata* variety produced from the plant of embodiment 2, wherein the *Brassica carinata* variety comprises a desired trait, the method comprising the steps of:
   (a) crossing a plant of cultivar AGR044-312D with another *Brassica carinata* variety comprising the desired trait;

(b) growing the resultant F1 hybrid seed and selecting one or more progeny plants that have the desired trait;
(c) selfing the progeny plants that have the desired trait to produce further progeny seed; and
(d) growing the further progeny seed and selecting further progeny plants that have the desired trait to produce the *Brassica carinata* variety produced from cultivar AGR044-312D.

35. The method of embodiment 34, wherein steps (c) and (d) are repeated until the *Brassica carinata* variety produced from cultivar AGR044-312D has the desired trait and essentially all of the physiological and morphological characteristics of cultivar AGR044-312D when grown in the same location under the same environmental conditions.

36. The method of embodiment 34 or 35, wherein the desired trait is selected from the group consisting of male sterility, disease resistance, fungal resistance, pest resistance, herbicide tolerance, abiotic stress tolerance, and altered metabolism.

37. The method of embodiment 36, wherein the desired trait is herbicide tolerance and the tolerance is conferred to a herbicide selected from but not limited to the group consisting of glyphosate, glufosinate, imidazolinones, and auxin analogues such as 2,4-D and dicamba.

38. A plant, or part thereof, or seed of a *Brassica carinata* variety produced by the method of any one of embodiments 34 to 37.

39. A method of producing a *Brassica carinata* variety produced from the plant of embodiment 2, wherein the *Brassica carinata* variety comprises a new trait, the method comprising exposing seedlings or microspores to a mutagenic agent and allowing the surviving fraction to develop into mature plants.

40. The method of embodiment 39, wherein the mutagenic agent is ethyl methanesulfonate, N-ethyl-N-nitrosourea, or x-ray, gamma or ultraviolet radiation.

41. A plant, or part thereof, or seed of a *Brassica carinata* variety produced by the method of embodiment 39 or 40.

42. A method of producing a *carinata* variety produced from the plant of embodiment 2, wherein the *carinata* variety comprises a desired trait, the method comprising:
(a) crossing a plant of cultivar AGR044-312D with a plant of another Brassicaceae species comprising the desired trait;
(b) using embryo rescue techniques to recover viable F1 plants from the cross or growing F1 seeds to produce F1 plants;
(c) selfing the F1 plants that have the desired trait and *carinata* character;
(d) using embryo rescue techniques to recover viable F2 plants or growing F2 seeds to produce F2 plants;
(e) selfing the F2 plants that have the desired trait and *carinata* character;
(f) using embryo rescue techniques to recover viable F3 plants or growing F3 seeds to produce progeny plants;
(g) selfing the progeny plants that have the desired trait and *carinata* character to produce further progeny plants; and
(h) selecting the progeny plants with the desired trait and *carinata* character to produce the *carinata* variety produced from cultivar AGR044-312D.

43. The method of embodiment 42, wherein steps (g) and (h) are repeated until the *carinata* variety produced from cultivar AGR044-312D has the desired trait and essentially all of the physiological and morphological characteristics of cultivar AGR044-312D when grown in the same location under the same environmental conditions.

44. The method of embodiment 42 or 43, wherein the desired trait is selected from the group consisting of male sterility, disease resistance, fungal resistance, pest resistance, herbicide tolerance, abiotic stress tolerance, and altered metabolism.

45. The method of embodiment 44, wherein the desired trait is herbicide tolerance and the tolerance is conferred to a herbicide selected from but not limited to the group consisting of glyphosate, glufosinate, imidazolinones, and auxin analogues such as 2,4-D and dicamba.

46. A plant, or part thereof, or seed of a progeny *carinata* variety produced by the method of any one of embodiments 42 to 45.

47. A method of producing a commercial plant product, the method comprising growing the plant of embodiment 2 to produce a commercial crop, and producing said commercial plant product from the commercial crop.

48. The method of embodiment 47, wherein the commercial plant product comprises oil, meal, or protein isolate.

49. A commercial plant product produced by the method of embodiment 47 or 48.

50. Oil, meal, or protein isolate produced by the method of embodiment 48.

51. Crushed, non-viable seed of *Brassica carinata* cultivar AGR044-312D, wherein a representative sample of said seed has been deposited under ATCC Accession number PTA-123015.

52. A cell of a seed of *Brassica carinata* cultivar designated AGR044-312D, wherein a representative sample of said seed has been deposited under ATCC Accession number PTA-123015.

53. A cell of a plant of *Brassica carinata* cultivar AGR044-312D, or a part thereof, produced from the seed defined in embodiment 52.

54. A protoplast of a plant of *Brassica carinata* cultivar AGR044-312D, or a part thereof, produced from the seed defined in embodiment 52.

55. The cell of embodiment 53, wherein the plant part is an ovule, a leaf, pollen, a seed, an embryo a root, a root tip, a pod, a flower, or a stalk.

56. The cell of embodiment 55, wherein the plant part is pollen.

57. The cell of embodiment 55, wherein the plant part is an ovule.

58. A cell of a *Brassica carinata* plant, or parts thereof, having essentially all of the physiological and morphological characteristics of the plant defined in embodiment 53 when grown in the same location under the same environmental conditions.

59. A tissue culture of protoplasts or regenerable cells of the plant, or part thereof, defined in embodiment 53.

60. The tissue culture according to embodiment 59, wherein the protoplasts or regenerable cells are produced from a tissue selected from the group consisting of leaves, pollen, embryos, roots, root tips, pods, flowers, ovules, and stalks.

61. A cell of a *Brassica carinata* plant regenerated from the tissue culture of embodiment 59 or 60, wherein said plant has essentially all of the morphological and physiological characteristics of cultivar AGR044-312D when grown in the same location under the same environmental conditions.
62. A cell of a regenerated *Brassica carinata* plant having essentially all of the physiological and morphological characteristics of cultivar AGR044-312D when grown in the same location under the same environmental conditions, the regenerated plant having been produced using a tissue culture, wherein the tissue culture is produced from the plant or part thereof defined in embodiment 53.
63. Use of a plant of *Brassica carinata* cultivar AGR044-312D, wherein a representative sample of said seed has been deposited under ATCC Accession number PTA-123015, to produce seed, wherein the seed is produced by self-fertilization or cross-fertilization.
64. Use of a plant of *Brassica carinata* cultivar AGR044-312D, wherein a representative sample of said seed has been deposited under ATCC Accession number PTA-123015 to produce an F1 hybrid *Brassica carinata* seed, wherein the plant is either a female parent or a male parent in a cross-fertilization.
65. The use of embodiment 64 wherein the plant is the female parent.
66. The use of embodiment 64 wherein the plant is the male parent.
67. A cell of an F1 hybrid plant grown from the F1 hybrid seed produced by the use according to any one of embodiments 64 to 66.
68. A cell of an F1 hybrid plant grown from F1 hybrid seed produced by a method comprising crossing a plant of *Brassica carinata* cultivar AGR044-312D, wherein a representative sample of said seed has been deposited under ATCC Accession number PTA-123015, with a different *Brassica carinata* plant and harvesting the resultant F1 hybrid *carinata* seed.
69. Use of a plant of *Brassica carinata* cultivar AGR044-312D, wherein a representative sample of said seed has been deposited under ATCC Accession number PTA-123015, to produce a Doubled Haploidy variety.
70. Use of embodiment 69, wherein chromosome doubling is introduced by chemical or physical means.
71. A cell of a Doubled Haploidy variety produced from *Brassica carinata* cultivar AGR044-312D, wherein a representative sample of the seed has been deposited under ATCC Accession number PTA-123015.
72. Use of a plant of *Brassica carinata* cultivar AGR044-312D, wherein a representative sample of said seed has been deposited under ATCC Accession number PTA-123015, to produce a *Brassica carinata* variety comprising a desired trait,
73. The use of embodiment 72, wherein the desired trait is selected from the group consisting of male sterility, disease resistance, fungal resistance, pest resistance, herbicide tolerance, abiotic stress tolerance, and altered metabolism.
74. The use of embodiment 73, wherein the desired trait is herbicide tolerance and the tolerance is conferred to a herbicide selected from but not limited to the group consisting of glyphosate, glufosinate, imidazolinones, and auxin analogues such as 2,4-D and dicamba.
75. A cell of a plant of a *Brassica carinata* variety produced from *Brassica carinata* cultivar AGR044-312D, wherein a representative sample of said seed has been deposited under ATCC Accession number PTA-123015, wherein the *Brassica carinata* variety comprises a desired trait, and wherein the *Brassica carinata* variety is produced by a method comprising the steps of:
    (a) crossing a plant of cultivar AGR044-312D with another *Brassica carinata* variety comprising the desired trait;
    (b) growing the resultant F1 hybrid seed and selecting one or more progeny plants that have the desired trait;
    (c) backcrossing the selected progeny plants that have the desired trait with plants of cultivar AGR044-312D to produce backcross progeny plants; and
    (d) growing the resultant backcross progeny seed and selecting backcross progeny plants that have the desired trait to produce the *Brassica carinata* variety produced from cultivar AGR044-312D.
76. The cell of embodiment 75, wherein the method to produce the *Brassica carinata* variety further comprises repeating steps (c) and (d) until the *Brassica carinata* variety produced from cultivar AGR044-312D has the desired trait and essentially all of the physiological and morphological characteristics of cultivar AGR044-312D when grown in the same location under the same environmental conditions.
77. The cell of embodiment 75 or 76, wherein the desired trait is selected from the group consisting of male sterility, disease resistance, fungal resistance, pest resistance, herbicide tolerance, abiotic stress tolerance, and altered metabolism.
78. The cell of embodiment 77, wherein the desired trait is herbicide tolerance and the tolerance is conferred to a herbicide selected from but not limited to the group consisting of glyphosate, glufosinate, imidazolinones, and auxin analogues such as 2,4-D and dicamba.
79. Use of a plant of *Brassica carinata* cultivar AGR044-312D, wherein a representative sample of said seed has been deposited under ATCC Accession number PTA-123015, to produce a *Brassica carinata* variety comprising a desired trait, wherein the desired trait is conferred by a DNA construct.
80. The use of embodiment 79, wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector.
81. The use of embodiment 79 or 80, wherein the DNA construct comprises a transgene.
82. The use of embodiment 79 or 80, wherein the DNA construct comprises an RNAi construct.
83. The use of any one of embodiments 79 to 82, wherein the *Brassica carinata* variety comprises the desired trait and essentially all of the physiological and morphological characteristics of cultivar AGR044-312D when grown in the same location under the same environmental conditions.
84. The use of any one of embodiments 79 to 83, wherein the desired trait is selected from the group consisting of male sterility, disease resistance, fungal resistance, pest resistance, herbicide tolerance, abiotic stress tolerance, and altered metabolism.
85. The use of embodiment 84, wherein the desired trait is herbicide tolerance and the tolerance is conferred to a herbicide selected from but not limited to the group consisting of glyphosate, glufosinate, imidazolinones, and auxin analogues such as 2,4-D and dicamba.

86. A cell of a plant of a *Brassica carinata* variety produced from cultivar AGR044-312D, the seed of which has been deposited under ATCC Accession number PTA-123015, wherein the *Brassica carinata* variety comprises a desired trait, and wherein the *Brassica carinata* variety was produced by a method comprising introducing a DNA construct conferring the desired trait into a plant of cultivar AGR044-312D.

87. The cell of embodiment 86, wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector.

88. The cell of embodiment 86 or 87, wherein the DNA construct comprises a transgene.

89. The cell of embodiment 86 or 87, wherein the DNA construct comprises an RNAi construct.

90. The cell of any one of embodiments 86 to 89, wherein the *Brassica carinata* variety comprises the desired trait and essentially all of the physiological and morphological characteristics of cultivar AGR044-312D when grown in the same location under the same environmental conditions.

91. The cell of any one of embodiments 86 to 90, wherein the desired trait is selected from the group consisting of male sterility, disease resistance, fungal resistance, pest resistance, herbicide tolerance, abiotic stress tolerance, and altered metabolism.

92. The cell of embodiment 91, wherein the desired trait is herbicide tolerance and the tolerance is conferred to a herbicide selected from but not limited to the group consisting of glyphosate, glufosinate, imidazolinones, and auxin analogues such as 2,4-D and dicamba.

93. A cell of a plant of a *Brassica carinata* variety produced from cultivar AGR044-312D, the seed of which has been deposited under ATCC Accession number PTA-123015, wherein the *Brassica carinata* variety comprises a desired trait, and wherein the *Brassica carinata* variety was produced by a method comprising the steps of:
  (a) crossing a plant of cultivar AGR044-312D with a plant of another *Brassica carinata* variety comprising the desired trait;
  (b) growing the resultant F1 hybrid seed and selecting one or more progeny plants that have the desired trait;
  (c) selfing the progeny plants that have the desired trait to produce further progeny plants; and
  (d) growing the resultant further progeny plants and selecting further progeny plants that have the desired trait to produce the *Brassica carinata* variety produced from cultivar AGR044-312D.

94. The cell of embodiment 93, wherein steps (c) and (d) are repeated until the *Brassica carinata* variety produced from cultivar AGR044-312D has the desired trait and essentially all of the physiological and morphological characteristics of cultivar AGR044-312D when grown in the same location under the same environmental conditions.

95. The cell of embodiment 93 or 94, wherein the desired trait is selected from the group consisting of male sterility, disease resistance, fungal resistance, pest resistance, herbicide tolerance, abiotic stress tolerance, and altered metabolism.

96. The cell of embodiment 95, wherein the desired trait is herbicide tolerance and the tolerance is conferred to a herbicide selected from but not limited to the group consisting of glyphosate, glufosinate, imidazolinones, and auxin analogues such as 2,4-D and dicamba.

97. Use of a plant of *Brassica carinata* cultivar AGR044-312D, wherein a representative sample of said seed has been deposited under ATCC Accession number PTA-123015, to produce a *Brassica carinata* variety comprising a new trait, wherein the new trait is introduced by exposing seedlings or microspores to a mutagenic agent.

98. The use of embodiment 97, wherein the mutagenic agent is ethyl methanesulfonate, N-ethyl-N-nitrosourea, or x-ray, gamma or ultraviolet radiation.

99. A cell of a plant of a *Brassica carinata* variety produced from cultivar AGR044-312D, wherein a representative sample of said seed has been deposited under ATCC Accession number PTA-123015, wherein the *Brassica carinata* variety comprises a new trait, and wherein the *Brassica carinata* variety is produced by a method comprising exposing seedlings or microspores to a mutagenic agent and allowing the surviving fraction to develop into mature plants.

100. The cell of embodiment 99, wherein the mutagenic agent is ethyl methanesulfonate, N-ethyl-N-nitrosourea, or x-ray, gamma or ultraviolet radiation.

101. Use of a plant of *Brassica carinata* cultivar AGR044-312D, wherein a representative sample of said seed has been deposited under ATCC Accession number PTA-123015, to produce a *carinata* variety comprising a desired trait, wherein the desired trait is introduced by crossing a plant of cultivar AGR044-312D with a plant of another Brassicaceae species comprising the desired trait.

102. The use of embodiment 101, wherein the *carinata* variety produced from cultivar AGR044-312D has the desired trait and essentially all of the physiological and morphological characteristics of cultivar AGR044-312D when grown in the same location under the same environmental conditions.

103. The use of embodiment 101 or 102, wherein the desired trait is selected from the group consisting of male sterility, disease resistance, fungal resistance, pest resistance, herbicide tolerance, abiotic stress tolerance, and altered metabolism.

104. The use of embodiment 103, wherein the desired trait is herbicide tolerance and the tolerance is conferred to a herbicide selected from but not limited to the group consisting of glyphosate, glufosinate, imidazolinones, and auxin analogues such as 2,4-D and dicamba.

105. A cell of a plant of a *carinata* variety comprising a desired trait, wherein the *carinata* variety is produced by a method comprising:
  (a) crossing a plant of cultivar AGR044-312D with a plant of another Brassicaceae species comprising the desired trait;
  (b) using embryo rescue techniques to recover viable F1 plants from the cross or growing F1 seeds to produce F1 plants;
  (c) selfing the F1 plants that have the desired trait and *carinata* character;
  (d) using embryo rescue techniques to recover viable F2 plants or growing F2 seeds to produce F2 plants;
  (e) selfing the F2 plants that have the desired trait and *carinata* character;
  (f) using embryo rescue techniques to recover viable F3 plants or growing F3 seeds to produce progeny plants;

(g) selfing the progeny plants that have the desired trait and *carinata* character to produce further progeny plants; and
(h) selecting the progeny plants with the desired trait and *carinata* character to produce the *carinata* variety produced from cultivar AGR044-312D.
106. The cell of embodiment 105, wherein steps (g) and (h) are repeated until the *carinata* variety produced from cultivar AGR044-312D has the desired trait and essentially all of the physiological and morphological characteristics of cultivar AGR044-312D when grown in the same location under the same environmental conditions.
107. The method of embodiment 105 or 106, wherein the desired trait is selected from the group consisting of male sterility, disease resistance, fungal resistance, pest resistance, herbicide tolerance, abiotic stress tolerance, and altered metabolism.
108. The method of embodiment 107, wherein the desired trait is herbicide tolerance and the tolerance is conferred to a herbicide selected from but not limited to the group consisting of glyphosate, glufosinate, imidazolinones, and auxin analogues such as 2,4-D and dicamba.
109. Use of a plant of *Brassica carinata* cultivar AGR044-312D, wherein a representative sample of said seed has been deposited under ATCC Accession number PTA-123015, to produce a commercial crop.
110. Use of a plant of *Brassica carinata* cultivar AGR044-312D, wherein a representative sample of said seed has been deposited under ATCC Accession number PTA-123015, to produce a commercial plant product.
111. The use of embodiment 110, wherein the commercial plant product comprises oil, meal, or protein isolate.
112. A seed of *Brassica carinata* cultivar designated AGR044-3A22, wherein a representative sample of the seed has been deposited under ATCC Accession number PTA-123014.
113. A plant of *Brassica carinata* cultivar AGR044-3A22, or a part thereof, produced from the seed of embodiment 112.
114. The plant part of embodiment 113, wherein the plant part is an ovule, a leaf, pollen, a seed, an embryo a root, a root tip, a pod, a flower, a stalk, a cell, or a protoplast.
115. The plant part of embodiment 114, wherein the plant part is pollen.
116. The plant part of embodiment 115, wherein the plant part is an ovule.
117. A *Brassica carinata* plant, or parts thereof, having essentially all of the physiological and morphological characteristics of the plant of embodiment 113 when grown in the same location under the same environmental conditions.
118. A tissue culture of protoplasts or regenerable cells of the plant, or part thereof, of embodiment 113
119. The tissue culture according to embodiment 118, wherein the protoplasts or regenerable cells are produced from a tissue selected from the group consisting of leaves, pollen, embryos, roots, root tips, pods, flowers, ovules, and stalks.
120. A *Brassica carinata* plant regenerated from the tissue culture of embodiment 118 or 119, wherein the plant has essentially all of the morphological and physiological characteristics of cultivar AGR044-3A22, the seed of which has been deposited under ATCC Accession number PTA-123014, when grown in the same location under the same environmental conditions.
121. A regenerated *Brassica carinata* plant having essentially all of the physiological and morphological characteristics of the cultivar AGR044-3A22 when grown in the same location under the same environmental conditions, the regenerated plant having been produced using a tissue culture, wherein the tissue culture is produced from the plant or part thereof of embodiment 113.
122. A method for producing *Brassica carinata* seed comprising crossing *Brassica carinata* plants and harvesting the resulting *Brassica carinata* seed, wherein at least one *Brassica carinata* plant is the plant of embodiment 113.
123. A *Brassica carinata* seed produced by the method of embodiment 122.
124. A method for producing a first generation (F1) hybrid *Brassica carinata* seed comprising crossing the plant of embodiment 113 with a different *Brassica carinata* plant and harvesting the resultant F1 hybrid *carinata* seed, and wherein the plant of embodiment 113 is either a female parent or a male parent.
125. The method of embodiment 124 wherein the plant of embodiment 113 is the female parent.
126. The method of embodiment 124 wherein the plant of embodiment 113 is the male parent.
127. An F1 hybrid seed produced by the method of any one of embodiments 124 to 126.
128. An F1 hybrid plant grown from the F1 hybrid seed produced by the method of any one of embodiments 124 to 126.
129. A method for producing a Doubled Haploidy variety comprising:
(a) isolating a flower bud of the F1 plant of embodiment 128;
(b) dissecting out a haploid microspore;
(c) placing the haploid microspore in culture;
(d) inducing the microspore to differentiate into an embryo and subsequently into a plantlet;
(e) identifying whether the plantlet contains a diploid chromosome number, wherein the diploid chromosome number occured through chromosome doubling; and
(f) continuing to grow the plantlet if it contains a diploid chromosome number.
130. The method of embodiment 129 further comprising inducing chromosome doubling by chemical or physical means.
131. A plant, or part thereof, or seed of a Doubled Haploidy variety produced by the method of embodiment 129 to 130.
132. A method of producing a *Brassica carinata* variety produced from the plant of embodiment 113, wherein the *Brassica carinata* variety comprises a desired trait, the method comprising the steps of:
(a) crossing a plant of cultivar AGR044-3A22 with another *Brassica carinata* variety comprising the desired trait;
(b) growing the resultant F1 hybrid seed and selecting one or more progeny plants that have the desired trait;
(c) backcrossing the selected progeny plants that have the desired trait with plants of cultivar AGR044-3A22 to produce backcross progeny seed; and
(d) growing the resultant backcross progeny seed and selecting backcross progeny plants that have the desired trait to produce the *Brassica carinata* variety produced from cultivar AGR044-3A22.

133. The method of embodiment 132, wherein steps (c) and (d) are repeated until the *Brassica carinata* variety produced from cultivar AGR044-3A22 has the desired trait and essentially all of the physiological and morphological characteristics of cultivar AGR044-3A22 when grown in the same location under the same environmental conditions.

134. The method of embodiment 132 or 133, wherein the desired trait is selected from the group consisting of male sterility, disease resistance, fungal resistance, pest resistance, herbicide tolerance, abiotic stress tolerance, and altered metabolism.

135. The method of embodiment 134, wherein the desired trait is herbicide tolerance and the tolerance is conferred to a herbicide selected from but not limited to the group consisting of glyphosate, glufosinate, imidazolinones, and auxin analogues such as 2,4-D and dicamba.

136. A plant, or part thereof, or seed of a *Brassica carinata* variety produced by the method of any one of embodiments 132 to 135.

137. A method of producing a *Brassica carinata* variety produced from the plant of embodiment 113, wherein the *Brassica carinata* variety comprises a desired trait, the method comprising introducing a DNA construct conferring the desired trait into a plant of cultivar AGR044-3A22.

138. The method of embodiment 137, wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector.

139. The method of embodiment 137 or 138, wherein the DNA construct comprises a transgene.

140. The method of embodiment 137 or 138, wherein the DNA construct comprises an RNAi construct.

141. The method of any one of embodiments 137 to 140, wherein the *Brassica carinata* variety comprises the desired trait and essentially all of the physiological and morphological characteristics of cultivar AGR044-3A22, when grown in the same location under the same environmental conditions.

142. The method of any one of embodiments 137 to 141, wherein the desired trait is selected from the group consisting of male sterility, disease resistance, fungal resistance, pest resistance, herbicide tolerance, abiotic stress tolerance, and altered metabolism.

143. The method of embodiment 142, wherein the desired trait is herbicide tolerance and the tolerance is conferred to a herbicide selected from but not limited to the group consisting of glyphosate, glufosinate, imidazolinones, and auxin analogues such as 2,4-D and dicamba.

144. A plant, or part thereof, or seed of a *Brassica carinata* variety produced by the method of any one of embodiments 137 to 143.

145. A method of producing a *Brassica carinata* variety produced from the plant of embodiment 113, wherein the *Brassica carinata* variety comprises a desired trait, the method comprising the steps of:
(a) crossing a plant of cultivar AGR044-3A22 with another *Brassica carinata* variety comprising the desired trait;
(b) growing the resultant F1 hybrid seed and selecting one or more progeny plants that have the desired trait;
(c) selfing the progeny plants that have the desired trait to produce further progeny seed; and
(d) growing the further progeny seed and selecting further progeny plants that have the desired trait to produce the *Brassica carinata* variety produced from cultivar AGR044-3A22.

146. The method of embodiment 145, wherein steps (c) and (d) are repeated until the *Brassica carinata* variety produced from cultivar AGR044-3A22 has the desired trait and essentially all of the physiological and morphological characteristics of cultivar AGR044-3A22 when grown in the same location under the same environmental conditions.

147. The method of embodiment 145 or 146, wherein the desired trait is selected from the group consisting of male sterility, disease resistance, fungal resistance, pest resistance, herbicide tolerance, abiotic stress tolerance, and altered metabolism.

148. The method of embodiment 147, wherein the desired trait is herbicide tolerance and the tolerance is conferred to a herbicide selected from but not limited to the group consisting of glyphosate, glufosinate, imidazolinones, and auxin analogues such as 2,4-D and dicamba.

149. A plant, or part thereof, or seed of a *Brassica carinata* variety produced by the method of any one of embodiments 145 to 148.

150. A method of producing a *Brassica carinata* variety produced from the plant of embodiment 113, wherein the *Brassica carinata* variety comprises a new trait, the method comprising exposing seedlings or microspores to a mutagenic agent and allowing the surviving fraction to develop into mature plants.

151. The method of embodiment 150, wherein the mutagenic agent is ethyl methanesulfonate, N-ethyl-N-nitrosourea, or x-ray, gamma or ultraviolet radiation.

152. A plant, or part thereof, or seed of a *Brassica carinata* variety produced by the method of embodiment 150 or 151.

153. A method of producing a *carinata* variety produced from the plant of embodiment 113, wherein the *carinata* variety comprises a desired trait, the method comprising:
(a) crossing a plant of cultivar AGR044-3A22 with a plant of another Brassicaceae species comprising the desired trait;
(b) using embryo rescue techniques to recover viable F1 plants from the cross or growing F1 seeds to produce F1 plants;
(c) selfing the F1 plants that have the desired trait and *carinata* character;
(d) using embryo rescue techniques to recover viable F2 plants or growing F2 seeds to produce F2 plants;
(e) selfing the F2 plants that have the desired trait and *carinata* character;
(f) using embryo rescue techniques to recover viable F3 plants or growing F3 seeds to produce progeny plants;
(g) selfing the progeny plants that have the desired trait and *carinata* character to produce further progeny plants; and
(h) selecting the progeny plants with the desired trait and *carinata* character to produce the *carinata* variety produced from cultivar AGR044-3A22.

154. The method of embodiment 153, wherein steps (g) and (h) are repeated until the *carinata* variety produced from cultivar AGR044-3A22 has the desired trait and essentially all of the physiological and morphological characteristics of cultivar AGR044-3A22 when grown in the same location under the same environmental conditions.
155. The method of embodiment 153 or 154, wherein the desired trait is selected from the group consisting of male sterility, disease resistance, fungal resistance, pest resistance, herbicide tolerance, abiotic stress tolerance, and altered metabolism.
156. The method of embodiment 155, wherein the desired trait is herbicide tolerance and the tolerance is conferred to a herbicide selected from but not limited to the group consisting of glyphosate, glufosinate, imidazolinones, and auxin analogues such as 2,4-D and dicamba.
157. A plant, or part thereof, or seed of a progeny *carinata* variety produced by the method of any one of embodiments 153 to 156.
158. A method of producing a commercial plant product, the method comprising growing the plant of embodiment 113 to produce a commercial crop, and producing said commercial plant product from the commercial crop.
159. The method of embodiment 158, wherein the commercial plant product comprises oil, meal, or protein isolate.
160. A commercial plant product produced by the method of embodiment 158 or 159.
161. Oil, meal, or protein isolate produced by the method of embodiment 159.
162. Crushed, non-viable seed of *Brassica carinata* cultivar AGR044-3A22, wherein a representative sample of said seed has been deposited under ATCC Accession number PTA-123014.
163. A cell of a seed of *Brassica carinata* cultivar designated AGR044-3A22, wherein a representative sample of said seed has been deposited under ATCC Accession number PTA-123014.
164. A cell of a plant of *Brassica carinata* cultivar AGR044-3A22, or a part thereof, produced from the seed defined in embodiment 163.
165. A protoplast of a plant of *Brassica carinata* cultivar AGR044-3A22, or a part thereof, produced from the seed defined in embodiment 163.
166. The cell of embodiment 164, wherein the plant part is an ovule, a leaf, pollen, a seed, an embryo a root, a root tip, a pod, a flower, or a stalk.
167. The cell of embodiment 166, wherein the plant part is pollen.
168. The cell of embodiment 166, wherein the plant part is an ovule.
169. A cell of a *Brassica carinata* plant, or parts thereof, having essentially all of the physiological and morphological characteristics of the plant defined in embodiment 163 when grown in the same location under the same environmental conditions.
170. A tissue culture of protoplasts or regenerable cells of the plant, or part thereof, defined in embodiment 163.
171. The tissue culture according to embodiment 170, wherein the protoplasts or regenerable cells are produced from a tissue selected from the group consisting of leaves, pollen, embryos, roots, root tips, pods, flowers, ovules, and stalks.
172. A cell of a *Brassica carinata* plant regenerated from the tissue culture of embodiment 170 or 171, wherein said plant has essentially all of the morphological and physiological characteristics of cultivar AGR044-3A22 when grown in the same location under the same environmental conditions.
173. A cell of a regenerated *Brassica carinata* plant having essentially all of the physiological and morphological characteristics of cultivar AGR044-3A22 when grown in the same location under the same environmental conditions, the regenerated plant having been produced using a tissue culture, wherein the tissue culture is produced from the plant or part thereof defined in embodiment 165.
174. Use of a plant of *Brassica carinata* cultivar AGR044-3A22, wherein a representative sample of said seed has been deposited under ATCC Accession number PTA-123014, to produce seed, wherein the seed is produced by self-fertilization or cross-fertilization.
175. Use of a plant of *Brassica carinata* cultivar AGR044-3A22, wherein a representative sample of said seed has been deposited under ATCC Accession number PTA-123014 to produce an F1 hybrid *Brassica carinata* seed, wherein the plant is either a female parent or a male parent in a cross-fertilization.
176. The use of embodiment 175 wherein the plant is the female parent.
177. The use of embodiment 175 wherein the plant is the male parent.
178. A cell of an F1 hybrid plant grown from the F1 hybrid seed produced by the use according to any one of embodiments 175 to 177.
179. A cell of an F1 hybrid plant grown from F1 hybrid seed produced by a method comprising crossing a plant of *Brassica carinata* cultivar AGR044-3A22, wherein a representative sample of said seed has been deposited under ATCC Accession number PTA-123014, with a different *Brassica carinata* plant and harvesting the resultant F1 hybrid *carinata* seed.
180. Use of a plant of *Brassica carinata* cultivar AGR044-3A22, wherein a representative sample of said seed has been deposited under ATCC Accession number PTA-123014, to produce a Doubled Haploidy variety.
181. Use of embodiment 180, wherein chromosome doubling is introduced by chemical or physical means.
182. A cell of a Doubled Haploidy variety produced from *Brassica carinata* cultivar AGR044-3A22, wherein a representative sample of the seed has been deposited under ATCC Accession number PTA-123014.
183. Use of a plant of *Brassica carinata* cultivar AGR044-3A22, wherein a representative sample of said seed has been deposited under ATCC Accession number PTA-123014, to produce a *Brassica carinata* variety comprising a desired trait.
184. The use of embodiment 183, wherein the desired trait is selected from the group consisting of male sterility, disease resistance, fungal resistance, pest resistance, herbicide tolerance, abiotic stress tolerance, and altered metabolism.
185. The use of embodiment 184, wherein the desired trait is herbicide tolerance and the tolerance is conferred to a herbicide selected from but not limited to the group consisting of glyphosate, glufosinate, imidazolinones, and auxin analogues such as 2,4-D and dicamba.
186. A cell of a plant of a *Brassica carinata* variety produced from *Brassica carinata* cultivar AGR044-3A22, wherein a representative sample of said seed has been deposited under ATCC Accession number PTA-123014, wherein the *Brassica carinata* variety comprises a desired trait, and wherein the *Brassica carinata* variety is produced by a method comprising the steps of:
  (a) crossing a plant of cultivar AGR044-3A22 with another *Brassica carinata* variety comprising the desired trait;
  (b) growing the resultant F1 hybrid seed and selecting one or more progeny plants that have the desired trait;
  (c) backcrossing the selected progeny plants that have the desired trait with plants of cultivar AGR044-3A22 to produce backcross progeny plants; and
  (d) growing the resultant backcross progeny seed and selecting backcross progeny plants that have the desired trait to produce the *Brassica carinata* variety produced from cultivar AGR044-3A22.

187. The cell of embodiment 186, wherein the method to produce the *Brassica carinata* variety further comprises repeating steps (c) and (d) until the *Brassica carinata* variety produced from cultivar AGR044-3A22 has the desired trait and essentially all of the physiological and morphological characteristics of cultivar AGR044-3A22 when grown in the same location under the same environmental conditions.

188. The cell of embodiment 186 or 187, wherein the desired trait is selected from the group consisting of male sterility, disease resistance, fungal resistance, pest resistance, herbicide tolerance, abiotic stress tolerance, and altered metabolism.

189. The cell of embodiment 188, wherein the desired trait is herbicide tolerance and the tolerance is conferred to a herbicide selected from but not limited to the group consisting of glyphosate, glufosinate, imidazolinones, and auxin analogues such as 2,4-D and dicamba.

190. Use of a plant of *Brassica carinata* cultivar AGR044-3A22, wherein a representative sample of said seed has been deposited under ATCC Accession number PTA-123014, to produce a *Brassica carinata* variety comprising a desired trait, wherein the desired trait is conferred by a DNA construct.

191. The use of embodiment 190, wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector.

192. The use of embodiment 190 or 191, wherein the DNA construct comprises a transgene.

193. The use of embodiment 190 or 191, wherein the DNA construct comprises an RNAi construct.

194. The use of any one of embodiments 190 to 193, wherein the *Brassica carinata* variety comprises the desired trait and essentially all of the physiological and morphological characteristics of cultivar AGR044-3A22 when grown in the same location under the same environmental conditions.

195. The use of any one of embodiments 190 to 194, wherein the desired trait is selected from the group consisting of male sterility, disease resistance, fungal resistance, pest resistance, herbicide tolerance, abiotic stress tolerance, and altered metabolism.

196. The use of embodiment 195, wherein the desired trait is herbicide tolerance and the tolerance is conferred to a herbicide selected from but not limited to the group consisting of glyphosate, glufosinate, imidazolinones, and auxin analogues such as 2,4-D and dicamba.

197. A cell of a plant of a *Brassica carinata* variety produced from cultivar AGR044-3A22, the seed of which has been deposited under ATCC Accession number PTA-123014, wherein the *Brassica carinata* variety comprises a desired trait, and wherein the *Brassica carinata* variety was produced by a method comprising introducing a DNA construct conferring the desired trait into a plant of cultivar AGR044-3A22.

198. The cell of embodiment 197, wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector.

199. The cell of embodiment 197 or 198, wherein the DNA construct comprises a transgene.

200. The cell of embodiment 197 or 198, wherein the DNA construct comprises an RNAi construct.

201. The cell of any one of embodiments 197 to 200, wherein the *Brassica carinata* variety comprises the desired trait and essentially all of the physiological and morphological characteristics of cultivar AGR044-3A22 when grown in the same location under the same environmental conditions.

202. The cell of any one of embodiments 197 to 201, wherein the desired trait is selected from the group consisting of male sterility, disease resistance, fungal resistance, pest resistance, herbicide tolerance, abiotic stress tolerance, and altered metabolism.

203. The cell of embodiment 202, wherein the desired trait is herbicide tolerance and the tolerance is conferred to a herbicide selected from but not limited to the group consisting of glyphosate, glufosinate, imidazolinones, and auxin analogues such as 2,4-D and dicamba.

204. A cell of a plant of a *Brassica carinata* variety produced from cultivar AGR044-3A22, the seed of which has been deposited under ATCC Accession number PTA-123014, wherein the *Brassica carinata* variety comprises a desired trait, and wherein the *Brassica carinata* variety was produced by a method comprising the steps of:
  (a) crossing a plant of cultivar AGR044-3A22 with a plant of another *Brassica carinata* variety comprising the desired trait;
  (b) growing the resultant F1 hybrid seed and selecting one or more progeny plants that have the desired trait;
  (c) selfing the progeny plants that have the desired trait to produce further progeny plants; and
  (d) growing the resultant further progeny plants and selecting further progeny plants that have the desired trait to produce the *Brassica carinata* variety produced from cultivar AGR044-3A22.

205. The cell of embodiment 204, wherein steps (c) and (d) are repeated until the *Brassica carinata* variety produced from cultivar AGR044-3A22 has the desired trait and essentially all of the physiological and morphological characteristics of cultivar AGR044-3A22 when grown in the same location under the same environmental conditions.

206. The cell of embodiment 204 or 205, wherein the desired trait is selected from the group consisting of male sterility, disease resistance, fungal resistance, pest resistance, herbicide tolerance, abiotic stress tolerance, and altered metabolism.

207. The cell of embodiment 206, wherein the desired trait is herbicide tolerance and the tolerance is conferred to a herbicide selected from but not limited to the group consisting of glyphosate, glufosinate, imidazolinones, and auxin analogues such as 2,4-D and dicamba.

208. Use of a plant of *Brassica carinata* cultivar AGR044-3A22, wherein a representative sample of said seed has been deposited under ATCC Accession number PTA-123014, to produce a *Brassica carinata* variety comprising a new trait, wherein the new trait is introduced by exposing seedlings or microspores to a mutagenic agent.

209. The use of embodiment 208, wherein the mutagenic agent is ethyl methanesulfonate, N-ethyl-N-nitrosourea, or x-ray, gamma or ultraviolet radiation.

210. A cell of a plant of a *Brassica carinata* variety produced from cultivar AGR044-3A22, wherein a representative sample of said seed has been deposited under ATCC Accession number PTA-123014, wherein the *Brassica carinata* variety comprises a new trait, and wherein the *Brassica carinata* variety is produced by a method comprising exposing seedlings or microspores to a mutagenic agent and allowing the surviving fraction to develop into mature plants.

211. The cell of embodiment 210, wherein the mutagenic agent is ethyl methanesulfonate, N-ethyl-N-nitrosourea, or x-ray, gamma or ultraviolet radiation.

212. Use of a plant of *Brassica carinata* cultivar AGR044-3A22, wherein a representative sample of said seed has been deposited under ATCC Accession number PTA-123014, to produce a *carinata* variety comprising a desired trait, wherein the desired trait is introduced by crossing a plant of cultivar AGR044-3A22 with a plant of another Brassicaceae species comprising the desired trait.

213. The use of embodiment 212, wherein the *carinata* variety produced from cultivar AGR044-3A22 has the desired trait and essentially all of the physiological and morphological characteristics of cultivar AGR044-3A22 when grown in the same location under the same environmental conditions.

214. The use of embodiment 212 or 213, wherein the desired trait is selected from the group consisting of male sterility, disease resistance, fungal resistance, pest resistance, herbicide tolerance, abiotic stress tolerance, and altered metabolism.

215. The use of embodiment 214, wherein the desired trait is herbicide tolerance and the tolerance is conferred to a herbicide selected from but not limited to the group consisting of glyphosate, glufosinate, imidazolinones, and auxin analogues such as 2,4-D and dicamba.

216. A cell of a plant of a *carinata* variety comprising a desired trait, wherein the *carinata* variety is produced by a method comprising:
  (a) crossing a plant of cultivar AGR044-3A22 with a plant of another Brassicaceae species comprising the desired trait;
  (b) using embryo rescue techniques to recover viable F1 plants from the cross or growing F1 seeds to produce F1 plants;
  (c) selfing the F1 plants that have the desired trait and *carinata* character;
  (d) using embryo rescue techniques to recover viable F2 plants or growing F2 seeds to produce F2 plants;
  (e) selfing the F2 plants that have the desired trait and *carinata* character;
  (f) using embryo rescue techniques to recover viable F3 plants or growing F3 seeds to produce progeny plants;
  (g) selfing the progeny plants that have the desired trait and *carinata* character to produce further progeny plants; and
  (h) selecting the progeny plants with the desired trait and *carinata* character to produce the *carinata* variety produced from cultivar AGR044-3A22.

217. The cell of embodiment 216, wherein steps (g) and (h) are repeated until the *carinata* variety produced from cultivar AGR044-3A22 has the desired trait and essentially all of the physiological and morphological characteristics of cultivar AGR044-3A22 when grown in the same location under the same environmental conditions.

218. The method of embodiment 216 or 217, wherein the desired trait is selected from the group consisting of male sterility, disease resistance, fungal resistance, pest resistance, herbicide tolerance, abiotic stress tolerance, and altered metabolism.

219. The method of embodiment 218, wherein the desired trait is herbicide tolerance and the tolerance is conferred to a herbicide selected from but not limited to the group consisting of glyphosate, glufosinate, imidazolinones, and auxin analogues such as 2,4-D and dicamba.

220. Use of a plant of *Brassica carinata* cultivar AGR044-3A22, wherein a representative sample of said seed has been deposited under ATCC Accession number PTA-123014, to produce a commercial crop.

221. Use of a plant of *Brassica carinata* cultivar AGR044-3A22, wherein a representative sample of said seed has been deposited under ATCC Accession number PTA-123014, to produce a commercial plant product.

222. The use of embodiment 221, wherein the commercial plant product comprises oil, meal, or protein isolate.

4. EVALUATION CRITERIA

In the description and tables which follow a number of terms are used. In order to aid in a clear and consistent understanding of the specification the following definitions and/or explanations of the assessment of the evaluation criteria are provided.

Type. Type refers to whether the new cultivar is considered to be primarily a Spring or Winter type of *Brassica carinata*.

Ploidy. Ploidy refers to whether the number of chromosomes exhibited by the cultivar is diploid or tetraploid.

Leaf Anthocyanin Coloration. The presence or absence of leaf anthocyanin coloration and the degree thereof if present are observed when the plant has reached the 9 to 11 leaf-stage.

Time of Flowering. A determination is made of the number of days when at least 50 percent of the plants have one or more open buds on a terminal raceme in the year of sowing.

Plant Height. The overall plant height at the end of flowering is observed (mean of 50).

Flower Petal Coloration. The coloration of open exposed petals on the first day of flowering is observed.

Pod Anthocyanin Coloration. The presence or absence at maturity of silique anthocyanin coloration, and the degree thereof if present are observed.

Silique attitude (Pod Habit). The typical manner in which the silique are borne on the plant at maturity is observed.

Maturity. The number of days from planting to maturity is observed with maturity being defined as the plant stage when pods with seed color change, occurring from green to brown or black, on the bottom third of the pod bearing area of the main stem.

Seeds Per Pod. The average number of seeds per pod is observed (mean of 50).

Seed Size. The weight in grams of 1,000 typical seeds is determined at maturity while such seeds exhibit a moisture content of approximately 5 to 6 percent by weight.

Seed Coat Color. The seed coat color of typical mature seeds is observed.

NIR analysis: Near infrared spectroscopy screening is a non-destructive method that allows one to determine the NIR absorption spectra of intact samples of material such as plant seed. Once the absorption spectra of the sample is determined, it can be used to determine the sample's content of compounds such as protein, oil, fatty acids, glucosinolates and others. This is done by comparing the spectra to those of calibrated samples. Calibration was developed in-house by correlating the NIR spectra with experimentally-measured seed quality parameters of over 700 diverse carinata lines. These lines comprise a highly-diverse range of oil contents, profiles, glucosinolate levels, seed colours, etc. and have been collected from regions all around the world.

Oil Content: The typical percentage by weight oil present in the mature whole dried seeds is determined by Near Infrared Spectroscopy (NIR).

Protein Content: The typical percentage by weight of protein in the oil free meal of the mature whole dried seeds is determined by NIR analysis.

Fatty Acid Content: The typical percentages by weight of fatty acids present in the endogenously formed oil of the mature whole dried seeds are determined by NIR analysis. Seed oil of *Brassica carinata* and other *brassica* oilseeds, are comprised largely of mono and poly unsaturated fatty acids ranging from 18 to 22 carbons in chain length Of the monosunsaturated fatty acids, one finds predominantly oleic acid, (c18.1), gondoic acid (C20.1) erucic acid (C22.1). Of the poly uncaturated fatty acids, one finds predominantly Linoleiic (C18.2) and Linolenic (c18.3). The remaining fraction is comprised of saturated fatty acids (SATS), including Lauric (C12.0), Myristic acid (C14.0), Palmitic acid (C16) and Stearic acid (C18.0)

Glucosinolate Content. The total aliphatic glucosinolate content of the meal of the seeds is determined by NIR and is expressed as micromoles per gram seed weight.

Resistance to Shattering. Resistance to silique shattering is observed at seed maturity and is expressed on a scale of 1 (poor) to 5 (excellent).

Resistant to Lodging. Resistance to lodging at maturity and is expressed on a scale of 1 (weak) to 5 (strong).

Frost Tolerance (Spring Type Only). The ability of young plants to withstand late spring frosts at a typical growing area is evaluated and is expressed on a scale of 1 (poor) to 5 (excellent).

Disease Resistance: Resistant to various diseases is evaluated and is expressed on a scale of 0 (not tested), 1 (susceptible), 2 (low resistance), 3 (moderate resistance), or 4 (high resistance).

Herbicide Resistance: Resistance to various herbicides when applied at standard recommended application rates is expressed on a scale of 1 (resistant), 2 (tolerant), or 3 (susceptible).

DETAILED DESCRIPTION

AGR044-312D and AGR044-3A22 are inbred *Brassica carinata* varieties that has been selected on the basis of improved yield relative to existing commercial *carinata* varieties (eg A110 and A120). Other improvements relative to existing commercial *carinata* varieties may include: reduced levels of seed glucosinolate, improved disease resistance, reduced tendency to lodging and pod shatter.

In some embodiments, the present invention provides methods, uses, and compositions of matter related to the cells, seeds, plants or parts thereof, derivative seeds, and derivative plants of *Brassica carinata* cultivars AGR044-312D and AGR044-3A22.

In the embodiments described below, "essentially all of the physiological and morphological characteristics" can mean, for example, the quantitative physiological and morphological characteristics described in Tables 1 and 3-7 for AGR044-3A22 or in Tables 1, 2, and 14 for AGR044-312D when grown in the same location under the same environmental conditions, as determined at the 5% significance level.

In the embodiments described below, "essentially all of the physiological and morphological characteristics" can also mean the quantitative physiological and morphological characteristics described in Tables 1, 3, and 5-7 for AGR044-3A22 or in Tables 1, 2, 5-10, and 12-14 for AGR044-312D when grown in the same location under the same environmental conditions, as determined at the 5% significance level.

5.1 AGR044-312D 5.1.1 Seeds, Plants, Plant Parts and Cells

In one embodiment, the invention provides a seed of *Brassica carinata* cultivar designated AGR044-312D, wherein a representative sample of the seed has been deposited under ATCC Accession number PTA-123015.

In another embodiment, the invention provides a plant of *Brassica carinata* cultivar AGR044-312D, or a part thereof, produced from the seed of *Brassica carinata* cultivar designated AGR044-312D, wherein a representative sample of the seed has been deposited under ATCC Accession number PTA-123015.

In another embodiment, the invention provides a plant part of *Brassica carinata* cultivar AGR044-312D, or a part thereof, produced from the seed of *Brassica carinata* cultivar designated AGR044-312D, wherein a representative sample of the seed has been deposited under ATCC Accession number PTA-123015, wherein the plant part is an ovule, a leaf, pollen, a seed, an embryo a root, a root tip, a pod, a flower, a stalk, a cell, or a protoplast.

In another embodiment, the invention provides a plant part of *Brassica carinata* cultivar AGR044-312D, or a part thereof, produced from the seed of *Brassica carinata* cultivar designated AGR044-312D, wherein a representative sample of the seed has been deposited under ATCC Accession number PTA-123015, wherein the plant part is pollen.

In another embodiment, the invention provides a plant part of *Brassica carinata* cultivar AGR044-312D, or a part thereof, produced from the seed of *Brassica carinata* cultivar designated AGR044-312D, wherein a representative sample of the seed has been deposited under ATCC Accession number PTA-123015, wherein the plant part is an ovule.

In another embodiment, the invention provides a *Brassica carinata* plant, or a part thereof, having essentially all of the physiological and morphological characteristics of a plant of *Brassica carinata* cultivar AGR044-312D produced from the seed of *Brassica carinata* cultivar designated AGR044-312D, wherein a representative sample of the seed has been deposited under ATCC Accession number PTA-123015, when grown in the same location under the same environmental conditions.

In another embodiment, the invention provides a cell of a seed of *Brassica carinata* cultivar designated AGR044-312D, wherein a representative sample of said seed has been deposited under ATCC Accession number PTA-123015.

In another embodiment, the invention provides a cell of a plant of *Brassica carinata* cultivar AGR044-312D, or a part thereof, produced from a seed of *Brassica carinata* cultivar designated AGR044-312D, wherein a representative sample of said seed has been deposited under ATCC Accession number PTA-123015.

In another embodiment, the invention provides a protoplast of a plant of *Brassica carinata* cultivar AGR044-312D, or a part thereof, produced from a seed of *Brassica carinata* cultivar designated AGR044-312D, wherein a representative sample of said seed has been deposited under ATCC Accession number PTA-123015.

In another embodiment, the invention provides a cell of a plant of *Brassica carinata* cultivar AGR044-312D, or a part thereof, produced from a seed of *Brassica carinata* cultivar designated AGR044-312D, wherein a representative sample of said seed has been deposited under ATCC Accession number PTA-123015, wherein the plant part is an ovule, a leaf, pollen, a seed, an embryo a root, a root tip, a pod, a flower, or a stalk.

In another embodiment, the invention provides a cell of a plant of *Brassica carinata* cultivar AGR044-312D, or a part thereof, produced from a seed of *Brassica carinata* cultivar designated AGR044-312D, wherein a representative sample of said seed has been deposited under ATCC Accession number PTA-123015, wherein the plant part is pollen.

In another embodiment, the invention provides a cell of a plant of *Brassica carinata* cultivar AGR044-312D, or a part thereof, produced from a seed of *Brassica carinata* cultivar designated AGR044-312D, wherein a representative sample of said seed has been deposited under ATCC Accession number PTA-123015, wherein the plant part is an ovule.

In another embodiment, the invention provides a cell of a *Brassica carinata* plant, or parts thereof, having essentially all of the physiological and morphological characteristics of a plant of *Brassica carinata* cultivar AGR044-312D produced from a seed of *Brassica carinata* cultivar designated AGR044-312D, wherein a representative sample of said seed has been deposited under ATCC Accession number PTA-123015, when grown in the same location under the same environmental conditions.

5.1.2 Tissue Cultures and Regenerated Plants

In another embodiment, the invention provides a tissue culture of protoplasts or regenerable cells of a plant of *Brassica carinata* cultivar AGR044-312D, or a part thereof, produced from the seed of *Brassica carinata* cultivar designated AGR044-312D, wherein a representative sample of the seed has been deposited under ATCC Accession number PTA-123015.

In another embodiment, the invention provides a tissue culture of protoplasts or regenerable cells of a plant of *Brassica carinata* cultivar AGR044-312D, or a part thereof, produced from the seed of *Brassica carinata* cultivar designated AGR044-312D, wherein a representative sample of the seed has been deposited under ATCC Accession number PTA-123015, wherein the protoplasts or regenerable cells are produced from a tissue selected from the group consisting of leaves, pollen, embryos, roots, root tips, pods, flowers, ovules, and stalks.

In another embodiment, the invention provides a *Brassica carinata* plant regenerated from a tissue culture of protoplasts or regenerable cells of a plant of *Brassica carinata* cultivar AGR044-312D, or a part thereof, produced from the seed of *Brassica carinata* cultivar designated AGR044-312D, wherein a representative sample of the seed has been deposited under ATCC Accession number PTA-123015, wherein the plant has essentially all of the morphological and physiological characteristics of cultivar AGR044-312D, the seed of which has been deposited under ATCC Accession number PTA-123015, when grown in the same location under the same environmental conditions.

In another embodiment, the invention provides a *Brassica carinata* plant regenerated from a tissue culture of protoplasts or regenerable cells of a plant of *Brassica carinata* cultivar AGR044-312D, or a part thereof, produced from the seed of *Brassica carinata* cultivar designated AGR044-312D, wherein a representative sample of the seed has been deposited under ATCC Accession number PTA-123015, wherein the protoplasts or regenerable cells are produced from a tissue selected from the group consisting of leaves, pollen, embryos, roots, root tips, pods, flowers, ovules, and stalks, wherein the plant has essentially all of the morphological and physiological characteristics of cultivar AGR044-312D, the seed of which has been deposited under ATCC Accession number PTA-123015, when grown in the same location under the same environmental conditions.

In another embodiment, the invention provides a regenerated *Brassica carinata* plant having essentially all of the physiological and morphological characteristics of the cultivar AGR044-312D when grown in the same location under the same environmental conditions, the regenerated plant having been produced using a tissue culture, wherein the tissue culture is produced from a plant of *Brassica carinata* cultivar AGR044-312D, or a part thereof, produced from the seed of *Brassica carinata* cultivar designated AGR044-312D, wherein a representative sample of the seed has been deposited under ATCC Accession number PTA-123015.

In another embodiment, the invention provides a cell of a *Brassica carinata* plant regenerated from a tissue culture of protoplasts or regenerable cells of a plant of *Brassica carinata* cultivar AGR044-312D, or a part thereof, produced from the seed of *Brassica carinata* cultivar designated AGR044-312D, wherein a representative sample of the seed has been deposited under ATCC Accession number PTA-123015, wherein the plant has essentially all of the morphological and physiological characteristics of cultivar AGR044-312D, the seed of which has been deposited under ATCC Accession number PTA-123015, when grown in the same location under the same environmental conditions.

In another embodiment, the invention provides a cell of a *Brassica carinata* plant regenerated from a tissue culture of protoplasts or regenerable cells of a plant of *Brassica carinata* cultivar AGR044-312D, or a part thereof, produced from the seed of *Brassica carinata* cultivar designated AGR044-312D, wherein a representative sample of the seed has been deposited under ATCC Accession number PTA-123015, wherein the protoplasts or regenerable cells are produced from a tissue selected from the group consisting of leaves, pollen, embryos, roots, root tips, pods, flowers, ovules, and stalks, wherein the plant has essentially all of the morphological and physiological characteristics of cultivar AGR044-312D, the seed of which has been deposited under ATCC Accession number PTA-123015, when grown in the same location under the same environmental conditions.

In another embodiment, the invention provides a cell of a regenerated *Brassica carinata* plant having essentially all of the physiological and morphological characteristics of the cultivar AGR044-312D when grown in the same location under the same environmental conditions, the regenerated plant having been produced using a tissue culture, wherein the tissue culture is produced from a plant of *Brassica carinata* cultivar AGR044-312D, or a part thereof, produced from the seed of *Brassica carinata* cultivar designated AGR044-312D, wherein a representative sample of the seed has been deposited under ATCC Accession number PTA-123015.

5.1.3 Methods of Crossing and Uses for Crossing *Brassica carinata* Plants, and the Cells and Seeds Produced Therefrom In another embodiment, the invention provides a method for producing *Brassica carinata* seed comprising crossing *Brassica carinata* plants and harvesting the resulting *Brassica carinata* seed, wherein at least one *Brassica carinata* plant is a plant of *Brassica carinata* cultivar AGR044-312D produced from the seed of *Brassica carinata* cultivar designated AGR044-312D, wherein a representative sample of the seed has been deposited under ATCC Accession number PTA-123015.

In another embodiment, the invention provides a *Brassica carinata* seed produced by a method for producing *Brassica carinata* seed comprising crossing *Brassica carinata* plants and harvesting the resulting *Brassica carinata* seed, wherein at least one *Brassica carinata* plant is a plant of *Brassica carinata* cultivar AGR044-312D produced from the seed of *Brassica carinata* cultivar designated AGR044-312D, wherein a representative sample of the seed has been deposited under ATCC Accession number PTA-123015.

In another embodiment, the invention provides a cell of a *Brassica carinata* seed produced by a method for producing *Brassica carinata* seed comprising crossing *Brassica carinata* plants and harvesting the resulting *Brassica carinata* seed, wherein at least one *Brassica carinata* plant is a plant of *Brassica carinata* cultivar AGR044-312D produced from the seed of *Brassica carinata* cultivar designated AGR044-312D, wherein a representative sample of the seed has been deposited under ATCC Accession number PTA-123015.

In another embodiment, the invention provides use of a plant of *Brassica carinata* cultivar AGR044-312D, wherein a representative sample of said seed has been deposited under ATCC Accession number PTA-123015, to produce seed, wherein the seed is produced by self-fertilization or cross-fertilization.

5.1.4 Methods of and Uses for Producing an F1 Hybrid *Brassica carinata* Seed, and the Cells, Seeds and Plants Produced Therefrom In another embodiment, the invention provides a method for producing a first generation (F1) hybrid *Brassica carinata* seed comprising crossing a plant of *Brassica carinata* cultivar AGR044-312D produced from the seed of *Brassica carinata* cultivar designated AGR044-312D, wherein a representative sample of the seed has been deposited under ATCC Accession number PTA-123015, with a different *Brassica carinata* plant and harvesting the resultant F1 hybrid *carinata* seed, and wherein the plant of *Brassica carinata* cultivar AGR044-312D produced from the seed of *Brassica carinata* cultivar designated AGR044-312D is either a female parent or a male parent.

In another embodiment, the invention provides a method for producing a first generation (F1) hybrid *Brassica carinata* seed comprising crossing a plant of *Brassica carinata* cultivar AGR044-312D produced from the seed of *Brassica carinata* cultivar designated AGR044-312D, wherein a representative sample of the seed has been deposited under ATCC Accession number PTA-123015, with a different *Brassica carinata* plant and harvesting the resultant F1 hybrid *carinata* seed, and wherein the plant of *Brassica carinata* cultivar AGR044-312D produced from the seed of *Brassica carinata* cultivar designated AGR044-312D is the female parent.

In another embodiment, the invention provides a method for producing a first generation (F1) hybrid *Brassica carinata* seed comprising crossing a plant of *Brassica carinata* cultivar AGR044-312D produced from the seed of *Brassica carinata* cultivar designated AGR044-312D, wherein a representative sample of the seed has been deposited under ATCC Accession number PTA-123015, with a different *Brassica carinata* plant and harvesting the resultant F1 hybrid *carinata* seed, and wherein the plant of *Brassica carinata* cultivar AGR044-312D produced from the seed of *Brassica carinata* cultivar designated AGR044-312D is the male parent.

In another embodiment, the invention provides an F1 hybrid seed produced by a method comprising crossing a plant of *Brassica carinata* cultivar AGR044-312D produced from the seed of *Brassica carinata* cultivar designated AGR044-312D, wherein a representative sample of the seed has been deposited under ATCC Accession number PTA-123015, with a different *Brassica carinata* plant and harvesting the resultant F1 hybrid *carinata* seed, and wherein the plant of *Brassica carinata* cultivar AGR044-312D produced from the seed of *Brassica carinata* cultivar designated AGR044-312D is either a female parent or a male parent.

In another embodiment, the invention provides an F1 hybrid seed produced by a method comprising crossing a plant of *Brassica carinata* cultivar AGR044-312D produced from the seed of *Brassica carinata* cultivar designated AGR044-312D, wherein a representative sample of the seed has been deposited under ATCC Accession number PTA-123015, with a different *Brassica carinata* plant and harvesting the resultant F1 hybrid *carinata* seed, and wherein the plant of *Brassica carinata* cultivar AGR044-312D produced from the seed of *Brassica carinata* cultivar designated AGR044-312D is the female parent.

In another embodiment, the invention provides an F1 hybrid seed produced by a method comprising crossing a plant of *Brassica carinata* cultivar AGR044-312D produced from the seed of *Brassica carinata* cultivar designated AGR044-312D, wherein a representative sample of the seed has been deposited under ATCC Accession number PTA-123015, with a different *Brassica carinata* plant and harvesting the resultant F1 hybrid *carinata* seed, and wherein the plant of *Brassica carinata* cultivar AGR044-312D produced from the seed of *Brassica carinata* cultivar designated AGR044-312D is the male parent.

In another embodiment, the invention provides an F1 hybrid plant grown from an F1 hybrid seed produced by a method comprising crossing a plant of *Brassica carinata* cultivar AGR044-312D produced from the seed of *Brassica carinata* cultivar designated AGR044-312D, wherein a representative sample of the seed has been deposited under ATCC Accession number PTA-123015, with a different *Brassica carinata* plant and harvesting the resultant F1 hybrid *carinata* seed, and wherein the plant of *Brassica carinata* cultivar AGR044-312D produced from the seed of *Brassica carinata* cultivar designated AGR044-312D is either a female parent or a male parent.

In another embodiment, the invention provides an F1 hybrid plant grown from an F1 hybrid seed produced by a method comprising crossing a plant of *Brassica carinata* cultivar AGR044-312D produced from the seed of *Brassica carinata* cultivar designated AGR044-312D, wherein a representative sample of the seed has been deposited under ATCC Accession number PTA-123015, with a different

*Brassica carinata* plant and harvesting the resultant F1 hybrid *carinata* seed, and wherein the plant of *Brassica carinata* cultivar AGR044-312D produced from the seed of *Brassica carinata* cultivar designated AGR044-312D is the female parent.

In another embodiment, the invention provides an F1 hybrid plant grown from an F1 hybrid seed produced by a method comprising crossing a plant of *Brassica carinata* cultivar AGR044-312D produced from the seed of *Brassica carinata* cultivar designated AGR044-312D, wherein a representative sample of the seed has been deposited under ATCC Accession number PTA-123015, with a different *Brassica carinata* plant and harvesting the resultant F1 hybrid *carinata* seed, and wherein the plant of *Brassica carinata* cultivar AGR044-312D produced from the seed of *Brassica carinata* cultivar designated AGR044-312D is the male parent.

In another embodiment, the invention provides use of a plant of *Brassica carinata* cultivar AGR044-312D, wherein a representative sample of said seed has been deposited under ATCC Accession number PTA-123015 to produce an F1 hybrid *Brassica carinata* seed, wherein the plant is either a female parent or a male parent in a cross-fertilization.

In another embodiment, the invention provides use of a plant of *Brassica carinata* cultivar AGR044-312D, wherein a representative sample of said seed has been deposited under ATCC Accession number PTA-123015 to produce an F1 hybrid *Brassica carinata* seed, wherein the plant is the female parent.

In another embodiment, the invention provides use of a plant of *Brassica carinata* cultivar AGR044-312D, wherein a representative sample of said seed has been deposited under ATCC Accession number PTA-123015 to produce an F1 hybrid *Brassica carinata* seed, wherein the plant is the male parent.

In another embodiment, the invention provides a cell of an F1 hybrid plant grown from the F1 hybrid seed produced by any of the above uses.

In another embodiment, the invention provides a cell of an F1 hybrid plant grown from F1 hybrid seed produced by a method comprising crossing a plant of *Brassica carinata* cultivar AGR044-312D, wherein a representative sample of said seed has been deposited under ATCC Accession number PTA-123015, with a different *Brassica carinata* plant and harvesting the resultant F1 hybrid *carinata* seed.

5.1.5 Methods of and Uses for Producing a Doubled Haploidy Variety, and the Cells, Seeds, and Plants Produced Therefrom In another embodiment, the invention provides a method for producing a Doubled Haploidy variety comprising: (a) isolating a flower bud of an F1 hybrid plant grown from an F1 hybrid seed produced by a method comprising crossing a plant of *Brassica carinata* cultivar AGR044-312D produced from the seed of *Brassica carinata* cultivar designated AGR044-312D, wherein a representative sample of the seed has been deposited under ATCC Accession number PTA-123015, with a different *Brassica carinata* plant and harvesting the resultant F1 hybrid *carinata* seed, and wherein the plant of *Brassica carinata* cultivar AGR044-312D produced from the seed of *Brassica carinata* cultivar designated AGR044-312D is either a female parent or a male parent; (b) dissecting out a haploid microspore; (c) placing the haploid microspore in culture; (d) inducing the microspore to differentiate into an embryo and subsequently into a plantlet; (e) identifying whether the plantlet contains a diploid chromosome number, wherein the diploid chromosome number occured through chromosome doubling; and (f) continuing to grow the plantlet if it contains a diploid chromosome number.

In another embodiment, the invention provides a method for producing a Doubled Haploidy variety comprising: (a) isolating a flower bud of an F1 hybrid plant grown from an F1 hybrid seed produced by a method comprising crossing a plant of *Brassica carinata* cultivar AGR044-312D produced from the seed of *Brassica carinata* cultivar designated AGR044-312D, wherein a representative sample of the seed has been deposited under ATCC Accession number PTA-123015, with a different *Brassica carinata* plant and harvesting the resultant F1 hybrid *carinata* seed, and wherein the plant of *Brassica carinata* cultivar AGR044-312D produced from the seed of *Brassica carinata* cultivar designated AGR044-312D is the female parent; (b) dissecting out a haploid microspore; (c) placing the haploid microspore in culture; (d) inducing the microspore to differentiate into an embryo and subsequently into a plantlet; (e) identifying whether the plantlet contains a diploid chromosome number, wherein the diploid chromosome number occured through chromosome doubling; and (f) continuing to grow the plantlet if it contains a diploid chromosome number.

In another embodiment, the invention provides a method for producing a Doubled Haploidy variety comprising: (a) isolating a flower bud of an F1 hybrid plant grown from an F1 hybrid seed produced by a method comprising crossing a plant of *Brassica carinata* cultivar AGR044-312D produced from the seed of *Brassica carinata* cultivar designated AGR044-312D, wherein a representative sample of the seed has been deposited under ATCC Accession number PTA-123015, with a different *Brassica carinata* plant and harvesting the resultant F1 hybrid *carinata* seed, and wherein the plant of *Brassica carinata* cultivar AGR044-312D produced from the seed of *Brassica carinata* cultivar designated AGR044-312D is the male parent; (b) dissecting out a haploid microspore; (c) placing the haploid microspore in culture; (d) inducing the microspore to differentiate into an embryo and subsequently into a plantlet; (e) identifying whether the plantlet contains a diploid chromosome number, wherein the diploid chromosome number occured through chromosome doubling; and (f) continuing to grow the plantlet if it contains a diploid chromosome number.

In another embodiment, the invention provides a method for producing a Doubled Haploidy variety comprising: (a) isolating a flower bud of an F1 hybrid plant grown from an F1 hybrid seed produced by a method comprising crossing a plant of *Brassica carinata* cultivar AGR044-312D produced from the seed of *Brassica carinata* cultivar designated AGR044-312D, wherein a representative sample of the seed has been deposited under ATCC Accession number PTA-123015, with a different *Brassica carinata* plant and harvesting the resultant F1 hybrid *carinata* seed, and wherein the plant of *Brassica carinata* cultivar AGR044-312D produced from the seed of *Brassica carinata* cultivar designated AGR044-312D is either a female parent or a male parent; (b) dissecting out a haploid microspore; (c) placing the haploid microspore in culture; (d) inducing the microspore to differentiate into an embryo and subsequently into a plantlet; (e) identifying whether the plantlet contains a diploid chromosome number, wherein the diploid chromosome number occured through chromosome doubling; and (f) continuing to grow the plantlet if it contains a diploid chromosome number; wherein the method further comprises inducing chromosome doubling by chemical or physical means.

In another embodiment, the invention provides a method for producing a Doubled Haploidy variety comprising: (a)

isolating a flower bud of an F1 hybrid plant grown from an F1 hybrid seed produced by a method comprising crossing a plant of *Brassica carinata* cultivar AGR044-312D produced from the seed of *Brassica carinata* cultivar designated AGR044-312D, wherein a representative sample of the seed has been deposited under ATCC Accession number PTA-123015, with a different *Brassica carinata* plant and harvesting the resultant F1 hybrid *carinata* seed, and wherein the plant of *Brassica carinata* cultivar AGR044-312D produced from the seed of *Brassica carinata* cultivar designated AGR044-312D is the female parent; (b) dissecting out a haploid microspore; (c) placing the haploid microspore in culture; (d) inducing the microspore to differentiate into an embryo and subsequently into a plantlet; (e) identifying whether the plantlet contains a diploid chromosome number, wherein the diploid chromosome number occured through chromosome doubling; and (f) continuing to grow the plantlet if it contains a diploid chromosome number; wherein the method further comprises inducing chromosome doubling by chemical or physical means.

In another embodiment, the invention provides a method for producing a Doubled Haploidy variety comprising: (a) isolating a flower bud of an F1 hybrid plant grown from an F1 hybrid seed produced by a method comprising crossing a plant of *Brassica carinata* cultivar AGR044-312D produced from the seed of *Brassica carinata* cultivar designated AGR044-312D, wherein a representative sample of the seed has been deposited under ATCC Accession number PTA-123015, with a different *Brassica carinata* plant and harvesting the resultant F1 hybrid *carinata* seed, and wherein the plant of *Brassica carinata* cultivar AGR044-312D produced from the seed of *Brassica carinata* cultivar designated AGR044-312D is the male parent; (b) dissecting out a haploid microspore; (c) placing the haploid microspore in culture; (d) inducing the microspore to differentiate into an embryo and subsequently into a plantlet; (e) identifying whether the plantlet contains a diploid chromosome number, wherein the diploid chromosome number occured through chromosome doubling; and (f) continuing to grow the plantlet if it contains a diploid chromosome number; wherein the method further comprises inducing chromosome doubling by chemical or physical means.

In another embodiment, the invention provides a plant, or part thereof, or seed of a Doubled Haploidy variety produced by any of the above methods.

In another embodiment, the invention provides use of a plant of *Brassica carinata* cultivar AGR044-312D, wherein a representative sample of said seed has been deposited under ATCC Accession number PTA-123015 to produce a Doubled Haploidy variety.

In another embodiment, the invention provides use of a plant of *Brassica carinata* cultivar AGR044-312D, wherein a representative sample of said seed has been deposited under ATCC Accession number PTA-123015 to produce a Doubled Haploidy variety, wherein chromosome doubling is introduced by chemical or physical means.

In another embodiment, the invention provides a cell of a Doubled Haploidy variety produced from *Brassica carinata* cultivar AGR044-312D, wherein a representative sample of the seed has been deposited under ATCC Accession number PTA-123015.

In another embodiment, the invention provides use of a plant of a *Brassica carinata* variety produced from *Brassica carinata* cultivar AGR044-312D, wherein a representative sample of said seed has been deposited under ATCC Accession number PTA-123015, to produce a Doubled Haploidy variety.

In another embodiment, the invention provides use of a plant of a *Brassica carinata* variety produced from *Brassica carinata* cultivar AGR044-312D, wherein a representative sample of said seed has been deposited under ATCC Accession number PTA-123015, to produce a Doubled Haploidy variety, wherein chromosome doubling is introduced by chemical or physical means.

5.1.6 Desired Traits

In one aspect, the present invention includes the introduction of a desired trait into *Brassica carinata* cultivar AGR044-312D, wherein a representative sample of the seed has been deposited under ATCC Accession number PTA-123015, to produce a *Brassica carinata* variety comprising the desired trait.

Examples of potential desired traits include
a. cytoplasmic male sterility, CMS restorer traits,
b. biotic and abiotic stress resistance such as disease resistance, fungal resistance, pest resistance, drought tolerance, and frost tolerance,
c. agronomic traits such as increased pod shatter resistance, improved harvestability, improved nutrient usage efficiency, seed colour seed size, seed pod size, seed pod architecture, seed pod fill. earlier and more uniform time to flowering, earlier maturity, extent of branching, flower colour and density, and plant height,
d. altered metabolism (increased seed oil, increased seed protein, altered seed oil or fatty acid profile, reduced seed content of glucosinolates and other antinutritionals),
e. improved performance: improved oil per unit area, improved grain per unit area,
f. herbicide tolerance including tolerance to glyphosate, glufosinate, imidazolinones and auxin analogues such as 2,4-D and dicamba.

5.1.7 Methods of and Uses for Introducing a Desired Trait by Crossing and Backcrossing, and the Cells, Seeds and Plants Produced Therefrom In another embodiment, the invention provides a method of producing a *Brassica carinata* variety produced from a plant of *Brassica carinata* cultivar AGR044-312D produced from the seed of *Brassica carinata* cultivar designated AGR044-312D, wherein a representative sample of the seed has been deposited under ATCC Accession number PTA-123015, and wherein the *Brassica carinata* variety comprises a desired trait, the method comprising the steps of: (a) crossing a plant of cultivar AGR044-312D with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-312D to produce backcross progeny seed; and (d) growing the resultant backcross progeny seed and selecting backcross progeny plants that have the desired trait to produce the *Brassica carinata* variety produced from cultivar AGR044-312D.

In another embodiment, the invention provides a method of producing a *Brassica carinata* variety produced from a plant of *Brassica carinata* cultivar AGR044-312D produced from the seed of *Brassica carinata* cultivar designated AGR044-312D, wherein a representative sample of the seed has been deposited under ATCC Accession number PTA-123015, and wherein the *Brassica carinata* variety comprises a desired trait, the method comprising the steps of: (a) crossing a plant of cultivar AGR044-312D with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-312D to produce backcross progeny seed; and (d) growing the resultant backcross progeny seed and selecting backcross progeny plants that have the desired trait to produce the *Brassica carinata* variety produced from cultivar AGR044-312D; wherein steps (c) and (d) are repeated until the *Brassica carinata* variety produced from cultivar AGR044-312D has the desired trait and essentially all of the physiological and morphological characteristics of cultivar AGR044-312D when grown in the same location under the same environmental conditions.

In another embodiment, the invention provides a method of producing a *Brassica carinata* variety produced from a plant of *Brassica carinata* cultivar AGR044-312D produced from the seed of *Brassica carinata* cultivar designated AGR044-312D, wherein a representative sample of the seed has been deposited under ATCC Accession number PTA-123015, and wherein the *Brassica carinata* variety comprises a desired trait, the method comprising the steps of: (a) crossing a plant of cultivar AGR044-312D with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-312D to produce backcross progeny seed; and (d) growing the resultant backcross progeny seed and selecting backcross progeny plants that have the desired trait to produce the *Brassica carinata* variety produced from cultivar AGR044-312D; and wherein the desired trait is selected from the group consisting of male sterility, disease resistance, fungal resistance, pest resistance, herbicide tolerance, abiotic stress tolerance, and altered metabolism.

In another embodiment, the invention provides a method of producing a *Brassica carinata* variety produced from a plant of *Brassica carinata* cultivar AGR044-312D produced from the seed of *Brassica carinata* cultivar designated AGR044-312D, wherein a representative sample of the seed has been deposited under ATCC Accession number PTA-123015, and wherein the *Brassica carinata* variety comprises a desired trait, the method comprising the steps of: (a) crossing a plant of cultivar AGR044-312D with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-312D to produce backcross progeny seed; and (d) growing the resultant backcross progeny seed and selecting backcross progeny plants that have the desired trait to produce the *Brassica carinata* variety produced from cultivar AGR044-312D; wherein steps (c) and (d) are repeated until the *Brassica carinata* variety produced from cultivar AGR044-312D has the desired trait and essentially all of the physiological and morphological characteristics of cultivar AGR044-312D when grown in the same location under the same environmental conditions; and wherein the desired trait is selected from the group consisting of male sterility, disease resistance, fungal resistance, pest resistance, herbicide tolerance, abiotic stress tolerance, and altered metabolism.

In another embodiment, the invention provides a method of producing a *Brassica carinata* variety produced from a plant of *Brassica carinata* cultivar AGR044-312D produced from the seed of *Brassica carinata* cultivar designated AGR044-312D, wherein a representative sample of the seed has been deposited under ATCC Accession number PTA-123015, and wherein the *Brassica carinata* variety comprises a desired trait, the method comprising the steps of: (a) crossing a plant of cultivar AGR044-312D with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-312D to produce backcross progeny seed; and (d) growing the resultant backcross progeny seed and selecting backcross progeny plants that have the desired trait to produce the *Brassica carinata* variety produced from cultivar AGR044-312D; and wherein the desired trait is herbicide tolerance and the tolerance is conferred to a herbicide selected from but not limited to the group consisting of glyphosate, glufosinate, imidazolinones, auxin analogues such as 2,4-D and dicamba.

In another embodiment, the invention provides a method of producing a *Brassica carinata* variety produced from a plant of *Brassica carinata* cultivar AGR044-312D produced from the seed of *Brassica carinata* cultivar designated AGR044-312D, wherein a representative sample of the seed has been deposited under ATCC Accession number PTA-123015, and wherein the *Brassica carinata* variety comprises a desired trait, the method comprising the steps of: (a) crossing a plant of cultivar AGR044-312D with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-312D to produce backcross progeny seed; and (d) growing the resultant backcross progeny seed and selecting backcross progeny plants that have the desired trait to produce the *Brassica carinata* variety produced from cultivar AGR044-312D; wherein steps (c) and (d) are repeated until the *Brassica carinata* variety produced from cultivar AGR044-312D has the desired trait and essentially all of the physiological and morphological characteristics of cultivar AGR044-312D when grown in the same location under the same environmental conditions; and wherein the desired trait is herbicide tolerance and the tolerance is conferred to a herbicide selected from but not limited to the group consisting of glyphosate, glufosinate, imidazolinones, auxin analogues such as 2,4-D and dicamba.

In another embodiment, the invention provides a plant, or part thereof, or seed of a *Brassica carinata* variety produced by any of the above methods.

In another embodiment, the invention provides use of a plant of *Brassica carinata* cultivar AGR044-312D, wherein a representative sample of said seed has been deposited under ATCC Accession number PTA-123015, to produce a *Brassica carinata* variety comprising a desired trait.

In another embodiment, the invention provides use of a plant of *Brassica carinata* cultivar AGR044-312D, wherein a representative sample of said seed has been deposited under ATCC Accession number PTA-123015, to produce a *Brassica carinata* variety comprising a desired trait, wherein the desired trait is selected from the group consisting of male sterility, disease resistance, fungal resistance, pest resistance, herbicide tolerance, abiotic stress tolerance, and altered metabolism.

In another embodiment, the invention provides use of a plant of *Brassica carinata* cultivar AGR044-312D, wherein a representative sample of said seed has been deposited under ATCC Accession number PTA-123015, to produce a *Brassica carinata* variety comprising a desired trait, wherein the desired trait is herbicide tolerance and the tolerance is conferred to a herbicide selected from but not limited to the group consisting of glyphosate, glufosinate, imidazolinones, and auxin analogues such as 2,4-D and dicamba.

In another embodiment, the invention provides a cell of a plant of a *Brassica carinata* variety produced from *Brassica carinata* cultivar AGR044-312D, wherein a representative sample of said seed has been deposited under ATCC Accession number PTA-123015, wherein the *Brassica carinata* variety comprises a desired trait, and wherein the *Brassica carinata* variety is produced by a method comprising the steps of: (a) crossing a plant of cultivar AGR044-312D with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-312D to produce backcross progeny plants; and (d) growing the resultant backcross progeny seed and selecting backcross progeny plants that have the desired trait to produce the *Brassica carinata* variety produced from cultivar AGR044-312D.

In another embodiment, the invention provides a cell of a plant of a *Brassica carinata* variety produced from *Brassica carinata* cultivar AGR044-312D, wherein a representative sample of said seed has been deposited under ATCC Accession number PTA-123015, wherein the variety comprises a desired trait, and wherein the *Brassica carinata* variety is produced by a method comprising the steps of: (a) crossing a plant of cultivar AGR044-312D with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-312D to produce backcross progeny plants; and (d) growing the resultant backcross progeny seed and selecting backcross progeny plants that have the desired trait to produce the *Brassica carinata* variety produced from cultivar AGR044-312D; wherein the method to produce the *Brassica carinata* variety further comprises repeating steps (c) and (d) until the *Brassica carinata* variety produced from cultivar AGR044-312D has the desired trait and essentially all of the physiological and morphological characteristics of cultivar AGR044-312D when grown in the same location under the same environmental conditions.

In another embodiment, the invention provides a cell of a plant of a *Brassica carinata* variety produced from *Brassica carinata* cultivar AGR044-312D, wherein a representative sample of said seed has been deposited under ATCC Accession number PTA-123015, wherein the *Brassica carinata* variety comprises a desired trait, and wherein the *Brassica carinata* variety is produced by a method comprising the steps of: (a) crossing a plant of cultivar AGR044-312D with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-312D to produce backcross progeny plants; and (d) growing the resultant backcross progeny seed and selecting backcross progeny plants that have the desired trait to produce the *Brassica carinata* variety produced from cultivar AGR044-312D; wherein the desired trait is selected from the group consisting of male sterility, disease resistance, fungal resistance, pest resistance, herbicide tolerance, abiotic stress tolerance, and altered metabolism.

In another embodiment, the invention provides a cell of a plant of a *Brassica carinata* variety produced from *Brassica carinata* cultivar AGR044-312D, wherein a representative sample of said seed has been deposited under ATCC Accession number PTA-123015, wherein the *Brassica carinata* variety comprises a desired trait, and wherein the *Brassica carinata* variety is produced by a method comprising the steps of: (a) crossing a plant of cultivar AGR044-312D with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-312D to produce backcross progeny plants; and (d) growing the resultant backcross progeny seed and selecting backcross progeny plants that have the desired trait to produce the *Brassica carinata* variety produced from cultivar AGR044-312D; wherein the method to produce the *Brassica carinata* variety further comprises repeating steps (c) and (d) until the *Brassica carinata* variety produced from cultivar AGR044-312D has the desired trait and essentially all of the physiological and morphological characteristics of cultivar AGR044-312D when grown in the same location under the same environmental conditions, and wherein the desired trait is selected from the group consisting of male sterility, disease resistance, fungal resistance, pest resistance, herbicide tolerance, abiotic stress tolerance, and altered metabolism.

In another embodiment, the invention provides a cell of a plant of a *Brassica carinata* variety produced from *Brassica carinata* cultivar AGR044-312D, wherein a representative sample of said seed has been deposited under ATCC Accession number PTA-123015, wherein the *Brassica carinata* variety comprises a desired trait, and wherein the *Brassica carinata* variety is produced by a method comprising the steps of: (a) crossing a plant of cultivar AGR044-312D with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-312D to produce backcross progeny plants; and (d) growing the resultant backcross progeny seed and selecting backcross progeny plants that have the desired trait to produce the *Brassica carinata* variety produced from cultivar AGR044-312D, wherein the desired trait is herbicide tolerance and the tolerance is conferred to a herbicide selected from but not limited to the group consisting of glyphosate, glufosinate, imidazolinones, and auxin analogues such as 2,4-D and dicamba.

In another embodiment, the invention provides a cell of a plant of a *Brassica carinata* variety produced from *Brassica carinata* cultivar AGR044-312D, wherein a representative sample of said seed has been deposited under ATCC Accession number PTA-123015, wherein the *Brassica carinata* variety comprises a desired trait, and wherein the *Brassica carinata* variety is produced by a method comprising the steps of: (a) crossing a plant of cultivar AGR044-312D with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-312D to produce backcross progeny plants; and (d) growing the resultant backcross progeny seed and selecting backcross progeny plants that have the desired trait to produce the *Brassica carinata* variety produced from cultivar AGR044-312D; wherein the method to produce the *Brassica carinata* variety further comprises repeating steps (c) and (d) until the *Brassica carinata* variety produced from cultivar AGR044-312D has the desired trait and essentially all of the physiological and morphological characteristics of cultivar AGR044-312D when grown in the same location under the same environmental conditions, wherein the desired trait is herbicide tolerance and the tolerance is conferred to a herbicide selected from but not limited to the group consisting of glyphosate, glufosinate, imidazolinones, and auxin analogues such as 2,4-D and dicamba.

5.1.8 DNA Constructs

In one aspect, the present invention includes the introduction of a desired trait into *Brassica carinata* cultivar AGR044-312D, wherein a representative sample of the seed has been deposited under ATCC Accession number PTA-123015, to produce a *Brassica carinata* variety comprising the desired trait, wherein the desired trait is conferred by a DNA construct.

The DNA construct can be introduced by a variety of methods, including by using polyethylene glycol (PEG) mediated DNA uptake, electroporation, ballistic infiltration using DNA coated microprojectiles (gene gun), an *Agrobacterium* infiltration based vector, or a plant virus based vector.

The DNA construct can comprise any type of DNA, including a transgene or a DNA construct that is designed to modulate the expression of endogenous genes.

Examples of transgenes that could be incorporated include, but are not limited to, the following group: *Crambe abbysinica* FAE1, *Teesdalia nodulicans* FAE1, *Cardamine graeca* FAE1 *Brassica napus* DGAT, *Tropaeolum majus* DGAT, Yeast SLC1

DNA constructs that are designed to modulate the expression of endogenous genes include, but are not limited to the following group: *Brassica carinata* Myb28, Myb29, FAD2 and FAD3 antisense RNA or RNAi sequences, which can be used to interfere or knock down the expression of endogenous genes to extremely low levels, simulating the effect of a null mutation at the endogenous locus. As discussed above, because *Brassica carinata* is amphidiploid, it can have multiple copies of genes from the contributing ancestral species that may create a high level of functional redundancy. As such, a single mutation in one of the homologues may not be sufficient to confer a phenotype. By using RNAi or an antisense approach, one may conceivably be capable of targeting all of the expressed homologues and achieving a functional knockdown effect. Such approaches require the RNAi or antisense RNA to be stably expressed.

5.1.9 Methods of and Uses for Introducing a Desired Trait Using DNA Constructs, and the Cells, Seeds and Plants Produced Therefrom In another embodiment, the invention provides a method of producing a *Brassica carinata* variety produced from *Brassica carinata* cultivar AGR044-312D, wherein a representative sample of the seed has been deposited under ATCC Accession number PTA-123015, and wherein the *Brassica carinata* variety comprises a desired trait, the method comprising introducing a DNA construct conferring the desired trait into a plant of cultivar AGR044-312D.

In another embodiment, the invention provides a method of producing a *Brassica carinata* variety produced from *Brassica carinata* cultivar AGR044-312D, wherein a representative sample of the seed has been deposited under ATCC Accession number PTA-123015, wherein the *Brassica carinata* variety comprises a desired trait, the method comprising introducing a DNA construct conferring the desired trait into a plant of cultivar AGR044-312D, and wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector.

In another embodiment, the invention provides a method of producing a *Brassica carinata* variety produced from *Brassica carinata* cultivar AGR044-312D, wherein a representative sample of the seed has been deposited under ATCC Accession number PTA-123015, wherein the *Brassica carinata* variety comprises a desired trait, the method comprising introducing a DNA construct conferring the desired trait into a plant of cultivar AGR044-312D, and wherein the DNA construct comprises a transgene.

In another embodiment, the invention provides a method of producing a *Brassica carinata* variety produced from *Brassica carinata* cultivar AGR044-312D, wherein a representative sample of the seed has been deposited under ATCC Accession number PTA-123015, wherein the *Brassica carinata* variety comprises a desired trait, the method comprising introducing a DNA construct conferring the desired trait into a plant of cultivar AGR044-312D, wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector, and wherein the DNA construct comprises a transgene.

In another embodiment, the invention provides a method of producing a *Brassica carinata* variety produced from *Brassica carinata* cultivar AGR044-312D, wherein a representative sample of the seed has been deposited under ATCC Accession number PTA-123015, wherein the *Brassica carinata* variety comprises a desired trait, the method comprising introducing a DNA construct conferring the desired trait into a plant of cultivar AGR044-312D, and wherein the DNA construct comprises an RNAi construct.

In another embodiment, the invention provides a method of producing a *Brassica carinata* variety produced from *Brassica carinata* cultivar AGR044-312D, wherein a representative sample of the seed has been deposited under ATCC Accession number PTA-123015, wherein the *Brassica carinata* variety comprises a desired trait, the method comprising introducing a DNA construct conferring the desired trait into a plant of cultivar AGR044-312D, wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector, and wherein the DNA construct comprises an RNAi construct.

In another embodiment, the invention provides any one of the above methods, wherein the *Brassica carinata* variety comprises the desired trait and essentially all of the physiological and morphological characteristics of cultivar AGR044-312D, when grown in the same location under the same environmental conditions.

In another embodiment, the invention provides any one of the above methods, wherein the desired trait is selected from the group consisting of male sterility, disease resistance, fungal resistance, pest resistance, herbicide tolerance, abiotic stress tolerance, and altered metabolism.

In another embodiment, the invention provides any one of the above methods, wherein the desired trait is herbicide tolerance and the tolerance is conferred to a herbicide selected from but not limited to the group consisting of glyphosate, glufosinate, imidazolinones, and auxin analogues such as 2,4-D and dicamba.

In another embodiment, the invention provides a plant, or part thereof, or seed of a *Brassica carinata* variety produced by any one of the above methods.

In another embodiment, the invention provides use of a plant of *Brassica carinata* cultivar AGR044-312D, wherein a representative sample of said seed has been deposited under ATCC Accession number PTA-123015, to produce a *Brassica carinata* variety comprising a desired trait, wherein the desired trait is conferred by a DNA construct.

In another embodiment, the invention provides use of a plant of *Brassica carinata* cultivar AGR044-312D, wherein a representative sample of said seed has been deposited under ATCC Accession number PTA-123015, to produce a *Brassica carinata* variety comprising a desired trait, wherein the desired trait is conferred by a DNA construct, wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector.

In another embodiment, the invention provides use of a plant of *Brassica carinata* cultivar AGR044-312D, wherein a representative sample of said seed has been deposited under ATCC Accession number PTA-123015, to produce a *Brassica carinata* variety comprising a desired trait, wherein the desired trait is conferred by a DNA construct, and wherein the DNA construct comprises a transgene.

In another embodiment, the invention provides use of a plant of *Brassica carinata* cultivar AGR044-312D, wherein a representative sample of said seed has been deposited under ATCC Accession number PTA-123015, to produce a *Brassica carinata* variety comprising a desired trait, wherein the desired trait is conferred by a DNA construct, wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector, and wherein the DNA construct comprises a transgene.

In another embodiment, the invention provides use of a plant of *Brassica carinata* cultivar AGR044-312D, wherein a representative sample of said seed has been deposited under ATCC Accession number PTA-123015, to produce a *Brassica carinata* variety comprising a desired trait, wherein the desired trait is conferred by a DNA construct, and wherein the DNA construct comprises an RNAi construct.

In another embodiment, the invention provides use of a plant of *Brassica carinata* cultivar AGR044-312D, wherein a representative sample of said seed has been deposited under ATCC Accession number PTA-123015, to produce a *Brassica carinata* variety comprising a desired trait, wherein the desired trait is conferred by a DNA construct, wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector, and wherein the DNA construct comprises an RNAi construct.

In another embodiment, the invention provides any of the above uses, wherein the *Brassica carinata* variety comprises the desired trait and essentially all of the physiological and morphological characteristics of cultivar AGR044-312D when grown in the same location under the same environmental conditions.

In another embodiment, the invention provides any of the above uses, wherein the desired trait is selected from the group consisting of male sterility, disease resistance, fungal resistance, pest resistance, herbicide tolerance, abiotic stress tolerance, and altered metabolism.

In another embodiment, the invention provides any of the above uses, wherein the desired trait is herbicide tolerance and the tolerance is conferred to a herbicide selected from but not limited to the group consisting of glyphosate, glufosinate, imidazolinones, and auxin analogues such as 2,4-D and dicamba.

In another embodiment, the invention provides a cell of a plant of a *Brassica carinata* variety produced from cultivar AGR044-312D, the seed of which has been deposited under ATCC Accession number PTA-123015, wherein the *Brassica carinata* variety comprises a desired trait, and wherein the *Brassica carinata* variety was produced by a method comprising introducing a DNA construct conferring the desired trait into a plant of cultivar AGR044-312D.

In another embodiment, the invention provides a cell of a plant of a *Brassica carinata* variety produced from cultivar AGR044-312D, the seed of which has been deposited under ATCC Accession number PTA-123015, wherein the *Brassica carinata* variety comprises a desired trait, and wherein the *Brassica carinata* variety was produced by a method comprising introducing a DNA construct conferring the desired trait into a plant of cultivar AGR044-312D, wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector.

In another embodiment, the invention provides a cell of a plant of a *Brassica carinata* variety produced from cultivar AGR044-312D, the seed of which has been deposited under ATCC Accession number PTA-123015, wherein the *Brassica carinata* variety comprises a desired trait, and wherein the *Brassica carinata* variety was produced by a method comprising introducing a DNA construct conferring the desired trait into a plant of cultivar AGR044-312D, and wherein the DNA construct comprises a transgene.

In another embodiment, the invention provides a cell of a plant of a *Brassica carinata* variety produced from cultivar AGR044-312D, the seed of which has been deposited under ATCC Accession number PTA-123015, wherein the *Brassica carinata* variety comprises a desired trait, and wherein the *Brassica carinata* variety was produced by a method comprising introducing a DNA construct conferring the desired trait into a plant of cultivar AGR044-312D, wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector, and wherein the DNA construct comprises a transgene.

In another embodiment, the invention provides a cell of a plant of a *Brassica carinata* variety produced from cultivar AGR044-312D, the seed of which has been deposited under ATCC Accession number PTA-123015, wherein the *Brassica carinata* variety comprises a desired trait, and wherein the *Brassica carinata* variety was produced by a method comprising introducing a DNA construct conferring the desired trait into a plant of cultivar AGR044-312D, and wherein the DNA construct comprises an RNAi construct.

In another embodiment, the invention provides a cell of a plant of a *Brassica carinata* variety produced from cultivar AGR044-312D, the seed of which has been deposited under ATCC Accession number PTA-123015, wherein the *Brassica carinata* variety comprises a desired trait, and wherein the *Brassica carinata* variety was produced by a method comprising introducing a DNA construct conferring the desired trait into a plant of cultivar AGR044-312D, wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector, and wherein the DNA construct comprises an RNAi construct.

In another embodiment, the invention provides any of the above cells, wherein the *Brassica carinata* variety comprises the desired trait and essentially all of the physiological and morphological characteristics of cultivar AGR044-312D when grown in the same location under the same environmental conditions.

In another embodiment, the invention provides any of the above cells, wherein the desired trait is selected from the group consisting of male sterility, disease resistance, fungal resistance, pest resistance, herbicide tolerance, abiotic stress tolerance, and altered metabolism.

In another embodiment, the invention provides any of the above cells, wherein the desired trait is herbicide tolerance and the tolerance is conferred to a herbicide selected from but not limited to the group consisting of glyphosate, glufosinate, imidazolinones, and auxin analogues such as 2,4-D and dicamba.

5.1.10 Methods of and Uses for Introducing a Desired Trait by an Initial Cross and then Pedigree Selection, and Cells, Plants and Seeds Produced Therefrom In another embodiment, the invention provides a method of producing a *Brassica carinata* variety produced from *Brassica carinata* cultivar AGR044-312D, wherein a representative sample of the seed has been deposited under ATCC Accession number PTA-123015, and wherein the *Brassica carinata* variety comprises a desired trait, the method comprising the steps of: (a) crossing a plant of cultivar AGR044-312D with another *Brassica carinata* variety comprising the desired trait; (b) growing the resultant F1 hybrid seed and selecting one or more progeny plants that have the desired trait; (c) selfing the progeny plants that have the desired trait to produce further progeny seed; and (d) growing the further progeny seed and selecting further progeny plants that have the desired trait to produce the *Brassica carinata* variety produced from cultivar AGR044-312D.

In another embodiment, the invention provides a method of producing a *Brassica carinata* variety produced from *Brassica carinata* cultivar AGR044-312D, wherein a representative sample of the seed has been deposited under ATCC Accession number PTA-123015, and wherein the *Brassica carinata* variety comprises a desired trait, the method comprising the steps of: (a) crossing a plant of cultivar AGR044-312D with another *Brassica carinata* variety comprising the desired trait; (b) growing the resultant F1 hybrid seed and selecting one or more progeny plants that have the desired trait; (c) selfing the progeny plants that have the desired trait to produce further progeny seed; and (d) growing the further progeny seed and selecting further progeny plants that have the desired trait to produce the *Brassica carinata* variety produced from cultivar AGR044-312D; wherein steps (c) and (d) are repeated until the *Brassica carinata* variety produced from cultivar AGR044-312D has the desired trait and essentially all of the physiological and morphological characteristics of cultivar AGR044-312D when grown in the same location under the same environmental conditions.

In another embodiment, the invention provides any one of the above methods wherein the desired trait is selected from the group consisting of male sterility, disease resistance, fungal resistance, pest resistance, herbicide tolerance, abiotic stress tolerance, and altered metabolism.

In another embodiment, the invention provides any one of the above methods, wherein the desired trait is herbicide tolerance and the tolerance is conferred to a herbicide selected from but not limited to the group consisting of glyphosate, glufosinate, imidazolinones, and auxin analogues such as 2,4-D and dicamba.

In another embodiment, the invention provides a plant, or part thereof, or seed of a *Brassica carinata* variety produced by any one of the above methods.

In another embodiment, the invention provides a cell of a plant of a *Brassica carinata* variety produced from cultivar AGR044-312D, the seed of which has been deposited under ATCC Accession number PTA-123015, wherein the *Brassica carinata* variety comprises a desired trait, and wherein the *Brassica carinata* variety was produced by a method comprising the steps of: (a) crossing a plant of cultivar AGR044-312D with a plant of another *Brassica carinata* variety comprising the desired trait; (b) growing the resultant F1 hybrid seed and selecting one or more progeny plants that have the desired trait; (c) selfing the progeny plants that have the desired trait to produce further progeny plants; and (d) growing the resultant further progeny plants and selecting further progeny plants that have the desired trait to produce the *Brassica carinata* variety produced from cultivar AGR044-312D.

In another embodiment, the invention provides a cell of a plant of a *Brassica carinata* variety produced from cultivar AGR044-312D, the seed of which has been deposited under ATCC Accession number PTA-123015, wherein the *Brassica carinata* variety comprises a desired trait, and wherein the *Brassica carinata* variety was produced by a method comprising the steps of: (a) crossing a plant of cultivar AGR044-312D with a plant of another *Brassica carinata* variety comprising the desired trait; (b) growing the resultant F1 hybrid seed and selecting one or more progeny plants that have the desired trait; (c) selfing the progeny plants that have the desired trait to produce further progeny plants; and (d) growing the resultant further progeny plants and selecting further progeny plants that have the desired trait to produce the *Brassica carinata* variety produced from cultivar AGR044-312D; wherein steps (c) and (d) are repeated until the *Brassica carinata* variety produced from cultivar AGR044-312D has the desired trait and essentially all of the physiological and morphological characteristics of cultivar AGR044-312D when grown in the same location under the same environmental conditions.

In another embodiment, the invention provides a cell of a plant of a *Brassica carinata* variety produced from cultivar AGR044-312D, the seed of which has been deposited under ATCC Accession number PTA-123015, wherein the *Brassica carinata* variety comprises a desired trait, and wherein the *Brassica carinata* variety was produced by a method comprising the steps of: (a) crossing a plant of cultivar AGR044-312D with a plant of another *Brassica carinata* variety comprising the desired trait; (b) growing the resultant F1 hybrid seed and selecting one or more progeny plants that have the desired trait; (c) selfing the progeny plants that have the desired trait to produce further progeny plants; and (d) growing the resultant further progeny plants and selecting further progeny plants that have the desired trait to produce the *Brassica carinata* variety produced from cultivar AGR044-312D; wherein the desired trait is selected from the group consisting of male sterility, disease resistance, fungal resistance, pest resistance, herbicide tolerance, abiotic stress tolerance, and altered metabolism.

In another embodiment, the invention provides a cell of a plant of a *Brassica carinata* variety produced from cultivar AGR044-312D, the seed of which has been deposited under ATCC Accession number PTA-123015, wherein the *Brassica carinata* variety comprises a desired trait, and wherein the *Brassica carinata* variety was produced by a method comprising the steps of: (a) crossing a plant of cultivar AGR044-312D with a plant of another *Brassica carinata* variety comprising the desired trait; (b) growing the resultant F1 hybrid seed and selecting one or more progeny plants that have the desired trait; (c) selfing the progeny plants that have the desired trait to produce further progeny plants; and (d) growing the resultant further progeny plants and selecting further progeny plants that have the desired trait to produce the *Brassica carinata* variety produced from cultivar AGR044-312D; wherein steps (c) and (d) are repeated until the *Brassica carinata* variety produced from cultivar AGR044-312D has the desired trait and essentially all of the physiological and morphological characteristics of cultivar AGR044-312D when grown in the same location under the same environmental conditions, and wherein the desired trait is selected from the group consisting of male sterility, disease resistance, fungal resistance, pest resistance, herbicide tolerance, abiotic stress tolerance, and altered metabolism.

In another embodiment, the invention provides a cell of a plant of a *Brassica carinata* variety produced from cultivar AGR044-312D, the seed of which has been deposited under ATCC Accession number PTA-123015, wherein the *Brassica carinata* variety comprises a desired trait, and wherein the *Brassica carinata* variety was produced by a method comprising the steps of: (a) crossing a plant of cultivar AGR044-312D with a plant of another *Brassica carinata* variety comprising the desired trait; (b) growing the resultant F1 hybrid seed and selecting one or more progeny plants that have the desired trait; (c) selfing the progeny plants that have the desired trait to produce further progeny plants; and (d) growing the resultant further progeny plants and selecting further progeny plants that have the desired trait to produce the *Brassica carinata* variety produced from cultivar AGR044-312D; wherein the desired trait is herbicide tolerance and the tolerance is conferred to a herbicide selected from but not limited to the group consisting of glyphosate, glufosinate, imidazolinones, and auxin analogues such as 2,4-D and dicamba.

In another embodiment, the invention provides a cell of a plant of a *Brassica carinata* variety produced from cultivar AGR044-312D, the seed of which has been deposited under ATCC Accession number PTA-123015, wherein the *Brassica carinata* variety comprises a desired trait, and wherein the *Brassica carinata* variety was produced by a method comprising the steps of: (a) crossing a plant of cultivar AGR044-312D with a plant of another *Brassica carinata* variety comprising the desired trait; (b) growing the resultant F1 hybrid seed and selecting one or more progeny plants that have the desired trait; (c) selfing the progeny plants that have the desired trait to produce further progeny plants; and (d) growing the resultant further progeny plants and selecting further progeny plants that have the desired trait to produce the *Brassica carinata* variety produced from cultivar AGR044-312D; wherein steps (c) and (d) are repeated until the *Brassica carinata* variety produced from cultivar AGR044-312D has the desired trait and essentially all of the physiological and morphological characteristics of cultivar AGR044-312D when grown in the same location under the same environmental conditions; and wherein the desired trait is herbicide tolerance and the tolerance is conferred to a herbicide selected from but not limited to the group consisting of glyphosate, glufosinate, imidazolinones, and auxin analogues such as 2,4-D and dicamba.

5.1.11 Mutagenesis

In one aspect, the present invention includes the introduction of a desired trait into *Brassica carinata* cultivar AGR044-312D, wherein a representative sample of the seed has been deposited under ATCC Accession number PTA-123015, to produce a *Brassica carinata* variety comprising the desired trait, wherein the desired trait is introduced by mutagenesis.

Any means of mutagenesis can potentially be used, including the mutagenic agents ethyl methanesulfonate, N-ethyl-N-nitrosourea, ionizing radiation such as x-ray or gamma, or ultraviolet radiation.

The mutagenization can be of a variety of parts of the plants, including a seed, seedling, or microspore. Mutagenized microspores can then be used to generate doubled haploid plants (see above). Seedlings or microspores are exposed to the mutagenic agent and then the surviving fraction are allowed to develop into mature plants. In some cases, the mutagenized plantlets or embryos (in the case of microspore mutagenesis) may be exposed to selection in order to enrich for a particular phenotype. This technique can be used to develop varieties with a desired trait, such as resistance to a herbicide, an altered seed oil profile, increased tolerance to disease, or abiotic stress.

In another embodiment, the invention provides a method of producing a *Brassica carinata* variety produced from *Brassica carinata* cultivar AGR044-312D, wherein a representative sample of the seed has been deposited under ATCC Accession number PTA-123015, and wherein the *Brassica carinata* variety comprises a desired trait, the method comprising exposing seedlings or microspores to a mutagenic agent and allowing the surviving fraction to develop into mature plants.

In another embodiment, the invention provides a method of producing a *Brassica carinata* variety produced from *Brassica carinata* cultivar AGR044-312D, wherein a representative sample of the seed has been deposited under ATCC Accession number PTA-123015, and wherein the *Brassica carinata* variety comprises a desired trait, the method comprising exposing seedlings or microspores to a mutagenic agent and allowing the surviving fraction to develop into mature plants, and wherein the mutagenic agent is ethyl methanesulfonate, N-ethyl-N-nitrosourea, ionizing radiation such as x-ray or gamma, or ultraviolet radiation.

In another embodiment, the invention provides a plant, or part thereof, or seed of a *Brassica carinata* variety produced by any of the above methods.

In another embodiment, the invention provides use of a plant of *Brassica carinata* cultivar AGR044-312D, wherein a representative sample of said seed has been deposited under ATCC Accession number PTA-123015, to produce a *Brassica carinata* variety comprising a desired trait, wherein the desired trait is introduced by exposing seedlings or microspores to a mutagenic agent.

In another embodiment, the invention provides use of a plant of *Brassica carinata* cultivar AGR044-312D, wherein a representative sample of said seed has been deposited under ATCC Accession number PTA-123015, to produce a *Brassica carinata* variety comprising a desired trait, wherein the desired trait is introduced by exposing seedlings or microspores to a mutagenic agent, and wherein the mutagenic agent is ethyl methanesulfonate, N-ethyl-N-nitrosourea, ionizing radiation such as x-ray or gamma, or ultraviolet radiation.

In another embodiment, the invention provides a cell of a plant of a *Brassica carinata* variety produced from cultivar AGR044-312D, wherein a representative sample of said seed has been deposited under ATCC Accession number PTA-123015, wherein the *Brassica carinata* variety comprises a desired trait, and wherein the *Brassica carinata* variety is produced by a method comprising exposing seedlings or microspores to a mutagenic agent and allowing the surviving fraction to develop into mature plants.

In another embodiment, the invention provides a cell of a plant of a *Brassica carinata* variety produced from cultivar AGR044-312D, wherein a representative sample of said seed has been deposited under ATCC Accession number PTA-123015, wherein the *Brassica carinata* variety comprises a desired trait, and wherein the *Brassica carinata* variety is produced by a method comprising exposing seedlings or microspores to a mutagenic agent and allowing the surviving fraction to develop into mature plants, wherein the mutagenic agent is ethyl methanesulfonate, N-ethyl-N-nitrosourea, ionizing radiation such as x-ray or gamma, or ultraviolet radiation.

5.1.12 Methods of or Uses for Producing a *Carinata* Variety by Outcrossing (Interspecific or Wide Crossing), and Cells, Plants, Seeds Produced Therefrom Where no *Brassica carinata* variety has a specific desired trait, outcrossing (interspecific or wide crossing) can be used where the trait is found in another Brassicaceae species, such as, for example, *Brassica napus, Brassica juncea, Brassica oleracea, Brassica rapa,* or *Brassica nigra.*

In another embodiment, the invention provides a method of producing a *carinata* variety produced from *Brassica carinata* cultivar AGR044-312D, wherein a representative sample of the seed has been deposited under ATCC Accession number PTA-123015, and wherein the *carinata* variety comprises a desired trait, the method comprising: (a) crossing a plant of cultivar AGR044-312D with a plant of another Brassicaceae species comprising the desired trait; (b) using embryo rescue techniques to recover viable F1 plants from the cross or growing F1 seeds to produce F1 plants; (c) selfing the F1 plants that have the desired trait and *carinata* character; (d) using embryo rescue techniques to recover viable F2 plants or growing F2 seeds to produce F2 plants; (e) selfing the F2 plants that have the desired trait and *carinata* character; (f) using embryo rescue techniques to recover viable F3 plants or growing F3 seeds to produce progeny plants; (g) selfing the progeny plants that have the desired trait and *carinata* character to produce further progeny plants; and (h) selecting the progeny plants with the desired trait and *carinata* character to produce the *carinata* variety produced from cultivar AGR044-312D.

In another embodiment, the invention provides a method of producing a *carinata* variety produced from *Brassica carinata* cultivar AGR044-312D, wherein a representative sample of the seed has been deposited under ATCC Accession number PTA-123015, and wherein the *carinata* variety comprises a desired trait, the method comprising: (a) crossing a plant of cultivar AGR044-312D with a plant of another Brassicaceae species comprising the desired trait; (b) using embryo rescue techniques to recover viable F1 plants from the cross or growing F1 seeds to produce F1 plants; (c) selfing the F1 plants that have the desired trait and *carinata* character; (d) using embryo rescue techniques to recover viable F2 plants or growing F2 seeds to produce F2 plants; (e) selfing the F2 plants that have the desired trait and *carinata* character; (f) using embryo rescue techniques to recover viable F3 plants or growing F3 seeds to produce progeny plants; (g) selfing the progeny plants that have the desired trait and *carinata* character to produce further progeny plants; and (h) selecting the progeny plants with the desired trait and *carinata* character to produce the *carinata* variety produced from cultivar AGR044-312D; wherein steps (g) and (h) are repeated until the *carinata* variety produced from cultivar AGR044-312D has the desired trait and essentially all of the physiological and morphological characteristics of cultivar AGR044-312D when grown in the same location under the same environmental conditions.

In another embodiment, the invention provides any of the above methods, wherein the desired trait is selected from the group consisting of male sterility, disease resistance, fungal resistance, pest resistance, herbicide tolerance, abiotic stress tolerance, and altered metabolism.

In another embodiment, the invention provides any of the above methods, wherein the desired trait is herbicide tolerance and the tolerance is conferred to a herbicide selected from but not limited to the group consisting of glyphosate, glufosinate, imidazolinones, and auxin analogues such as 2,4-D and dicamba.

In another embodiment, the invention provides any of the above methods, wherein the method further comprises producing a doubled haploidy variety from the *carinata* variety.

In another embodiment, the invention provides a plant, or part thereof, or seed of a *carinata* variety produced by any of the above methods.

In another embodiment, the invention provides use of a plant of *Brassica carinata* cultivar AGR044-312D, wherein a representative sample of said seed has been deposited under ATCC Accession number PTA-123015, to produce a *carinata* variety comprising a desired trait, wherein the desired trait is introduced by crossing a plant of cultivar AGR044-312D with a plant of another Brassicaceae species comprising the desired trait.

In another embodiment, the invention provides use of a plant of *Brassica carinata* cultivar AGR044-312D, wherein a representative sample of said seed has been deposited under ATCC Accession number PTA-123015, to produce a *carinata* variety comprising a desired trait, wherein the desired trait is introduced by crossing a plant of cultivar AGR044-312D with a plant of another Brassicaceae species comprising the desired trait, and wherein the *carinata* variety produced from cultivar AGR044-312D has the desired trait and essentially all of the physiological and morphological characteristics of cultivar AGR044-312D when grown in the same location under the same environmental conditions.

In another embodiment, the invention provides use of a plant of *Brassica carinata* cultivar AGR044-312D, wherein a representative sample of said seed has been deposited under ATCC Accession number PTA-123015, to produce a *carinata* variety comprising a desired trait, wherein the desired trait is introduced by crossing a plant of cultivar AGR044-312D with a plant of another Brassicaceae species comprising the desired trait, and wherein the desired trait is selected from the group consisting of male sterility, disease resistance, fungal resistance, pest resistance, herbicide tolerance, abiotic stress tolerance, and altered metabolism.

In another embodiment, the invention provides use of a plant of *Brassica carinata* cultivar AGR044-312D, wherein a representative sample of said seed has been deposited under ATCC Accession number PTA-123015, to produce a *carinata* variety comprising a desired trait, wherein the desired trait is introduced by crossing a plant of cultivar AGR044-312D with a plant of another Brassicaceae species comprising the desired trait, and wherein the *carinata* variety produced from cultivar AGR044-312D has the desired trait and essentially all of the physiological and morphological characteristics of cultivar AGR044-312D when grown in the same location under the same environmental conditions, and wherein the desired trait is selected from the group consisting of male sterility, disease resistance, fungal resistance, pest resistance, herbicide tolerance, abiotic stress tolerance, and altered metabolism.

In another embodiment, the invention provides use of a plant of *Brassica carinata* cultivar AGR044-312D, wherein a representative sample of said seed has been deposited under ATCC Accession number PTA-123015, to produce a *carinata* variety comprising a desired trait, wherein the desired trait is introduced by crossing a plant of cultivar AGR044-312D with a plant of another Brassicaceae species comprising the desired trait, and wherein the desired trait is herbicide tolerance and the tolerance is conferred to a herbicide selected from but not limited to the group consisting of glyphosate, glufosinate, imidazolinones, and auxin analogues such as 2,4-D and dicamba.

In another embodiment, the invention provides use of a plant of *Brassica carinata* cultivar AGR044-312D, wherein a representative sample of said seed has been deposited under ATCC Accession number PTA-123015, to produce a *carinata* variety comprising a desired trait, wherein the desired trait is introduced by crossing a plant of cultivar AGR044-312D with a plant of another Brassicaceae species comprising the desired trait, and wherein the *carinata* variety produced from cultivar AGR044-312D has the desired trait and essentially all of the physiological and morphological characteristics of cultivar AGR044-312D when grown in the same location under the same environmental conditions, and wherein the desired trait is herbicide tolerance and the tolerance is conferred to a herbicide selected from but not limited to the group consisting of glyphosate, glufosinate, imidazolinones, and auxin analogues such as 2,4-D and dicamba.

In another embodiment, the invention provides a cell of a plant of a *carinata* variety comprising a desired trait, wherein the *carinata* variety is produced by a method comprising: (a) crossing a plant of cultivar AGR044-312D with a plant of another Brassicaceae species comprising the desired trait; (b) using embryo rescue techniques to recover viable F1 plants from the cross or growing F1 seeds to produce F1 plants; (c) selfing the F1 plants that have the desired trait and *carinata* character; (d) using embryo rescue techniques to recover viable F2 plants or growing F2 seeds to produce F2 plants; (e) selfing the F2 plants that have the desired trait and *carinata* character; (f) using embryo rescue techniques to recover viable F3 plants or growing F3 seeds to produce progeny plants; (g) selfing the progeny plants that have the desired trait and *carinata* character to produce further progeny plants; and (h) selecting the progeny plants with the desired trait and *carinata* character to produce the *carinata* variety produced from cultivar AGR044-312D.

In another embodiment, the invention provides a cell of a plant of a *carinata* variety comprising a desired trait, wherein the *carinata* variety is produced by a method comprising: (a) crossing a plant of cultivar AGR044-312D with a plant of another Brassicaceae species comprising the desired trait; (b) using embryo rescue techniques to recover viable F1 plants from the cross or growing F1 seeds to produce F1 plants; (c) selfing the F1 plants that have the desired trait and *carinata* character; (d) using embryo rescue techniques to recover viable F2 plants or growing F2 seeds to produce F2 plants; (e) selfing the F2 plants that have the desired trait and *carinata* character; (f) using embryo rescue techniques to recover viable F3 plants or growing F3 seeds to produce progeny plants; (g) selfing the progeny plants that have the desired trait and *carinata* character to produce further progeny plants; and (h) selecting the progeny plants with the desired trait and *carinata* character to produce the *carinata* variety produced from cultivar AGR044-312D; wherein steps (g) and (h) are repeated until the *carinata* variety produced from cultivar AGR044-312D has the desired trait and essentially all of the physiological and morphological characteristics of cultivar AGR044-312D when grown in the same location under the same environmental conditions.

In another embodiment, the invention provides a cell of a plant of a *carinata* variety comprising a desired trait, wherein the *carinata* variety is produced by a method comprising: (a) crossing a plant of cultivar AGR044-312D with a plant of another Brassicaceae species comprising the desired trait; (b) using embryo rescue techniques to recover viable F1 plants from the cross or growing F1 seeds to produce F1 plants; (c) selfing the F1 plants that have the desired trait and *carinata* character; (d) using embryo rescue techniques to recover viable F2 plants or growing F2 seeds to produce F2 plants; (e) selfing the F2 plants that have the desired trait and *carinata* character; (f) using embryo rescue techniques to recover viable F3 plants or growing F3 seeds to produce progeny plants; (g) selfing the progeny plants that have the desired trait and *carinata* character to produce further progeny plants; and (h) selecting the progeny plants with the desired trait and *carinata* character to produce the *carinata* variety produced from cultivar AGR044-312D; wherein the desired trait is selected from the group consisting of male sterility, disease resistance, fungal resistance, pest resistance, herbicide tolerance, abiotic stress tolerance, and altered metabolism.

In another embodiment, the invention provides a cell of a plant of a *carinata* variety comprising a desired trait, wherein the *carinata* variety is produced by a method comprising: (a) crossing a plant of cultivar AGR044-312D with a plant of another Brassicaceae species comprising the desired trait; (b) using embryo rescue techniques to recover viable F1 plants from the cross or growing F1 seeds to produce F1 plants; (c) selfing the F1 plants that have the desired trait and *carinata* character; (d) using embryo rescue techniques to recover viable F2 plants or growing F2 seeds to produce F2 plants; (e) selfing the F2 plants that have the desired trait and *carinata* character; (f) using embryo rescue techniques to recover viable F3 plants or growing F3 seeds to produce progeny plants; (g) selfing the progeny plants that have the desired trait and *carinata* character to produce further progeny plants; and (h) selecting the progeny plants with the desired trait and *carinata* character to produce the *carinata* variety produced from cultivar AGR044-312D; wherein steps (g) and (h) are repeated until the *carinata* variety produced from cultivar AGR044-312D has the desired trait and essentially all of the physiological and morphological characteristics of cultivar AGR044-312D when grown in the same location under the same environmental conditions, and wherein the desired trait is selected from the group consisting of male sterility, disease resistance, fungal resistance, pest resistance, herbicide tolerance, abiotic stress tolerance, and altered metabolism.

In another embodiment, the invention provides a cell of a plant of a *carinata* variety comprising a desired trait, wherein the *carinata* variety is produced by a method comprising: (a) crossing a plant of cultivar AGR044-312D with a plant of another Brassicaceae species comprising the desired trait; (b) using embryo rescue techniques to recover viable F1 plants from the cross or growing F1 seeds to produce F1 plants; (c) selfing the F1 plants that have the desired trait and *carinata* character; (d) using embryo rescue techniques to recover viable F2 plants or growing F2 seeds to produce F2 plants; (e) selfing the F2 plants that have the desired trait and *carinata* character; (f) using embryo rescue techniques to recover viable F3 plants or growing F3 seeds to produce progeny plants; (g) selfing the progeny plants that have the desired trait and *carinata* character to produce further progeny plants; and (h) selecting the progeny plants with the desired trait and *carinata* character to produce the *carinata* variety produced from cultivar AGR044-312D; wherein the desired trait is herbicide tolerance and the tolerance is conferred to a herbicide selected from but not limited to the group consisting of glyphosate, glufosinate, imidazolinones, and auxin analogues such as 2,4-D and dicamba.

In another embodiment, the invention provides a cell of a plant of a *carinata* variety comprising a desired trait, wherein the *carinata* variety is produced by a method comprising: (a) crossing a plant of cultivar AGR044-312D with a plant of another Brassicaceae species comprising the desired trait; (b) using embryo rescue techniques to recover viable F1 plants from the cross or growing F1 seeds to produce F1 plants; (c) selfing the F1 plants that have the desired trait and *carinata* character; (d) using embryo rescue techniques to recover viable F2 plants or growing F2 seeds to produce F2 plants; (e) selfing the F2 plants that have the desired trait and *carinata* character; (f) using embryo rescue techniques to recover viable F3 plants or growing F3 seeds to produce progeny plants; (g) selfing the progeny plants that have the desired trait and *carinata* character to produce further progeny plants; and (h) selecting the progeny plants with the desired trait and *carinata* character to produce the *carinata* variety produced from cultivar AGR044-312D; wherein steps (g) and (h) are repeated until the *carinata* variety produced from cultivar AGR044-312D has the desired trait and essentially all of the physiological and morphological characteristics of cultivar AGR044-312D when grown in the same location under the same environmental conditions, and wherein the desired trait is herbicide tolerance and the tolerance is conferred to a herbicide selected from but not limited to the group consisting of glyphosate, glufosinate, imidazolinones, and auxin analogues such as 2,4-D and dicamba.

5.1.13 Commercial Crops and Commercial Plant Products

In another embodiment, the invention provides a method of producing a commercial plant product, the method comprising growing a plant of *Brassica carinata* cultivar AGR044-312D produced from the seed of *Brassica carinata* cultivar designated AGR044-312D, wherein a representative sample of the seed has been deposited under ATCC Accession number PTA-123015, to produce a commercial crop, and producing said commercial plant product from the commercial crop.

In another embodiment, the invention provides a method of producing a commercial plant product, the method comprising growing a plant of *Brassica carinata* cultivar AGR044-312D produced from the seed of *Brassica carinata* cultivar designated AGR044-312D, wherein a representative sample of the seed has been deposited under ATCC Accession number PTA-123015, to produce a commercial crop, and producing said commercial plant product from the commercial crop, wherein the commercial plant product comprises oil, meal or protein isolate.

In another embodiment, the invention provides a method of producing a commercial plant product, the method comprising growing a plant of *Brassica carinata* cultivar AGR044-312D produced from the seed of *Brassica carinata* cultivar designated AGR044-312D, wherein a representative sample of the seed has been deposited under ATCC Accession number PTA-123015, to produce a commercial crop, and producing said commercial plant product from the commercial crop, wherein the commercial plant product comprises a biofumigant.

In another embodiment, the invention provides a commercial plant product produced by a method comprising growing a plant of *Brassica carinata* cultivar AGR044-312D produced from the seed of *Brassica carinata* cultivar designated AGR044-312D, wherein a representative sample of the seed has been deposited under ATCC Accession number PTA-123015, to produce a commercial crop, and producing said commercial plant product from the commercial crop.

In another embodiment, the invention provides a commercial plant product produced by a method comprising growing a plant of *Brassica carinata* cultivar AGR044-312D produced from the seed of *Brassica carinata* cultivar designated AGR044-312D, wherein a representative sample of the seed has been deposited under ATCC Accession number PTA-123015, to produce a commercial crop, and producing said commercial plant product from the commercial crop, wherein the commercial plant product comprises oil, meal, or protein isolate.

In another embodiment, the invention provides oil, meal, or protein isolate produced by a method comprising growing a plant of *Brassica carinata* cultivar AGR044-312D produced from the seed of *Brassica carinata* cultivar designated AGR044-312D, wherein a representative sample of the seed has been deposited under ATCC Accession number PTA-123015, to produce a commercial crop, and producing the oil, meal, or protein isolate from the commercial crop.

In another embodiment, the invention provides crushed, non-viable seed of *Brassica carinata* cultivar AGR044-312D, wherein a representative sample of said seed has been deposited under ATCC Accession number PTA-123015.

In another embodiment, the invention provides use of a plant of *Brassica carinata* cultivar AGR044-312D, wherein a representative sample of said seed has been deposited under ATCC Accession number PTA-123015, to produce a commercial crop.

In another embodiment, the invention provides use of a plant of *Brassica carinata* cultivar AGR044-312D, wherein a representative sample of said seed has been deposited under ATCC Accession number PTA-123015, to produce a commercial plant product.

In another embodiment, the invention provides use of a plant of *Brassica carinata* cultivar AGR044-312D, wherein a representative sample of said seed has been deposited under ATCC Accession number PTA-123015, to produce a commercial plant product, wherein the commercial plant product comprises oil, meal, or protein isolate.

In another embodiment, the invention provides crushed, non-viable seed of a *Brassica carinata* variety produced from *Brassica carinata* cultivar AGR044-312D, wherein a representative sample of said seed has been deposited under ATCC Accession number PTA-123015.

In another embodiment, the invention provides use of a plant of a *Brassica carinata* variety produced from *Brassica carinata* cultivar AGR044-312D, wherein a representative sample of said seed has been deposited under ATCC Accession number PTA-123015, to produce a commercial crop.

In another embodiment, the invention provides use of a plant of a *Brassica carinata* variety produced from *Brassica carinata* cultivar AGR044-312D, wherein a representative sample of said seed has been deposited under ATCC Accession number PTA-123015, to produce a commercial plant product.

In another embodiment, the invention provides use of a plant of a *Brassica carinata* variety produced from *Brassica carinata* cultivar AGR044-312D, wherein a representative sample of said seed has been deposited under ATCC Accession number PTA-123015, to produce a commercial plant product, wherein the commercial plant product comprises oil, meal, or protein isolate.

5.2 AGR044-3A22

5.2.1 Seeds, Plants, Plant Parts and Cells

In one embodiment, the invention provides a seed of *Brassica carinata* cultivar designated AGR044-3A22, wherein a representative sample of the seed has been deposited under ATCC Accession number PTA-123014.

In another embodiment, the invention provides a plant of *Brassica carinata* cultivar AGR044-3A22, or a part thereof, produced from the seed of *Brassica carinata* cultivar designated AGR044-3A22, wherein a representative sample of the seed has been deposited under ATCC Accession number PTA-123014.

In another embodiment, the invention provides a plant part of *Brassica carinata* cultivar AGR044-3A22, or a part thereof, produced from the seed of *Brassica carinata* cultivar designated AGR044-3A22, wherein a representative sample of the seed has been deposited under ATCC Accession number PTA-123014, wherein the plant part is an ovule, a leaf, pollen, a seed, an embryo a root, a root tip, a pod, a flower, a stalk, a cell, or a protoplast.

In another embodiment, the invention provides a plant part of *Brassica carinata* cultivar AGR044-3A22, or a part thereof, produced from the seed of *Brassica carinata* cultivar designated AGR044-3A22, wherein a representative sample of the seed has been deposited under ATCC Accession number PTA-123014, wherein the plant part is pollen.

In another embodiment, the invention provides a plant part of *Brassica carinata* cultivar AGR044-3A22, or a part thereof, produced from the seed of *Brassica carinata* cultivar designated AGR044-3A22, wherein a representative sample of the seed has been deposited under ATCC Accession number PTA-123014, wherein the plant part is an ovule.

In another embodiment, the invention provides a *Brassica carinata* plant, or a part thereof, having essentially all of the physiological and morphological characteristics of a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, when grown in the same location under the same environmental conditions.

In another embodiment, the invention provides a cell of a seed of *Brassica carinata* cultivar designated AGR044-3A22, wherein a representative sample of said seed has been deposited under ATCC Accession number PTA-123014.

In another embodiment, the invention provides a cell of a plant of *Brassica carinata* cultivar AGR044-3A22, or a part thereof, produced from a seed of *Brassica carinata* cultivar designated AGR044-3A22, wherein a representative sample of said seed has been deposited under ATCC Accession number PTA-123014.

In another embodiment, the invention provides a protoplast of a plant of *Brassica carinata* cultivar AGR044-3A22, or a part thereof, produced from a seed of *Brassica carinata* cultivar designated AGR044-3A22, wherein a representative sample of said seed has been deposited under ATCC Accession number PTA-123014.

In another embodiment, the invention provides a cell of a plant of *Brassica carinata* cultivar AGR044-3A22, or a part thereof, produced from a seed of *Brassica carinata* cultivar designated AGR044-3A22, wherein a representative sample of said seed has been deposited under ATCC Accession number PTA-123014, wherein the plant part is an ovule, a leaf, pollen, a seed, an embryo a root, a root tip, a pod, a flower, or a stalk.

In another embodiment, the invention provides a cell of a plant of *Brassica carinata* cultivar AGR044-3A22, or a part thereof, produced from a seed of *Brassica carinata* cultivar designated AGR044-3A22, wherein a representative sample of said seed has been deposited under ATCC Accession number PTA-123014, wherein the plant part is pollen.

In another embodiment, the invention provides a cell of a plant of *Brassica carinata* cultivar AGR044-3A22, or a part thereof, produced from a seed of *Brassica carinata* cultivar designated AGR044-3A22, wherein a representative sample of said seed has been deposited under ATCC Accession number PTA-123014, wherein the plant part is an ovule.

In another embodiment, the invention provides a cell of a *Brassica carinata* plant, or parts thereof, having essentially all of the physiological and morphological characteristics of a plant of *Brassica carinata* cultivar AGR044-3A22 produced from a seed of *Brassica carinata* cultivar designated AGR044-3A22, wherein a representative sample of said seed has been deposited under ATCC Accession number PTA-123014, when grown in the same location under the same environmental conditions.

5.2.2 Tissue Cultures and Regenerated Plants

In another embodiment, the invention provides a tissue culture of protoplasts or regenerable cells of a plant of *Brassica carinata* cultivar AGR044-3A22, or a part thereof, produced from the seed of *Brassica carinata* cultivar designated AGR044-3A22, wherein a representative sample of the seed has been deposited under ATCC Accession number PTA-123014.

In another embodiment, the invention provides a tissue culture of protoplasts or regenerable cells of a plant of *Brassica carinata* cultivar AGR044-3A22, or a part thereof, produced from the seed of *Brassica carinata* cultivar designated AGR044-3A22, wherein a representative sample of the seed has been deposited under ATCC Accession number PTA-123014, wherein the protoplasts or regenerable cells are produced from a tissue selected from the group consisting of leaves, pollen, embryos, roots, root tips, pods, flowers, ovules, and stalks.

In another embodiment, the invention provides a *Brassica carinata* plant regenerated from a tissue culture of protoplasts or regenerable cells of a plant of *Brassica carinata* cultivar AGR044-3A22, or a part thereof, produced from the seed of *Brassica carinata* cultivar designated AGR044-3A22, wherein a representative sample of the seed has been deposited under ATCC Accession number PTA-123014, wherein the plant has essentially all of the morphological and physiological characteristics of cultivar AGR044-3A22, the seed of which has been deposited under ATCC Accession number PTA-123014, when grown in the same location under the same environmental conditions.

In another embodiment, the invention provides a *Brassica carinata* plant regenerated from a tissue culture of protoplasts or regenerable cells of a plant of *Brassica carinata* cultivar AGR044-3A22, or a part thereof, produced from the seed of *Brassica carinata* cultivar designated AGR044-3A22, wherein a representative sample of the seed has been deposited under ATCC Accession number PTA-123014, wherein the protoplasts or regenerable cells are produced from a tissue selected from the group consisting of leaves, pollen, embryos, roots, root tips, pods, flowers, ovules, and stalks, wherein the plant has essentially all of the morphological and physiological characteristics of cultivar AGR044-3A22, the seed of which has been deposited under ATCC Accession number PTA-123014, when grown in the same location under the same environmental conditions.

In another embodiment, the invention provides a regenerated *Brassica carinata* plant having essentially all of the physiological and morphological characteristics of the cultivar AGR044-3A22 when grown in the same location under the same environmental conditions, the regenerated plant having been produced using a tissue culture, wherein the tissue culture is produced from a plant of *Brassica carinata* cultivar AGR044-3A22, or a part thereof, produced from the seed of *Brassica carinata* cultivar designated AGR044-3A22, wherein a representative sample of the seed has been deposited under ATCC Accession number PTA-123014.

In another embodiment, the invention provides a cell of a *Brassica carinata* plant regenerated from a tissue culture of protoplasts or regenerable cells of a plant of *Brassica carinata* cultivar AGR044-3A22, or a part thereof, produced from the seed of *Brassica carinata* cultivar designated AGR044-3A22, wherein a representative sample of the seed has been deposited under ATCC Accession number PTA-123014, wherein the plant has essentially all of the morphological and physiological characteristics of cultivar AGR044-3A22, the seed of which has been deposited under ATCC Accession number PTA-123014, when grown in the same location under the same environmental conditions.

In another embodiment, the invention provides a cell of a *Brassica carinata* plant regenerated from a tissue culture of protoplasts or regenerable cells of a plant of *Brassica carinata* cultivar AGR044-3A22, or a part thereof, produced from the seed of *Brassica carinata* cultivar designated AGR044-3A22, wherein a representative sample of the seed has been deposited under ATCC Accession number PTA-123014, wherein the protoplasts or regenerable cells are produced from a tissue selected from the group consisting of leaves, pollen, embryos, roots, root tips, pods, flowers, ovules, and stalks, wherein the plant has essentially all of the morphological and physiological characteristics of cultivar AGR044-3A22, the seed of which has been deposited under ATCC Accession number PTA-123014, when grown in the same location under the same environmental conditions.

In another embodiment, the invention provides a cell of a regenerated *Brassica carinata* plant having essentially all of the physiological and morphological characteristics of the cultivar AGR044-3A22 when grown in the same location under the same environmental conditions, the regenerated plant having been produced using a tissue culture, wherein the tissue culture is produced from a plant of *Brassica carinata* cultivar AGR044-3A22, or a part thereof, produced from the seed of *Brassica carinata* cultivar designated AGR044-3A22, wherein a representative sample of the seed has been deposited under ATCC Accession number PTA-123014.

5.2.3 Methods of Crossing and Uses for Crossing *Brassica carinata* Plants, and the Cells and Seeds Produced Therefrom In another embodiment, the invention provides a method for producing *Brassica carinata* seed comprising crossing *Brassica carinata* plants and harvesting the resulting *Brassica carinata* seed, wherein at least one *Brassica carinata* plant is a plant of *Brassica carinata* cultivar AGR044-3A22 produced from the seed of *Brassica carinata* cultivar designated AGR044-3A22, wherein a representative sample of the seed has been deposited under ATCC Accession number PTA-123014.

In another embodiment, the invention provides a *Brassica carinata* seed produced by a method for producing *Brassica carinata* seed comprising crossing *Brassica carinata* plants and harvesting the resulting *Brassica carinata* seed, wherein at least one *Brassica carinata* plant is a plant of *Brassica carinata* cultivar AGR044-3A22 produced from the seed of *Brassica carinata* cultivar designated AGR044-3A22, wherein a representative sample of the seed has been deposited under ATCC Accession number PTA-123014.

In another embodiment, the invention provides a cell of a *Brassica carinata* seed produced by a method for producing *Brassica carinata* seed comprising crossing *Brassica carinata* plants and harvesting the resulting *Brassica carinata* seed, wherein at least one *Brassica carinata* plant is a plant of *Brassica carinata* cultivar AGR044-3A22 produced from the seed of *Brassica carinata* cultivar designated AGR044-3A22, wherein a representative sample of the seed has been deposited under ATCC Accession number PTA-123014.

In another embodiment, the invention provides use of a plant of *Brassica carinata* cultivar AGR044-3A22, wherein a representative sample of said seed has been deposited under ATCC Accession number PTA-123014, to produce seed, wherein the seed is produced by self-fertilization or cross-fertilization.

5.2.4 Methods of and Uses for Producing an F1 Hybrid *Brassica carinata* Seed, and the Cells, Seeds and Plants Produced Therefrom In another embodiment, the invention provides a method for producing a first generation (F1) hybrid *Brassica carinata* seed comprising crossing a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, with a different *Brassica carinata* plant and harvesting the resultant F1 hybrid *carinata* seed, and wherein the plant of *Brassica carinata* cultivar AGR044-3A22 produced from the seed of *Brassica carinata* cultivar designated AGR044-3A22 is either a female parent or a male parent.

In another embodiment, the invention provides a method for producing a first generation (F1) hybrid *Brassica carinata* seed comprising crossing a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, with a different *Brassica carinata* plant and harvesting the resultant F1 hybrid *carinata* seed, and wherein the plant of *Brassica carinata* cultivar AGR044-3A22 produced from the seed of *Brassica carinata* cultivar designated AGR044-3A22 is the female parent.

In another embodiment, the invention provides a method for producing a first generation (F1) hybrid *Brassica carinata* seed comprising crossing a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, with a different *Brassica carinata* plant and harvesting the resultant F1 hybrid *carinata* seed, and wherein the plant of *Brassica carinata* cultivar AGR044-3A22 produced from the seed of *Brassica carinata* cultivar designated AGR044-3A22 is the male parent.

In another embodiment, the invention provides an F1 hybrid seed produced by a method comprising crossing a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, with a different *Brassica carinata* plant and harvesting the resultant F1 hybrid *carinata* seed, and wherein the plant of *Brassica carinata* cultivar AGR044-3A22 produced from the seed of *Brassica carinata* cultivar designated AGR044-3A22 is either a female parent or a male parent.

In another embodiment, the invention provides an F1 hybrid seed produced by a method comprising crossing a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, with a different *Brassica carinata* plant and harvesting the resultant F1 hybrid *carinata* seed, and wherein the plant of *Brassica carinata* cultivar AGR044-3A22 produced from the seed of *Brassica carinata* cultivar designated AGR044-3A22 is the female parent.

In another embodiment, the invention provides an F1 hybrid seed produced by a method comprising crossing a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, with a different *Brassica carinata* plant and harvesting the resultant F1 hybrid *carinata* seed, and wherein the plant of *Brassica carinata* cultivar AGR044-3A22 produced from the seed of *Brassica carinata* cultivar designated AGR044-3A22 is the male parent.

In another embodiment, the invention provides an F1 hybrid plant grown from an F1 hybrid seed produced by a method comprising crossing a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, with a different *Brassica carinata* plant and harvesting the resultant F1 hybrid *carinata* seed, and wherein the plant of *Brassica carinata* cultivar AGR044-3A22 produced from the seed of *Brassica carinata* cultivar designated AGR044-3A22 is either a female parent or a male parent.

In another embodiment, the invention provides an F1 hybrid plant grown from an F1 hybrid seed produced by a method comprising crossing a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, with a different *Brassica carinata* plant and harvesting the resultant F1 hybrid *carinata* seed, and wherein the plant of *Brassica carinata* cultivar AGR044-3A22 produced from the seed of *Brassica carinata* cultivar designated AGR044-3A22 is the female parent.

In another embodiment, the invention provides an F1 hybrid plant grown from an F1 hybrid seed produced by a method comprising crossing a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, with a different *Brassica carinata* plant and harvesting the resultant F1 hybrid *carinata* seed, and wherein the plant of *Brassica carinata* cultivar AGR044-3A22 produced from the seed of *Brassica carinata* cultivar designated AGR044-3A22 is the male parent.

In another embodiment, the invention provides use of a plant of *Brassica carinata* cultivar AGR044-3A22, wherein a representative sample of said seed has been deposited under ATCC Accession number PTA-123014 to produce an F1 hybrid *Brassica carinata* seed, wherein the plant is either a female parent or a male parent in a cross-fertilization.

In another embodiment, the invention provides use of a plant of *Brassica carinata* cultivar AGR044-3A22, wherein a representative sample of said seed has been deposited under ATCC Accession number PTA-123014 to produce an F1 hybrid *Brassica carinata* seed, wherein the plant is the female parent.

In another embodiment, the invention provides use of a plant of *Brassica carinata* cultivar AGR044-3A22, wherein a representative sample of said seed has been deposited under ATCC Accession number PTA-123014 to produce an F1 hybrid *Brassica carinata* seed, wherein the plant is the male parent.

In another embodiment, the invention provides a cell of an F1 hybrid plant grown from the F1 hybrid seed produced by any of the above uses.

In another embodiment, the invention provides a cell of an F1 hybrid plant grown from F1 hybrid seed produced by a method comprising crossing a plant of *Brassica carinata* cultivar AGR044-3A22, wherein a representative sample of said seed has been deposited under ATCC Accession number PTA-123014, with a different *Brassica carinata* plant and harvesting the resultant F1 hybrid *carinata* seed.

5.2.5 Methods of and Uses for Producing a Doubled Haploidy Variety, and the Cells, Seeds, and Plants Produced Therefrom In another embodiment, the invention provides a method for producing a Doubled Haploidy variety comprising: (a) isolating a flower bud of an F1 hybrid plant grown from an F1 hybrid seed produced by a method comprising crossing a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, with a different *Brassica carinata* plant and harvesting the resultant F1 hybrid *carinata* seed, and wherein the plant of *Brassica carinata* cultivar AGR044-3A22 produced from the seed of *Brassica carinata* cultivar designated AGR044-3A22 is either a female parent or a male parent; (b) dissecting out a haploid microspore; (c) placing the haploid microspore in culture; (d) inducing the microspore to differentiate into an embryo and subsequently into a plantlet; (e) identifying whether the plantlet contains a diploid chromosome number, wherein the diploid chromosome number occured through chromosome doubling; and (f) continuing to grow the plantlet if it contains a diploid chromosome number.

In another embodiment, the invention provides a method for producing a Doubled Haploidy variety comprising: (a) isolating a flower bud of an F1 hybrid plant grown from an F1 hybrid seed produced by a method comprising crossing a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, with a different *Brassica carinata* plant and harvesting the resultant F1 hybrid *carinata* seed, and wherein the plant of *Brassica carinata* cultivar AGR044-3A22 produced from the seed of *Brassica carinata* cultivar designated AGR044-3A22 is the female parent; (b) dissecting out a haploid microspore; (c) placing the haploid microspore in culture; (d) inducing the microspore to differentiate into an embryo and subsequently into a plantlet; (e) identifying whether the plantlet contains a diploid chromosome number, wherein the diploid chromosome number occured through chromosome doubling; and (f) continuing to grow the plantlet if it contains a diploid chromosome number.

In another embodiment, the invention provides a method for producing a Doubled Haploidy variety comprising: (a) isolating a flower bud of an F1 hybrid plant grown from an F1 hybrid seed produced by a method comprising crossing a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, with a different *Brassica carinata* plant and harvesting the resultant F1 hybrid *carinata* seed, and wherein the plant of *Brassica carinata* cultivar AGR044-3A22 produced from the seed of *Brassica carinata* cultivar designated AGR044-3A22 is the male parent; (b) dissecting out a haploid microspore; (c) placing the haploid microspore in culture; (d) inducing the microspore to differentiate into an embryo and subsequently into a plantlet; (e) identifying whether the plantlet contains a diploid chromosome number, wherein the diploid chromosome number occured through chromosome doubling; and (f) continuing to grow the plantlet if it contains a diploid chromosome number.

In another embodiment, the invention provides a method for producing a Doubled Haploidy variety comprising: (a) isolating a flower bud of an F1 hybrid plant grown from an F1 hybrid seed produced by a method comprising crossing a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, with a different *Brassica carinata* plant and harvesting the resultant F1 hybrid *carinata* seed, and wherein the plant of *Brassica carinata* cultivar AGR044-3A22 produced from the seed of *Brassica carinata* cultivar designated AGR044-3A22 is either a female parent or a male parent; (b) dissecting out a haploid microspore; (c) placing the haploid microspore in culture; (d) inducing the microspore to differentiate into an embryo and subsequently into a plantlet; (e) identifying whether the plantlet contains a diploid chromosome number, wherein the diploid chromosome number occured through chromosome doubling; and (f) continuing to grow the plantlet if it contains a diploid chromosome number; wherein the method further comprises inducing chromosome doubling by chemical or physical means.

In another embodiment, the invention provides a method for producing a Doubled Haploidy variety comprising: (a) isolating a flower bud of an F1 hybrid plant grown from an F1 hybrid seed produced by a method comprising crossing a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, with a different *Brassica carinata* plant and harvesting the resultant F1 hybrid *carinata* seed, and wherein the plant of *Brassica carinata* cultivar AGR044-3A22 produced from the seed of *Brassica carinata* cultivar designated AGR044-3A22 is the female parent; (b) dissecting out a haploid microspore; (c) placing the haploid microspore in culture; (d) inducing the microspore to differentiate into an embryo and subsequently into a plantlet; (e) identifying whether the plantlet contains a diploid chromosome number, wherein the diploid chromosome number occured through chromosome doubling; and (f) continuing to grow the plantlet if it contains a diploid chromosome number; wherein the method further comprises inducing chromosome doubling by chemical or physical means.

In another embodiment, the invention provides a method for producing a Doubled Haploidy variety comprising: (a) isolating a flower bud of an F1 hybrid plant grown from an F1 hybrid seed produced by a method comprising crossing a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, with a different *Brassica carinata* plant and harvesting the resultant F1 hybrid *carinata* seed, and wherein the plant of *Brassica carinata* cultivar AGR044-3A22 produced from the seed of *Brassica carinata* cultivar designated AGR044-3A22 is the male parent; (b) dissecting out a haploid microspore; (c) placing the haploid microspore in culture; (d) inducing the microspore to differentiate into an embryo and subsequently into a plantlet; (e) identifying whether the plantlet contains a diploid chromosome number, wherein the diploid chromosome number occured through chromosome doubling; and (f) continuing to grow the plantlet if it contains a diploid chromosome number; wherein the method further comprises inducing chromosome doubling by chemical or physical means.

In another embodiment, the invention provides a plant, or part thereof, or seed of a Doubled Haploidy variety produced by any of the above methods.

In another embodiment, the invention provides use of a plant of *Brassica carinata* cultivar AGR044-3A22, wherein a representative sample of said seed has been deposited under ATCC Accession number PTA-123014 to produce a Doubled Haploidy variety.

In another embodiment, the invention provides use of a plant of *Brassica carinata* cultivar AGR044-3A22, wherein a representative sample of said seed has been deposited under ATCC Accession number PTA-123014 to produce a Doubled Haploidy variety, wherein chromosome doubling is introduced by chemical or physical means.

In another embodiment, the invention provides a cell of a Doubled Haploidy variety produced from *Brassica carinata* cultivar AGR044-3A22, wherein a representative sample of the seed has been deposited under ATCC Accession number PTA-123014.

In another embodiment, the invention provides use of a plant of a *Brassica carinata* variety produced from *Brassica carinata* cultivar AGR044-3A22, wherein a representative sample of said seed has been deposited under ATCC Accession number PTA-123014, to produce a Doubled Haploidy variety.

In another embodiment, the invention provides use of a plant of a *Brassica carinata* variety produced from *Brassica carinata* cultivar AGR044-3A22, wherein a representative sample of said seed has been deposited under ATCC Accession number PTA-123014, to produce a Doubled Haploidy variety, wherein chromosome doubling is introduced by chemical or physical means.

5.2.6 Desired Traits

In one aspect, the present invention includes the introduction of a desired trait into *Brassica carinata* cultivar AGR044-3A22, wherein a representative sample of the seed has been deposited under ATCC Accession number PTA-123014, to produce a *Brassica carinata* variety comprising the desired trait.

Examples of potential desired traits include:

a. cytoplasmic male sterility, CMS restorer traits, b. biotic and abiotic stress resistance such as disease resistance, fungal resistance, pest resistance, drought tolerance, and frost tolerance, c. agronomic traits such as increased pod shatter resistance, improved harvestability, improved nutrient usage efficiency, seed colour seed size, seed pod size, seed pod architecture, seed pod fill. earlier and more uniform time to flowering, earlier maturity, extent of branching, flower colour and density, and plant height, d. altered metabolism (increased seed oil, increased seed protein, altered seed oil or fatty acid profile, reduced seed content of glucosinolates and other antinutritionals), e. improved performance: improved oil per unit area, improved grain per unit area, f. herbicide tolerance including tolerance to glyphosate, glufosinate, imidazolinones and auxin analogues such as 2,4-D and dicamba.

5.2.7 Methods of and Uses for Introducing a Desired Trait by Crossing and Backcrossing, and the Cells, Seeds and Plants Produced Therefrom In another embodiment, the invention provides a method of producing a *Brassica carinata* variety produced from a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, and wherein the *Brassica carinata* variety comprises a desired trait, the method comprising the steps of: (a) crossing a plant of cultivar AGR044-3A22 with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-3A22 to produce backcross progeny seed; and (d) growing the resultant backcross progeny seed and selecting backcross progeny plants that have the desired trait to produce the *Brassica carinata* variety produced from cultivar AGR044-3A22.

In another embodiment, the invention provides a method of producing a *Brassica carinata* variety produced from a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, and wherein the *Brassica carinata* variety comprises a desired trait, the method comprising the steps of: (a) crossing a plant of cultivar AGR044-3A22 with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-3A22 to produce backcross progeny seed; and (d) growing the resultant backcross progeny seed and selecting backcross progeny plants that have the desired trait to produce the *Brassica carinata* variety produced from cultivar AGR044-3A22; wherein steps (c) and (d) are repeated until the *Brassica carinata* variety produced from cultivar AGR044-3A22 has the desired trait and essentially all of the physiological and morphological characteristics of cultivar AGR044-3A22 when grown in the same location under the same environmental conditions.

In another embodiment, the invention provides a method of producing a *Brassica carinata* variety produced from a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, and wherein the *Brassica carinata* variety comprises a desired trait, the method comprising the steps of: (a) crossing a plant of cultivar AGR044-3A22 with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-3A22 to produce backcross progeny seed; and (d) growing the resultant backcross progeny seed and selecting backcross progeny plants that have the desired trait to produce the *Brassica carinata* variety produced from cultivar AGR044-3A22; and wherein the desired trait is selected from the group consisting of male sterility, disease resistance, fungal resistance, pest resistance, herbicide tolerance, abiotic stress tolerance, and altered metabolism.

In another embodiment, the invention provides a method of producing a *Brassica carinata* variety produced from a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, and wherein the *Brassica carinata* variety comprises a desired trait, the method comprising the steps of: (a) crossing a plant of cultivar AGR044-3A22 with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-3A22 to produce backcross progeny seed; and (d) growing the resultant backcross progeny seed and selecting backcross progeny plants that have the desired trait to produce the *Brassica carinata* variety produced from cultivar AGR044-3A22; wherein steps (c) and (d) are repeated until the *Brassica carinata* variety produced from cultivar AGR044-3A22 has the desired trait and essentially all of the physiological and morphological characteristics of cultivar AGR044-3A22 when grown in the same location under the same environmental conditions; and wherein the desired trait is selected from the group consisting of male sterility, disease resistance, fungal resistance, pest resistance, herbicide tolerance, abiotic stress tolerance, and altered metabolism.

In another embodiment, the invention provides a method of producing a *Brassica carinata* variety produced from a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, and wherein the *Brassica carinata* variety comprises a desired trait, the method comprising the steps of: (a) crossing a plant of cultivar AGR044-3A22 with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-3A22 to produce backcross progeny seed; and (d) growing the resultant backcross progeny seed and selecting backcross progeny plants that have the desired trait to produce the *Brassica carinata* variety produced from cultivar AGR044-3A22; and wherein the desired trait is herbicide tolerance and the tolerance is conferred to a herbicide selected from but not limited to the group consisting of glyphosate, glufosinate, imidazolinones, and auxin analogues such as 2,4-D and dicamba.

In another embodiment, the invention provides a method of producing a *Brassica carinata* variety produced from a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, and wherein the *Brassica carinata* variety comprises a desired trait, the method comprising the steps of: (a) crossing a plant of cultivar AGR044-3A22 with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-3A22 to produce backcross progeny seed; and (d) growing the resultant backcross progeny seed and selecting backcross progeny plants that have the desired trait to produce the *Brassica carinata* variety produced from cultivar AGR044-3A22; wherein steps (c) and (d) are repeated until the *Brassica carinata* variety produced from cultivar AGR044-3A22 has the desired trait and essentially all of the physiological and morphological characteristics of cultivar AGR044-3A22 when grown in the same location under the same environmental conditions; and wherein the desired trait is herbicide tolerance and the tolerance is conferred to a herbicide selected from but not limited to the group consisting of glyphosate, glufosinate, imidazolinones, and auxin analogues such as 2,4-D and dicamba.

In another embodiment, the invention provides a plant, or part thereof, or seed of a *Brassica carinata* variety produced by any of the above methods.

In another embodiment, the invention provides use of a plant of *Brassica carinata* cultivar AGR044-3A22, wherein a representative sample of said seed has been deposited under ATCC Accession number PTA-123014, to produce a *Brassica carinata* variety comprising a desired trait.

In another embodiment, the invention provides use of a plant of *Brassica carinata* cultivar AGR044-3A22, wherein a representative sample of said seed has been deposited under ATCC Accession number PTA-123014, to produce a *Brassica carinata* variety comprising a desired trait, wherein the desired trait is selected from the group consisting of male sterility, disease resistance, fungal resistance, pest resistance, herbicide tolerance, abiotic stress tolerance, and altered metabolism.

In another embodiment, the invention provides use of a plant of *Brassica carinata* cultivar AGR044-3A22, wherein a representative sample of said seed has been deposited under ATCC Accession number PTA-123014, to produce a *Brassica carinata* variety comprising a desired trait, wherein the desired trait is herbicide tolerance and the tolerance is conferred to a herbicide selected from but not limited to the group consisting of glyphosate, glufosinate, imidazolinones, and auxin analogues such as 2,4-D and dicamba.

In another embodiment, the invention provides a cell of a plant of a *Brassica carinata* variety produced from *Brassica carinata* cultivar AGR044-3A22, wherein a representative sample of said seed has been deposited under ATCC Accession number PTA-123014, wherein the *Brassica carinata* variety comprises a desired trait, and wherein the *Brassica carinata* variety is produced by a method comprising the steps of: (a) crossing a plant of cultivar AGR044-3A22 with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-3A22 to produce backcross progeny plants; and (d) growing the resultant backcross progeny seed and selecting backcross progeny plants that have the desired trait to produce the *Brassica carinata* variety produced from cultivar AGR044-3A22.

In another embodiment, the invention provides a cell of a plant of a *Brassica carinata* variety produced from *Brassica carinata* cultivar AGR044-3A22, wherein a representative sample of said seed has been deposited under ATCC Accession number PTA-123014, wherein the variety comprises a desired trait, and wherein the *Brassica carinata* variety is produced by a method comprising the steps of: (a) crossing a plant of cultivar AGR044-3A22 with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-3A22 to produce backcross progeny plants; and (d) growing the resultant backcross progeny seed and selecting backcross progeny plants that have the desired trait to produce the *Brassica carinata* variety produced from cultivar AGR044-3A22; wherein the method to produce the *Brassica carinata* variety further comprises repeating steps (c) and (d) until the *Brassica carinata* variety produced from cultivar AGR044-3A22 has the desired trait and essentially all of the physiological and morphological characteristics of cultivar AGR044-3A22 when grown in the same location under the same environmental conditions.

In another embodiment, the invention provides a cell of a plant of a *Brassica carinata* variety produced from *Brassica carinata* cultivar AGR044-3A22, wherein a representative sample of said seed has been deposited under ATCC Accession number PTA-123014, wherein the *Brassica carinata* variety comprises a desired trait, and wherein the *Brassica carinata* variety is produced by a method comprising the steps of: (a) crossing a plant of cultivar AGR044-3A22 with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-3A22 to produce backcross progeny plants; and (d) growing the resultant backcross progeny seed and selecting backcross progeny plants that have the desired trait to produce the *Brassica carinata* variety produced from cultivar AGR044-3A22; wherein the desired trait is selected from the group consisting of male sterility, disease resistance, fungal resistance, pest resistance, herbicide tolerance, abiotic stress tolerance, and altered metabolism.

In another embodiment, the invention provides a cell of a plant of a *Brassica carinata* variety produced from *Brassica carinata* cultivar AGR044-3A22, wherein a representative sample of said seed has been deposited under ATCC Accession number PTA-123014, wherein the *Brassica carinata* variety comprises a desired trait, and wherein the *Brassica carinata* variety is produced by a method comprising the steps of: (a) crossing a plant of cultivar AGR044-3A22 with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-3A22 to produce backcross progeny plants; and (d) growing the resultant backcross progeny seed and selecting backcross progeny plants that have the desired trait to produce the *Brassica carinata* variety produced from cultivar AGR044-3A22;

wherein the method to produce the *Brassica carinata* variety further comprises repeating steps (c) and (d) until the *Brassica carinata* variety produced from cultivar AGR044-3A22 has the desired trait and essentially all of the physiological and morphological characteristics of cultivar AGR044-3A22 when grown in the same location under the same environmental conditions, and wherein the desired trait is selected from the group consisting of male sterility, disease resistance, fungal resistance, pest resistance, herbicide tolerance, abiotic stress tolerance, and altered metabolism.

In another embodiment, the invention provides a cell of a plant of a *Brassica carinata* variety produced from *Brassica carinata* cultivar AGR044-3A22, wherein a representative sample of said seed has been deposited under ATCC Accession number PTA-123014, wherein the *Brassica carinata* variety comprises a desired trait, and wherein the *Brassica carinata* variety is produced by a method comprising the steps of: (a) crossing a plant of cultivar AGR044-3A22 with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-3A22 to produce backcross progeny plants; and (d) growing the resultant backcross progeny seed and selecting backcross progeny plants that have the desired trait to produce the *Brassica carinata* variety produced from cultivar AGR044-3A22, wherein the desired trait is herbicide tolerance and the tolerance is conferred to a herbicide selected from but not limited to the group consisting of glyphosate, glufosinate, imidazolinones, and auxin analogues such as 2,4-D and dicamba.

In another embodiment, the invention provides a cell of a plant of a *Brassica carinata* variety produced from *Brassica carinata* cultivar AGR044-3A22, wherein a representative sample of said seed has been deposited under ATCC Accession number PTA-123014, wherein the *Brassica carinata* variety comprises a desired trait, and wherein the *Brassica carinata* variety is produced by a method comprising the steps of: (a) crossing a plant of cultivar AGR044-3A22 with another *Brassica carinata* variety comprising the desired trait; (b) growing the resultant F1 hybrid seed and selecting one or more progeny plants that have the desired trait; (c) backcrossing the selected progeny plants that have the desired trait with plants of cultivar AGR044-3A22 to produce backcross progeny plants; and (d) growing the resultant backcross progeny seed and selecting backcross progeny plants that have the desired trait to produce the *Brassica carinata* variety produced from cultivar AGR044-3A22; wherein the method to produce the *Brassica carinata* variety further comprises repeating steps (c) and (d) until the *Brassica carinata* variety produced from cultivar AGR044-3A22 has the desired trait and essentially all of the physiological and morphological characteristics of cultivar AGR044-3A22 when grown in the same location under the same environmental conditions, wherein the desired trait is herbicide tolerance and the tolerance is conferred to a herbicide selected from but not limited to the group consisting of glyphosate, glufosinate, imidazolinones, and auxin analogues such as 2,4-D and dicamba.

5.2.8 DNA Constructs

In one aspect, the present invention includes the introduction of a desired trait into *Brassica carinata* cultivar AGR044-3A22, wherein a representative sample of the seed has been deposited under ATCC Accession number PTA-123014, to produce a *Brassica carinata* variety comprising the desired trait, wherein the desired trait is conferred by a DNA construct.

The DNA construct can be introduced by a variety of methods, including by using polyethylene glycol (PEG) mediated DNA uptake, electroporation, ballistic infiltration using DNA coated microprojectiles (gene gun), an *Agrobacterium* infiltration based vector, or a plant virus based vector.

The DNA construct can comprise any type of DNA, including a transgene or a DNA construct that is designed to modulate the expression of endogenous genes.

Examples of transgenes that could be incorporated can include, but are not limited to, the following: *Crambe abbysinica* FAE1, *Teesdalia nodulicans* FAE1, *Cardamine graeca* FAE1 *Brassica napus* DGAT, *Tropaeolum majus* DGAT, Yeast SLC1

DNA constructs that are designed to modulate the expression of endogenous genes may include, but are not limited to the following group: *Brassica carinata* Myb28, Myb29, FAD2 and FAD3 antisense RNA or RNAi sequences, which can be used to interfere or knock down the expression of endogenous genes to extremely low levels, simulating the effect of a null mutation at the endogenous locus. As discussed above, because *Brassica carinata* is amphidiploid, it can have multiple copies of genes from the contributing ancestral species that may create a high level of functional redundancy. As such, a single mutation in one of the homologues may not be sufficient to confer a phenotype. By using RNAi or an antisense approach, one may conceivably be capable of targeting all of the expressed homologues and achieving a functional knockdown effect. Such approaches require the RNAi or antisense RNA to be stably expressed.

5.2.9 Methods of and Uses for Introducing a Desired Trait Using DNA Constructs, and the Cells, Seeds and Plants Produced Therefrom In another embodiment, the invention provides a method of producing a *Brassica carinata* variety produced from *Brassica carinata* cultivar AGR044-3A22, wherein a representative sample of the seed has been deposited under ATCC Accession number PTA-123014, and wherein the *Brassica carinata* variety comprises a desired trait, the method comprising introducing a DNA construct conferring the desired trait into a plant of cultivar AGR044-3A22.

In another embodiment, the invention provides a method of producing a *Brassica carinata* variety produced from *Brassica carinata* cultivar AGR044-3A22, wherein a representative sample of the seed has been deposited under ATCC Accession number PTA-123014, wherein the *Brassica carinata* variety comprises a desired trait, the method comprising introducing a DNA construct conferring the desired trait into a plant of cultivar AGR044-3A22, and wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector.

In another embodiment, the invention provides a method of producing a *Brassica carinata* variety produced from *Brassica carinata* cultivar AGR044-3A22, wherein a representative sample of the seed has been deposited under ATCC Accession number PTA-123014, wherein the *Brassica carinata* variety comprises a desired trait, the method comprising introducing a DNA construct conferring the desired trait into a plant of cultivar AGR044-3A22, and wherein the DNA construct comprises a transgene.

In another embodiment, the invention provides a method of producing a *Brassica carinata* variety produced from

*Brassica carinata* cultivar AGR044-3A22, wherein a representative sample of the seed has been deposited under ATCC Accession number PTA-123014, wherein the *Brassica carinata* variety comprises a desired trait, the method comprising introducing a DNA construct conferring the desired trait into a plant of cultivar AGR044-3A22, wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector, and wherein the DNA construct comprises a transgene.

In another embodiment, the invention provides a method of producing a *Brassica carinata* variety produced from *Brassica carinata* cultivar AGR044-3A22, wherein a representative sample of the seed has been deposited under ATCC Accession number PTA-123014, wherein the *Brassica carinata* variety comprises a desired trait, the method comprising introducing a DNA construct conferring the desired trait into a plant of cultivar AGR044-3A22, and wherein the DNA construct comprises an RNAi construct.

In another embodiment, the invention provides a method of producing a *Brassica carinata* variety produced from *Brassica carinata* cultivar AGR044-3A22, wherein a representative sample of the seed has been deposited under ATCC Accession number PTA-123014, wherein the *Brassica carinata* variety comprises a desired trait, the method comprising introducing a DNA construct conferring the desired trait into a plant of cultivar AGR044-3A22, wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector, and wherein the DNA construct comprises an RNAi construct.

In another embodiment, the invention provides any one of the above methods, wherein the *Brassica carinata* variety comprises the desired trait and essentially all of the physiological and morphological characteristics of cultivar AGR044-3A22, when grown in the same location under the same environmental conditions.

In another embodiment, the invention provides any one of the above methods, wherein the desired trait is selected from the group consisting of male sterility, disease resistance, fungal resistance, pest resistance, herbicide tolerance, abiotic stress tolerance, and altered metabolism.

In another embodiment, the invention provides any one of the above methods, wherein the desired trait is herbicide tolerance and the tolerance is conferred to a herbicide selected from but not limited to the group consisting of glyphosate, glufosinate, imidazolinones, and auxin analogues such as 2,4-D and dicamba.

In another embodiment, the invention provides a plant, or part thereof, or seed of a *Brassica carinata* variety produced by any one of the above methods.

In another embodiment, the invention provides use of a plant of *Brassica carinata* cultivar AGR044-3A22, wherein a representative sample of said seed has been deposited under ATCC Accession number PTA-123014, to produce a *Brassica carinata* variety comprising a desired trait, wherein the desired trait is conferred by a DNA construct.

In another embodiment, the invention provides use of a plant of *Brassica carinata* cultivar AGR044-3A22, wherein a representative sample of said seed has been deposited under ATCC Accession number PTA-123014, to produce a *Brassica carinata* variety comprising a desired trait, wherein the desired trait is conferred by a DNA construct, wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector.

In another embodiment, the invention provides use of a plant of *Brassica carinata* cultivar AGR044-3A22, wherein a representative sample of said seed has been deposited under ATCC Accession number PTA-123014, to produce a *Brassica carinata* variety comprising a desired trait, wherein the desired trait is conferred by a DNA construct, and wherein the DNA construct comprises a transgene.

In another embodiment, the invention provides use of a plant of *Brassica carinata* cultivar AGR044-3A22, wherein a representative sample of said seed has been deposited under ATCC Accession number PTA-123014, to produce a *Brassica carinata* variety comprising a desired trait, wherein the desired trait is conferred by a DNA construct, wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector, and wherein the DNA construct comprises a transgene.

In another embodiment, the invention provides use of a plant of *Brassica carinata* cultivar AGR044-3A22, wherein a representative sample of said seed has been deposited under ATCC Accession number PTA-123014, to produce a *Brassica carinata* variety comprising a desired trait, wherein the desired trait is conferred by a DNA construct, and wherein the DNA construct comprises an RNAi construct.

In another embodiment, the invention provides use of a plant of *Brassica carinata* cultivar AGR044-3A22, wherein a representative sample of said seed has been deposited under ATCC Accession number PTA-123014, to produce a *Brassica carinata* variety comprising a desired trait, wherein the desired trait is conferred by a DNA construct, wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector, and wherein the DNA construct comprises an RNAi construct.

In another embodiment, the invention provides any of the above uses, wherein the *Brassica carinata* variety comprises the desired trait and essentially all of the physiological and morphological characteristics of cultivar AGR044-3A22 when grown in the same location under the same environmental conditions.

In another embodiment, the invention provides any of the above uses, wherein the desired trait is selected from the group consisting of male sterility, disease resistance, fungal resistance, pest resistance, herbicide tolerance, abiotic stress tolerance, and altered metabolism.

In another embodiment, the invention provides any of the above uses, wherein the desired trait is herbicide tolerance and the tolerance is conferred to a herbicide selected from but not limited to the group consisting of glyphosate, glufosinate, imidazolinones, and auxin analogues such as 2,4-D and dicamba.

In another embodiment, the invention provides a cell of a plant of a *Brassica carinata* variety produced from cultivar AGR044-3A22, the seed of which has been deposited under ATCC Accession number PTA-123014, wherein the *Brassica carinata* variety comprises a desired trait, and wherein the *Brassica carinata* variety was produced by a method comprising introducing a DNA construct conferring the desired trait into a plant of cultivar AGR044-3A22.

In another embodiment, the invention provides a cell of a plant of a *Brassica carinata* variety produced from cultivar AGR044-3A22, the seed of which has been deposited under ATCC Accession number PTA-123014, wherein the *Brassica carinata* variety comprises a desired trait, and wherein the *Brassica carinata* variety was produced by a method comprising introducing a DNA construct conferring the desired trait into a plant of cultivar AGR044-3A22, wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector.

In another embodiment, the invention provides a cell of a plant of a *Brassica carinata* variety produced from cultivar AGR044-3A22, the seed of which has been deposited under ATCC Accession number PTA-123014, wherein the *Brassica carinata* variety comprises a desired trait, and wherein the *Brassica carinata* variety was produced by a method comprising introducing a DNA construct conferring the desired trait into a plant of cultivar AGR044-3A22, and wherein the DNA construct comprises a transgene.

In another embodiment, the invention provides a cell of a plant of a *Brassica carinata* variety produced from cultivar AGR044-3A22, the seed of which has been deposited under ATCC Accession number PTA-123014, wherein the *Brassica carinata* variety comprises a desired trait, and wherein the *Brassica carinata* variety was produced by a method comprising introducing a DNA construct conferring the desired trait into a plant of cultivar AGR044-3A22, wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector, and wherein the DNA construct comprises a transgene.

In another embodiment, the invention provides a cell of a plant of a *Brassica carinata* variety produced from cultivar AGR044-3A22, the seed of which has been deposited under ATCC Accession number PTA-123014, wherein the *Brassica carinata* variety comprises a desired trait, and wherein the *Brassica carinata* variety was produced by a method comprising introducing a DNA construct conferring the desired trait into a plant of cultivar AGR044-3A22, and wherein the DNA construct comprises an RNAi construct.

In another embodiment, the invention provides a cell of a plant of a *Brassica carinata* variety produced from cultivar AGR044-3A22, the seed of which has been deposited under ATCC Accession number PTA-123014, wherein the *Brassica carinata* variety comprises a desired trait, and wherein the *Brassica carinata* variety was produced by a method comprising introducing a DNA construct conferring the desired trait into a plant of cultivar AGR044-3A22, wherein the DNA construct is introduced using polyethylene glycol (PEG) mediated DNA uptake, electroporation, ballistic infiltration using DNA coated microprojectiles (gene gun), an *Agrobacterium* infiltration based vector, or a plant virus based vector, and wherein the DNA construct comprises an RNAi construct.

In another embodiment, the invention provides any of the above cells, wherein the *Brassica carinata* variety comprises the desired trait and essentially all of the physiological and morphological characteristics of cultivar AGR044-3A22 when grown in the same location under the same environmental conditions.

In another embodiment, the invention provides any of the above cells, wherein the desired trait is selected from the group consisting of male sterility, disease resistance, fungal resistance, pest resistance, herbicide tolerance, abiotic stress tolerance, and altered metabolism.

In another embodiment, the invention provides any of the above cells, wherein the desired trait is herbicide tolerance and the tolerance is conferred to a herbicide selected from but not limited to the group consisting of glyphosate, glufosinate, imidazolinones, and auxin analogues such as 2,4-D and dicamba.

5.2.10 Methods of and Uses for Introducing a Desired Trait by an Initial Cross and then Pedigree Selection, and Cells, Plants and Seeds Produced Therefrom In another embodiment, the invention provides a method of producing a *Brassica carinata* variety produced from *Brassica carinata* cultivar AGR044-3A22, wherein a representative sample of the seed has been deposited under ATCC Accession number PTA-123014, and wherein the *Brassica carinata* variety comprises a desired trait, the method comprising the steps of: (a) crossing a plant of cultivar AGR044-3A22 with another *Brassica carinata* variety comprising the desired trait; (b) growing the resultant F1 hybrid seed and selecting one or more progeny plants that have the desired trait; (c) selfing the progeny plants that have the desired trait to produce further progeny seed; and (d) growing the further progeny seed and selecting further progeny plants that have the desired trait to produce the *Brassica carinata* variety produced from cultivar AGR044-3A22.

In another embodiment, the invention provides a method of producing a *Brassica carinata* variety produced from *Brassica carinata* cultivar AGR044-3A22, wherein a representative sample of the seed has been deposited under ATCC Accession number PTA-123014, and wherein the *Brassica carinata* variety comprises a desired trait, the method comprising the steps of: (a) crossing a plant of cultivar AGR044-3A22 with another *Brassica carinata* variety comprising the desired trait; (b) growing the resultant F1 hybrid seed and selecting one or more progeny plants that have the desired trait; (c) selfing the progeny plants that have the desired trait to produce further progeny seed; and (d) growing the further progeny seed and selecting further progeny plants that have the desired trait to produce the *Brassica carinata* variety produced from cultivar AGR044-3A22; wherein steps (c) and (d) are repeated until the *Brassica carinata* variety produced from cultivar AGR044-3A22 has the desired trait and essentially all of the physiological and morphological characteristics of cultivar AGR044-3A22 when grown in the same location under the same environmental conditions.

In another embodiment, the invention provides any one of the above methods wherein the desired trait is selected from the group consisting of male sterility, disease resistance, fungal resistance, pest resistance, herbicide tolerance, abiotic stress tolerance, and altered metabolism.

In another embodiment, the invention provides any one of the above methods, wherein the desired trait is herbicide tolerance and the tolerance is conferred to a herbicide selected from but not limited to the group consisting of glyphosate, glufosinate, imidazolinones, and auxin analogues such as 2,4-D and dicamba.

In another embodiment, the invention provides a plant, or part thereof, or seed of a *Brassica carinata* variety produced by any one of the above methods.

In another embodiment, the invention provides a cell of a plant of a *Brassica carinata* variety produced from cultivar AGR044-3A22, the seed of which has been deposited under ATCC Accession number PTA-123014, wherein the *Brassica carinata* variety comprises a desired trait, and wherein the *Brassica carinata* variety was produced by a method comprising the steps of: (a) crossing a plant of cultivar AGR044-3A22 with a plant of another *Brassica carinata* variety comprising the desired trait; (b) growing the resultant F1 hybrid seed and selecting one or more progeny plants that have the desired trait; (c) selfing the progeny plants that have the desired trait to produce further progeny plants; and (d) growing the resultant further progeny plants and selecting further progeny plants that have the desired trait to produce the *Brassica carinata* variety produced from cultivar AGR044-3A22.

In another embodiment, the invention provides a cell of a plant of a *Brassica carinata* variety produced from cultivar AGR044-3A22, the seed of which has been deposited under ATCC Accession number PTA-123014, wherein the *Brassica carinata* variety comprises a desired trait, and wherein the *Brassica carinata* variety was produced by a method comprising the steps of: (a) crossing a plant of cultivar AGR044-3A22 with a plant of another *Brassica carinata* variety comprising the desired trait; (b) growing the resultant F1 hybrid seed and selecting one or more progeny plants that have the desired trait; (c) selfing the progeny plants that have the desired trait to produce further progeny plants; and (d) growing the resultant further progeny plants and selecting further progeny plants that have the desired trait to produce the *Brassica carinata* variety produced from cultivar AGR044-3A22; wherein steps (c) and (d) are repeated until the *Brassica carinata* variety produced from cultivar AGR044-3A22 has the desired trait and essentially all of the physiological and morphological characteristics of cultivar AGR044-3A22 when grown in the same location under the same environmental conditions.

In another embodiment, the invention provides a cell of a plant of a *Brassica carinata* variety produced from cultivar AGR044-3A22, the seed of which has been deposited under ATCC Accession number PTA-123014, wherein the *Brassica carinata* variety comprises a desired trait, and wherein the *Brassica carinata* variety was produced by a method comprising the steps of: (a) crossing a plant of cultivar AGR044-3A22 with a plant of another *Brassica carinata* variety comprising the desired trait; (b) growing the resultant F1 hybrid seed and selecting one or more progeny plants that have the desired trait; (c) selfing the progeny plants that have the desired trait to produce further progeny plants; and (d) growing the resultant further progeny plants and selecting further progeny plants that have the desired trait to produce the *Brassica carinata* variety produced from cultivar AGR044-3A22; wherein the desired trait is selected from the group consisting of male sterility, disease resistance, fungal resistance, pest resistance, herbicide tolerance, abiotic stress tolerance, and altered metabolism.

In another embodiment, the invention provides a cell of a plant of a *Brassica carinata* variety produced from cultivar AGR044-3A22, the seed of which has been deposited under ATCC Accession number PTA-123014, wherein the *Brassica carinata* variety comprises a desired trait, and wherein the *Brassica carinata* variety was produced by a method comprising the steps of: (a) crossing a plant of cultivar AGR044-3A22 with a plant of another *Brassica carinata* variety comprising the desired trait; (b) growing the resultant F1 hybrid seed and selecting one or more progeny plants that have the desired trait; (c) selfing the progeny plants that have the desired trait to produce further progeny plants; and (d) growing the resultant further progeny plants and selecting further progeny plants that have the desired trait to produce the *Brassica carinata* variety produced from cultivar AGR044-3A22; wherein steps (c) and (d) are repeated until the *Brassica carinata* variety produced from cultivar AGR044-3A22 has the desired trait and essentially all of the physiological and morphological characteristics of cultivar AGR044-3A22 when grown in the same location under the same environmental conditions, and wherein the desired trait is selected from the group consisting of male sterility, disease resistance, fungal resistance, pest resistance, herbicide tolerance, abiotic stress tolerance, and altered metabolism.

In another embodiment, the invention provides a cell of a plant of a *Brassica carinata* variety produced from cultivar AGR044-3A22, the seed of which has been deposited under ATCC Accession number PTA-123014, wherein the *Brassica carinata* variety comprises a desired trait, and wherein the *Brassica carinata* variety was produced by a method comprising the steps of: (a) crossing a plant of cultivar AGR044-3A22 with a plant of another *Brassica carinata* variety comprising the desired trait; (b) growing the resultant F1 hybrid seed and selecting one or more progeny plants that have the desired trait; (c) selfing the progeny plants that have the desired trait to produce further progeny plants; and (d) growing the resultant further progeny plants and selecting further progeny plants that have the desired trait to produce the *Brassica carinata* variety produced from cultivar AGR044-3A22; wherein the desired trait is herbicide tolerance and the tolerance is conferred to a herbicide selected from but not limited to the group consisting of glyphosate, glufosinate, imidazolinones, and auxin analogues such as 2,4-D and dicamba.

In another embodiment, the invention provides a cell of a plant of a *Brassica carinata* variety produced from cultivar AGR044-3A22, the seed of which has been deposited under ATCC Accession number PTA-123014, wherein the *Brassica carinata* variety comprises a desired trait, and wherein the *Brassica carinata* variety was produced by a method comprising the steps of: (a) crossing a plant of cultivar AGR044-3A22 with a plant of another *Brassica carinata* variety comprising the desired trait; (b) growing the resultant F1 hybrid seed and selecting one or more progeny plants that have the desired trait; (c) selfing the progeny plants that have the desired trait to produce further progeny plants; and (d) growing the resultant further progeny plants and selecting further progeny plants that have the desired trait to produce the *Brassica carinata* variety produced from cultivar AGR044-3A22; wherein steps (c) and (d) are repeated until the *Brassica carinata* variety produced from cultivar AGR044-3A22 has the desired trait and essentially all of the physiological and morphological characteristics of cultivar AGR044-3A22 when grown in the same location under the same environmental conditions; and wherein the desired trait is herbicide tolerance and the tolerance is conferred to a herbicide selected from but not limited to the group consisting of glyphosate, glufosinate, imidazolinones, and auxin analogues such as 2,4-D and dicamba.

5.2.11 Mutagenesis

In one aspect, the present invention includes the introduction of a desired trait into *Brassica carinata* cultivar AGR044-3A22, wherein a representative sample of the seed has been deposited under ATCC Accession number PTA-123014, to produce a *Brassica carinata* variety comprising the desired trait, wherein the desired trait is introduced by mutagenesis.

Any means of mutagenesis can potentially be used, including the mutagenic agents ethyl methanesulfonate, N-ethyl-N-nitrosourea, ionizing radiation such as x-ray or gamma, or ultraviolet radiation.

The mutagenization can be of a variety of parts of the plants, including a seed, seedling, or microspore. Mutagenized microspores can then be used to generate doubled haploid plants (see above). Seedlings or microspores are exposed to the mutagenic agent and then the surviving fraction are allowed to develop into mature plants. In some cases, the mutagenized plantlets or embryos (in the case of microspore mutagenesis) may be exposed to selection in order to enrich for a particular phenotype. This technique can be used to develop varieties with a desired trait, such as resistance to a herbicide, an altered seed oil profile, increased tolerance to disease, or abiotic stress.

In another embodiment, the invention provides a method of producing a *Brassica carinata* variety produced from *Brassica carinata* cultivar AGR044-3A22, wherein a representative sample of the seed has been deposited under ATCC Accession number PTA-123014, and wherein the *Brassica carinata* variety comprises a desired trait, the method comprising exposing seedlings or microspores to a mutagenic agent and allowing the surviving fraction to develop into mature plants.

In another embodiment, the invention provides a method of producing a *Brassica carinata* variety produced from *Brassica carinata* cultivar AGR044-3A22, wherein a representative sample of the seed has been deposited under ATCC Accession number PTA-123014, and wherein the *Brassica carinata* variety comprises a desired trait, the method comprising exposing seedlings or microspores to a mutagenic agent and allowing the surviving fraction to develop into mature plants, and wherein the mutagenic agent is ethyl methanesulfonate, N-ethyl-N-nitrosourea, ionizing radiation such as x-ray or gamma, or ultraviolet radiation.

In another embodiment, the invention provides a plant, or part thereof, or seed of a *Brassica carinata* variety produced by any of the above methods.

In another embodiment, the invention provides use of a plant of *Brassica carinata* cultivar AGR044-3A22, wherein a representative sample of said seed has been deposited under ATCC Accession number PTA-123014, to produce a *Brassica carinata* variety comprising a desired trait, wherein the desired trait is introduced by exposing seedlings or microspores to a mutagenic agent.

In another embodiment, the invention provides use of a plant of *Brassica carinata* cultivar AGR044-3A22, wherein a representative sample of said seed has been deposited under ATCC Accession number PTA-123014, to produce a *Brassica carinata* variety comprising a desired trait, wherein the desired trait is introduced by exposing seedlings or microspores to a mutagenic agent, and wherein the mutagenic agent is ethyl methanesulfonate, N-ethyl-N-nitrosourea, ionizing radiation such as x-ray or gamma, or ultraviolet radiation.

In another embodiment, the invention provides a cell of a plant of a *Brassica carinata* variety produced from cultivar AGR044-3A22, wherein a representative sample of said seed has been deposited under ATCC Accession number PTA-123014, wherein the *Brassica carinata* variety comprises a desired trait, and wherein the *Brassica carinata* variety is produced by a method comprising exposing seedlings or microspores to a mutagenic agent and allowing the surviving fraction to develop into mature plants.

In another embodiment, the invention provides a cell of a plant of a *Brassica carinata* variety produced from cultivar AGR044-3A22, wherein a representative sample of said seed has been deposited under ATCC Accession number PTA-123014, wherein the *Brassica carinata* variety comprises a desired trait, and wherein the *Brassica carinata* variety is produced by a method comprising exposing seedlings or microspores to a mutagenic agent and allowing the surviving fraction to develop into mature plants, wherein the mutagenic agent is ethyl methanesulfonate, N-ethyl-N-nitrosourea, ionizing radiation such as x-ray or gamma, or ultraviolet radiation.

5.2.12 Methods of or Uses for Producing a *Carinata* Variety by Outcrossing (Interspecific or Wide Crossing), and Cells, Plants, Seeds Produced Therefrom Where no *Brassica carinata* variety has a specific desired trait, outcrossing (interspecific or wide crossing) can be used where the trait is found in another Brassicaceae species, such as, for example, *Brassica napus, Brassica juncea, Brassica oleracea, Brassica rapa*, or *Brassica nigra*.

In another embodiment, the invention provides a method of producing a *carinata* variety produced from *Brassica carinata* cultivar AGR044-3A22, wherein a representative sample of the seed has been deposited under ATCC Accession number PTA-123014, and wherein the *carinata* variety comprises a desired trait, the method comprising: (a) crossing a plant of cultivar AGR044-3A22 with a plant of another Brassicaceae species comprising the desired trait; (b) using embryo rescue techniques to recover viable F1 plants from the cross or growing F1 seeds to produce F1 plants; (c) selfing the F1 plants that have the desired trait and *carinata* character; (d) using embryo rescue techniques to recover viable F2 plants or growing F2 seeds to produce F2 plants; (e) selfing the F2 plants that have the desired trait and *carinata* character; (f) using embryo rescue techniques to recover viable F3 plants or growing F3 seeds to produce progeny plants; (g) selfing the progeny plants that have the desired trait and *carinata* character to produce further progeny plants; and (h) selecting the progeny plants with the desired trait and *carinata* character to produce the *carinata* variety produced from cultivar AGR044-3A22.

In another embodiment, the invention provides a method of producing a *carinata* variety produced from *Brassica carinata* cultivar AGR044-3A22, wherein a representative sample of the seed has been deposited under ATCC Accession number PTA-123014, and wherein the *carinata* variety comprises a desired trait, the method comprising: (a) crossing a plant of cultivar AGR044-3A22 with a plant of another Brassicaceae species comprising the desired trait; (b) using embryo rescue techniques to recover viable F1 plants from the cross or growing F1 seeds to produce F1 plants; (c) selfing the F1 plants that have the desired trait and *carinata* character; (d) using embryo rescue techniques to recover viable F2 plants or growing F2 seeds to produce F2 plants; (e) selfing the F2 plants that have the desired trait and *carinata* character; (f) using embryo rescue techniques to recover viable F3 plants or growing F3 seeds to produce progeny plants; (g) selfing the progeny plants that have the desired trait and *carinata* character to produce further progeny plants; and (h) selecting the progeny plants with the desired trait and *carinata* character to produce the *carinata* variety produced from cultivar AGR044-3A22; wherein steps (g) and (h) are repeated until the *carinata* variety produced from cultivar AGR044-3A22 has the desired trait and essentially all of the physiological and morphological characteristics of cultivar AGR044-3A22 when grown in the same location under the same environmental conditions.

In another embodiment, the invention provides any of the above methods, wherein the desired trait is selected from the group consisting of male sterility, disease resistance, fungal resistance, pest resistance, herbicide tolerance, abiotic stress tolerance, and altered metabolism.

In another embodiment, the invention provides any of the above methods, wherein the desired trait is herbicide tolerance and the tolerance is conferred to a herbicide selected from but not limited to the group consisting of glyphosate, glufosinate, imidazolinones, and auxin analogues such as 2,4-D and dicamba.

In another embodiment, the invention provides any of the above methods, wherein the method further comprises producing a doubled haploidy variety from the *carinata* variety.

In another embodiment, the invention provides a plant, or part thereof, or seed of a *carinata* variety produced by any of the above methods.

In another embodiment, the invention provides use of a plant of *Brassica carinata* cultivar AGR044-3A22, wherein a representative sample of said seed has been deposited under ATCC Accession number PTA-123014, to produce a *carinata* variety comprising a desired trait, wherein the desired trait is introduced by crossing a plant of cultivar AGR044-3A22 with a plant of another Brassicaceae species comprising the desired trait.

In another embodiment, the invention provides use of a plant of *Brassica carinata* cultivar AGR044-3A22, wherein a representative sample of said seed has been deposited under ATCC Accession number PTA-123014, to produce a *carinata* variety comprising a desired trait, wherein the desired trait is introduced by crossing a plant of cultivar AGR044-3A22 with a plant of another Brassicaceae species comprising the desired trait, and wherein the *carinata* variety produced from cultivar AGR044-3A22 has the desired trait and essentially all of the physiological and morphological characteristics of cultivar AGR044-3A22 when grown in the same location under the same environmental conditions.

In another embodiment, the invention provides use of a plant of *Brassica carinata* cultivar AGR044-3A22, wherein a representative sample of said seed has been deposited under ATCC Accession number PTA-123014, to produce a *carinata* variety comprising a desired trait, wherein the desired trait is introduced by crossing a plant of cultivar AGR044-3A22 with a plant of another Brassicaceae species comprising the desired trait, and wherein the desired trait is selected from the group consisting of male sterility, disease resistance, fungal resistance, pest resistance, herbicide tolerance, abiotic stress tolerance, and altered metabolism.

In another embodiment, the invention provides use of a plant of *Brassica carinata* cultivar AGR044-3A22, wherein a representative sample of said seed has been deposited under ATCC Accession number PTA-123014, to produce a *carinata* variety comprising a desired trait, wherein the desired trait is introduced by crossing a plant of cultivar AGR044-3A22 with a plant of another Brassicaceae species comprising the desired trait, and wherein the *carinata* variety produced from cultivar AGR044-3A22 has the desired trait and essentially all of the physiological and morphological characteristics of cultivar AGR044-3A22 when grown in the same location under the same environmental conditions, and wherein the desired trait is selected from the group consisting of male sterility, disease resistance, fungal resistance, pest resistance, herbicide tolerance, abiotic stress tolerance, and altered metabolism.

In another embodiment, the invention provides use of a plant of *Brassica carinata* cultivar AGR044-3A22, wherein a representative sample of said seed has been deposited under ATCC Accession number PTA-123014, to produce a *carinata* variety comprising a desired trait, wherein the desired trait is introduced by crossing a plant of cultivar AGR044-3A22 with a plant of another Brassicaceae species comprising the desired trait, and wherein the desired trait is herbicide tolerance and the tolerance is conferred to a herbicide selected from but not limited to the group consisting of glyphosate, glufosinate, imidazolinones, and auxin analogues such as 2,4-D and dicamba.

In another embodiment, the invention provides use of a plant of *Brassica carinata* cultivar AGR044-3A22, wherein a representative sample of said seed has been deposited under ATCC Accession number PTA-123014, to produce a *carinata* variety comprising a desired trait, wherein the desired trait is introduced by crossing a plant of cultivar AGR044-3A22 with a plant of another Brassicaceae species comprising the desired trait, and wherein the *carinata* variety produced from cultivar AGR044-3A22 has the desired trait and essentially all of the physiological and morphological characteristics of cultivar AGR044-3A22 when grown in the same location under the same environmental conditions, and wherein the desired trait is herbicide tolerance and the tolerance is conferred to a herbicide selected from but not limited to the group consisting of glyphosate, glufosinate, imidazolinones, and auxin analogues such as 2,4-D and dicamba.

In another embodiment, the invention provides a cell of a plant of a *carinata* variety comprising a desired trait, wherein the *carinata* variety is produced by a method comprising: (a) crossing a plant of cultivar AGR044-3A22 with a plant of another Brassicaceae species comprising the desired trait; (b) using embryo rescue techniques to recover viable F1 plants from the cross or growing F1 seeds to produce F1 plants; (c) selfing the F1 plants that have the desired trait and *carinata* character; (d) using embryo rescue techniques to recover viable F2 plants or growing F2 seeds to produce F2 plants; (e) selfing the F2 plants that have the desired trait and *carinata* character; (f) using embryo rescue techniques to recover viable F3 plants or growing F3 seeds to produce progeny plants; (g) selfing the progeny plants that have the desired trait and *carinata* character to produce further progeny plants; and (h) selecting the progeny plants with the desired trait and *carinata* character to produce the *carinata* variety produced from cultivar AGR044-3A22.

In another embodiment, the invention provides a cell of a plant of a *carinata* variety comprising a desired trait, wherein the *carinata* variety is produced by a method comprising: (a) crossing a plant of cultivar AGR044-3A22 with a plant of another Brassicaceae species comprising the desired trait; (b) using embryo rescue techniques to recover viable F1 plants from the cross or growing F1 seeds to produce F1 plants; (c) selfing the F1 plants that have the desired trait and *carinata* character; (d) using embryo rescue techniques to recover viable F2 plants or growing F2 seeds to produce F2 plants; (e) selfing the F2 plants that have the desired trait and *carinata* character; (f) using embryo rescue techniques to recover viable F3 plants or growing F3 seeds to produce progeny plants; (g) selfing the progeny plants that have the desired trait and *carinata* character to produce further progeny plants; and (h) selecting the progeny plants with the desired trait and *carinata* character to produce the *carinata* variety produced from cultivar AGR044-3A22; wherein steps (g) and (h) are repeated until the *carinata* variety produced from cultivar AGR044-3A22 has the desired trait and essentially all of the physiological and morphological characteristics of cultivar AGR044-3A22 when grown in the same location under the same environmental conditions.

In another embodiment, the invention provides a cell of a plant of a *carinata* variety comprising a desired trait, wherein the *carinata* variety is produced by a method comprising: (a) crossing a plant of cultivar AGR044-3A22 with a plant of another Brassicaceae species comprising the desired trait; (b) using embryo rescue techniques to recover viable F1 plants from the cross or growing F1 seeds to produce F1 plants; (c) selfing the F1 plants that have the desired trait and *carinata* character; (d) using embryo rescue techniques to recover viable F2 plants or growing F2 seeds to produce F2 plants; (e) selfing the F2 plants that have the desired trait and *carinata* character; (f) using embryo rescue techniques to recover viable F3 plants or growing F3 seeds to produce progeny plants; (g) selfing the progeny plants that have the desired trait and *carinata* character to produce further progeny plants; and (h) selecting the progeny plants with the desired trait and *carinata* character to produce the *carinata* variety produced from cultivar AGR044-3A22; wherein the desired trait is selected from the group consisting of male sterility, disease resistance, fungal resistance, pest resistance, herbicide tolerance, abiotic stress tolerance, and altered metabolism.

In another embodiment, the invention provides a cell of a plant of a *carinata* variety comprising a desired trait, wherein the *carinata* variety is produced by a method comprising: (a) crossing a plant of cultivar AGR044-3A22 with a plant of another Brassicaceae species comprising the desired trait; (b) using embryo rescue techniques to recover viable F1 plants from the cross or growing F1 seeds to produce F1 plants; (c) selfing the F1 plants that have the desired trait and *carinata* character; (d) using embryo rescue techniques to recover viable F2 plants or growing F2 seeds to produce F2 plants; (e) selfing the F2 plants that have the desired trait and *carinata* character; (f) using embryo rescue techniques to recover viable F3 plants or growing F3 seeds to produce progeny plants; (g) selfing the progeny plants that have the desired trait and *carinata* character to produce further progeny plants; and (h) selecting the progeny plants with the desired trait and *carinata* character to produce the *carinata* variety produced from cultivar AGR044-3A22; wherein steps (g) and (h) are repeated until the *carinata* variety produced from cultivar AGR044-3A22 has the desired trait and essentially all of the physiological and morphological characteristics of cultivar AGR044-3A22 when grown in the same location under the same environmental conditions, and wherein the desired trait is selected from the group consisting of male sterility, disease resistance, fungal resistance, pest resistance, herbicide tolerance, abiotic stress tolerance, and altered metabolism.

In another embodiment, the invention provides a cell of a plant of a *carinata* variety comprising a desired trait, wherein the *carinata* variety is produced by a method comprising: (a) crossing a plant of cultivar AGR044-3A22 with a plant of another Brassicaceae species comprising the desired trait; (b) using embryo rescue techniques to recover viable F1 plants from the cross or growing F1 seeds to produce F1 plants; (c) selfing the F1 plants that have the desired trait and *carinata* character; (d) using embryo rescue techniques to recover viable F2 plants or growing F2 seeds to produce F2 plants; (e) selfing the F2 plants that have the desired trait and *carinata* character; (f) using embryo rescue techniques to recover viable F3 plants or growing F3 seeds to produce progeny plants; (g) selfing the progeny plants that have the desired trait and *carinata* character to produce further progeny plants; and (h) selecting the progeny plants with the desired trait and *carinata* character to produce the *carinata* variety produced from cultivar AGR044-3A22; wherein the desired trait is herbicide tolerance and the tolerance is conferred to a herbicide selected from but not limited to the group consisting of glyphosate, glufosinate, imidazolinones, and auxin analogues such as 2,4-D and dicamba.

In another embodiment, the invention provides a cell of a plant of a *carinata* variety comprising a desired trait, wherein the *carinata* variety is produced by a method comprising: (a) crossing a plant of cultivar AGR044-3A22 with a plant of another Brassicaceae species comprising the desired trait; (b) using embryo rescue techniques to recover viable F1 plants from the cross or growing F1 seeds to produce F1 plants; (c) selfing the F1 plants that have the desired trait and *carinata* character; (d) using embryo rescue techniques to recover viable F2 plants or growing F2 seeds to produce F2 plants; (e) selfing the F2 plants that have the desired trait and *carinata* character; (f) using embryo rescue techniques to recover viable F3 plants or growing F3 seeds to produce progeny plants; (g) selfing the progeny plants that have the desired trait and *carinata* character to produce further progeny plants; and (h) selecting the progeny plants with the desired trait and *carinata* character to produce the *carinata* variety produced from cultivar AGR044-3A22; wherein steps (g) and (h) are repeated until the *carinata* variety produced from cultivar AGR044-3A22 has the desired trait and essentially all of the physiological and morphological characteristics of cultivar AGR044-3A22 when grown in the same location under the same environmental conditions, and wherein the desired trait is herbicide tolerance and the tolerance is conferred to a herbicide selected from but not limited to the group consisting of glyphosate, glufosinate, imidazolinones, and auxin analogues such as 2,4-D and dicamba.

5.2.13 Commercial Crops and Commercial Plant Products

In another embodiment, the invention provides a method of producing a commercial plant product, the method comprising growing a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, to produce a commercial crop, and producing said commercial plant product from the commercial crop.

In another embodiment, the invention provides a method of producing a commercial plant product, the method comprising growing a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, to produce a commercial crop, and producing said commercial plant product from the commercial crop, wherein the commercial plant product comprises oil, meal, or protein isolate.

In another embodiment, the invention provides a method of producing a commercial plant product, the method comprising growing a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, to produce a commercial crop, and producing said commercial plant product from the commercial crop, wherein the commercial plant product comprises a biofumigant.

In another embodiment, the invention provides a commercial plant product produced by a method comprising growing a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, to produce a commercial crop, and producing said commercial plant product from the commercial crop.

In another embodiment, the invention provides a commercial plant product produced by a method comprising growing a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, to produce a commercial crop, and producing said commercial plant product from the commercial crop, wherein the commercial plant product comprises oil, meal, or protein isolate.

In another embodiment, the invention provides oil, meal, or protein isolate produced by a method comprising growing a plant of *Brassica carinata* cultivar AGR044-3A22 produced from the seed of *Brassica carinata* cultivar designated AGR044-3A22, wherein a representative sample of the seed has been deposited under ATCC Accession number PTA-123014, to produce a commercial crop, and producing the oil, meal, or protein isolate from the commercial crop.

In another embodiment, the invention provides crushed, non-viable seed of *Brassica carinata* cultivar AGR044-3A22, wherein a representative sample of said seed has been deposited under ATCC Accession number PTA-123014.

In another embodiment, the invention provides use of a plant of *Brassica carinata* cultivar AGR044-3A22, wherein a representative sample of said seed has been deposited under ATCC Accession number PTA-123014, to produce a commercial crop.

In another embodiment, the invention provides use of a plant of *Brassica carinata* cultivar AGR044-3A22, wherein a representative sample of said seed has been deposited under ATCC Accession number PTA-123014, to produce a commercial plant product.

In another embodiment, the invention provides use of a plant of *Brassica carinata* cultivar AGR044-3A22, wherein a representative sample of said seed has been deposited under ATCC Accession number PTA-123014, to produce a commercial plant product, wherein the commercial plant product comprises oil, meal, or protein isolate.

In another embodiment, the invention provides crushed, non-viable seed of a *Brassica carinata* variety produced from *Brassica carinata* cultivar AGR044-3A22, wherein a representative sample of said seed has been deposited under ATCC Accession number PTA-123014.

In another embodiment, the invention provides use of a plant of a *Brassica carinata* variety produced from *Brassica carinata* cultivar AGR044-3A22, wherein a representative sample of said seed has been deposited under ATCC Accession number PTA-123014, to produce a commercial crop.

In another embodiment, the invention provides use of a plant of a *Brassica carinata* variety produced from *Brassica carinata* cultivar AGR044-3A22, wherein a representative sample of said seed has been deposited under ATCC Accession number PTA-123014, to produce a commercial plant product.

In another embodiment, the invention provides use of a plant of a *Brassica carinata* variety produced from *Brassica carinata* cultivar AGR044-3A22, wherein a representative sample of said seed has been deposited under ATCC Accession number PTA-123014, to produce a commercial plant product, wherein the commercial plant product comprises oil, meal, or protein isolate.

5.3 Characteristics of AGR044-312D and AGR044-3A22

Example 1: AGR044-312D and AGR044-3A22 Yield Performance in North Dakota, South Dakota and Saskatchewan Yield trials were carried out for AGR044-312D at Winner, S. Dak.; Hettinger, N. Dak.; Moosomin, SK; and Vanguard, SK during the summer of 2015 in small plots using a three replicate randomized complete block design. These tests including 312D were designated "PYT A". This same experimental design was used for yield trials including AGR044-3A22, and data for two reliable sites was collected at Winner, S. Dak. and Tioga, N. Dak. Yields were calculated from the mean of replicate plots of the test variety and expressed as a percentage of the mean yield of the check varieties in the same trial (A110 and A120, the current commercial varieties, were used as checks).

Table 1 records seed yield relative to the A110 check in yield testing in 2015. In the Hettinger trial, AGR044-312D yielded substantially higher than both of the commercial *carinata* check varieties; while in the Winner trial this variety yielded more than the A110 commercial check but not A120. In both Moosomin and Vanguard, AGR044-312D yielded lower than both A110 and A120. It should be noted that 312D has been tested as an improved variety for more southern geographies such as in the Southeast U.S. or South America. Therefore, yield data for AGR044-312D in these northern sites is not necessarily indicative of the full yield potential of this variety. For AGR044-3A22 in Tioga, yields substantially exceed both check lines, while at the Winner trial this variety yielded more than the A110 but not A120.

TABLE 1

AGR044-312D and -3A22 yields relative to checks in North Dakota, South Dakota and Saskatchewan yield trials (2015)

| | | Carinata variety | | | |
|---|---|---|---|---|---|
| Traits | Trials | 312D | 3A22 | A120 | A110 |
| Yield as % of A110 (Hettinger, ND) | Prelim A | 136 | n.d. | 118 | 100 |
| Yield as % of A110 (Winner, SD) | | 109 | n.d. | 113 | 100 |
| Yield as % of A110 (Moosomin SK) | | 86 | n.d. | 103 | 100 |
| Yield as % of A110 (Vanguard, SK) | | 84 | n.d. | 97 | 100 |
| Yield as % of A110 (Winner, SD) | Prelim B | n.d. | 105 | 106 | 100 |
| Yield as % of A110 (Tioga, SD) | | n.d. | 133 | 118 | 100 |
| Yield as % of A110 (Vanguard, SK) | | n.d. | n.d. | 108 | 100 |

Example 2: AGR044-312D and AGR044-3A22 Agronomic Traits in North Dakota, South Dakota and Saskatchewan Testing Observations were made of various distinguishing traits leaf, flower and silique colouration, plant height, as well as agronomic traits such as days to flower (DTF), days to maturity DTM). Table 2 summarizes these observations for the AGR044-312D variety and Table 3 for the AGR044-3A22 variety.

TABLE 2

AGR044-312D Unique plant traits (North Dakota, South Dakota and Saskatchewan, 2015)

| Trait | AGR044-312D | A120 | A110 |
|---|---|---|---|
| Moosomin - Flower Petal colour | yellow (<10% white) | yellow | yellow |
| Vanguard - Flower Petal colour | yellow (<10% white) | yellow | yellow |
| Hettinger - DTF | 54 | 54 | 54 |
| Moosomin - DTF | 50 | 53 | 52 |

TABLE 2-continued

AGR044-312D Unique plant traits (North Dakota, South Dakota and Saskatchewan, 2015)

| Trait | AGR044-312D | A120 | A110 |
|---|---|---|---|
| Vanguard - DTF | 58 | 58 | 62 |
| Vanguard - DTM | 112 | 112 | 117 |
| Moosomin - DTM | 97 | 100 | 99 |
| Tioga Maturity rating (taken August 10; rating 1 to 10, 10 being complete maturity | 8.7 | 6.7 | 6.3 |
| Vanguard - Canopy height (cm) | 93 | 109 | 106 |
| Hettinger - Height (cm) | 106 | 130 | 133 |
| Leaf colouration at bolting | Dark green | Bluish green | Bluish green |
| Incidence of purple silique coloration (due to anthocyanin) | Medium to high | low | low |

TABLE 3

AGR044-3A22 Unique plant traits (North Dakota, South Dakota and Saskatchewan, 2015)

| Trait | AGR044-3A22 | A120 | A110 |
|---|---|---|---|
| Winner - Flower Petal colour | yellow (<5% white) | yellow | yellow |
| Tioga - Flower Petal colour | yellow (<5% white) | yellow | yellow |
| Winner - DTF | 55 | 56 | 56 |
| Tioga Maturity rating (taken August 10; rating 1 to 10, 10 being complete maturity | 7.0 | 4.7 | 6.7 |
| Leaf colouration at bolting | Green | Bluish green | Bluish green |
| Incidence of purple silique coloration (due to anthocyanin) | Very low level | Low level mostly in leaf axil area | Low level mostly in leaf axil area |

Example 3: Seed Quality Characteristics of AGR044-312D and AGR044-3A22 in 2015 Testing (North Dakota, South Dakota and Saskatchewan)

Seed samples from each plot in the 2015 preliminary trial sites were used for seed quality data analysis. Seed quality estimates were obtained for AGR044-312D at Winner, S. Dak.; Moosomin, SK; and Vanguard, SK; and for AGR044-3A22 at Winner, S. Dak. and Tioga, N. Dak.

Seed oil, GSL (glucosinolate) content, protein content and fatty acid profile were determined by NIR analysis on a FOSS XDS™ Rapid Content Analyser fitted with an auto sampling unit. For NIR analysis, a minimum of 5 g of seed sample (cleaned and dried to approximately 5% moisture) was placed in a ring cup, tracking code recorded, and sample spectra collected at 0.5 nm increments, over the range of 400-2500 nm. Calibration was developed in-house by correlating the NIR spectra with experimentally-measured seed quality parameters of a diverse set of carinata experimental lines, representing as wide a spectrum of seed quality characteristics as could be found in this species (diverse range of oil contents, profiles, glucosinolate levels, seed colours, etc.). NIR values for oil content (% of whole seed) were validated using data obtained from NMR analysis of samples on an Oxford MARAN Ultra benchtop NMR system. NIR determination of seed Fatty-acid profile (and derived statistics, such as % SATS and % LCFA) was calibrated using Gas Chromatography of the Fatty-Acid Methyl Esters (FAMEs) using the protocol described by Taylor et al. (1992). NIR based glucosinolate determination was calibrated using Canadian Grains Commission data, a combination of the ISO 9167 method and their own NIR measurements. For calibration, seed samples were analyzed using our NIR instrument, the spectra collected and the experimental values recorded. The data set was then subjected to mathematical modeling to refine the spectra and the WinISI software package was used to determine the spectral regions most predictive of the desired parameters. Points providing >99.99% correlation with the experimental values (determined as described above) were selected from the spectral curve and used to develop the predictive equation.

Least square means of replicate seed oil and GSL content data were calculated and their standard errors compared via REML analysis to determine whether seed quality differences between tested carinata varieties were significant. Values not sharing a group letter (Tables 4 and 5) were significantly different at $P<0.05$, using the Student comparison of LS Mean method. All statistical analysis was performed using the JMP statistical analysis software (SAS)

Seed Oil Content:

As can be seen in Table 4, the mean oil content of AGR044-312D was consistently 3-4% lower than those of the check varieties A120 and A110 in three groups of yield trials carried out in N. Dakota, S. Dakota and Saskatchewan during the summer of 2015. The variety AGR044-3A22, was closer in oil content to the check lines. For this variety, comparison of the means using REML test showed no significant differences between AGR044-3A22, A120 and A110.

Glucosinolate Content:

As can be seen in Table 5, the varieties AGR044-312D and AGR044-3A22 clearly demonstrated a significantly lower seed GSL content relative to A110 and A120 seed. For AGR044-312D, decreases in GSL content of 18-23% relative to A110 and 19-28% relative to A120 were observed. For AGR044-3A22, decreases in GSL content of 27% relative to A110 and 32% relative to A120 were observed.

TABLE 4

Seed quality versus check lines; oil content of AGR044-312D and AGR044-3A22 compared with check lines in 2015 yield testing (North Dakota, South Dakota and Saskatchewan, 2015)

| Trial | No. sites | Name | Oil % (LS Mean) | Std Error | Group |
|---|---|---|---|---|---|
| PYT A | 3 | AAC A110 | 43.2 | 0.6 | ABC |
| PYT A | 3 | AAC A120 | 43.1 | 0.6 | ABC |
| PYT A | 3 | AGR044-312D | 39.5 | 0.5 | GHIJ |
| PYT B | 2 | AAC A110 | 44.6 | 0.6 | ABCD |
| PYT B | 2 | AAC A120 | 43.5 | 0.6 | DEFGH |
| PYT B | 2 | AGR044-3A22 | 44.4 | 0.7 | ABCDEF |

TABLE 5

Seed quality versus check lines; seed Glucosinolate content of AGR044-312D and AGR044-3A22 compared with check lines in 2015 yield testing (North Dakota, South Dakota and Saskatchewan)

| Trial | No. sites | Name | GSL (µmol/g) (LS Mean) | Std Error | Group |
|---|---|---|---|---|---|
| PYT A | 3 | AAC A110 | 92.9 | 3.4 | FGHI |
| PYT A | 3 | AAC A120 | 91.2 | 3.4 | FGH |

TABLE 5-continued

Seed quality versus check lines; seed Glucosinolate content of AGR044-312D and AGR044-3A22 compared with check lines in 2015 yield testing (North Dakota, South Dakota and Saskatchewan)

| Trial | No. sites | Name | GSL (μmol/g) (LS Mean) | Std Error | Group |
|---|---|---|---|---|---|
| PYT A | 3 | AGR044-312D | 73.9 | 3.1 | AB |
| PYT B | 2 | AAC A110 | 77.9 | 3.7 | IJKL |
| PYT B | 2 | AAC A120 | 83.4 | 3.7 | KL |
| PYT B | 2 | AGR044-3A22 | 57.1 | 4.5 | AC |

Protein:

*Brassica carinata* seed is known to contain appreciable levels of protein. When oil is extracted from the seed in commercial crushing operations, the remaining meal fraction can in itself be a valuable co-product, serving as a source of protein for use in animal feed applications. Therefore, in any assessment of new *carinata* varieties for commercial potential, seed protein content is an important consideration. Table 6 compares the protein contents of AGR044-312D and AGR044-3A22 with those of check lines A110 and A120 in seed harvested from 2015 field trials. The least square means estimate of AGR044-312D and AGR044-3A22 whole seed protein values was 26 to 27%; and for the checks it was 28 to 29% (Table 6).

TABLE 6

Seed quality versus check lines; seed protein content of AGR044-312D and AGR044-3A22 compared with check lines in 2015 yield testing (North Dakota, South Dakota and Saskatchewan)

| Trial | No. sites | Name | % Protein (LS Mean) | Std Error | Group |
|---|---|---|---|---|---|
| PYT A | 3 | AAC A110 | 28.4 | 0.6 | CDE |
| PYT A | 3 | AAC A120 | 27.9 | 0.6 | CDEF |

TABLE 6-continued

Seed quality versus check lines; seed protein content of AGR044-312D and AGR044-3A22 compared with check lines in 2015 yield testing (North Dakota, South Dakota and Saskatchewan)

| Trial | No. sites | Name | % Protein (LS Mean) | Std Error | Group |
|---|---|---|---|---|---|
| PYT A | 3 | AGR044-312D | 26.9 | 0.5 | FG |
| PYT B | 2 | AAC A110 | 28.1 | 0.6 | BCDEFG |
| PYT B | 2 | AAC A120 | 29.0 | 0.6 | BC |
| PYT B | 2 | AGR044-3A22 | 25.9 | 0.8 | IJKL |

Fatty Acid Profile:

The composition of *carinata* oil makes it suitable as an industrial feedstock in a number of biofuel manufacturing applications (see for example Gesch et al 2015, Wagid et al 2015). In particular, high levels of long and very long chain monounsaturated fatty acid content and a low proportion of saturated fatty acids are key definers of the current *carinata* profile and significant divergence from this profile in new *carinata* varieties would be problematic. Table 7 shows the fatty acid profile of AGR044-312D, AGR044-3A22 and the A110 and A120 check lines from grain harvested from 2015 trials carried out in North Dakota, South Dakota and Saskatchewan. As can be seen, the VLCFA erucic acid (C22.1) proportion in oil of both AGR044-312D and AGR044-3A22 falls very close to those of the commercial check lines in all trials. Similarly, the levels of saturated fatty acids in both AGR044-312D and AGR044-3A22 oil are close to those of the check varieties. The composition of the other main fatty acid constituents of AGR044-312D and AGR044-3A22 also do not deviate substantially from those of their check line counterparts. This it is expected that the physical properties of the AGR044-312D and AGR044-3A22 oil that are dependant on fatty acid composition should not differ greatly from those of the check lines.

TABLE 7

Fatty acid profile of oil from grain harvested in North Dakota, Soiuth Dakota and Saskatchewan trials (2015)

| Site | Name | SATS | SD | C18.1 | SD | C18.2 | SD | C18.3 | SD | C20.1 | SD | C22.1 | SD |
|---|---|---|---|---|---|---|---|---|---|---|---|---|---|
| Moosomin, SK | AAC A110 | 6.03 | 0.18 | 8.13 | 0.95 | 14.97 | 0.64 | 14.67 | 0.27 | 8.75 | 0.59 | 40.39 | 0.64 |
| Moosomin, SK | AAC A120 | 6.27 | 0.13 | 8.25 | 0.72 | 15.69 | 0.78 | 13.99 | 0.36 | 9.12 | 0.35 | 38.55 | 1.07 |
| Moosomin, SK | AGR044-312D | 6.11 | 0.08 | 10.14 | 1.21 | 16.31 | 0.30 | 12.91 | 0.14 | 9.42 | 0.26 | 41.46 | 0.70 |
| Vanguard, SK | AAC A110 | 6.41 | 0.24 | 13.83 | 1.21 | 16.09 | 1.12 | 13.39 | 0.67 | 10.04 | 0.28 | 34.90 | 2.23 |
| Vanguard, SK | AAC A120 | 6.24 | 0.13 | 13.26 | 1.36 | 15.70 | 0.42 | 12.99 | 0.39 | 10.43 | 0.43 | 36.77 | 1.23 |
| Vanguard, SK | AGR044-312D | 6.31 | 0.10 | 13.58 | 1.20 | 15.94 | 0.62 | 12.50 | 0.56 | 10.64 | 0.17 | 37.63 | 0.84 |
| Winner, SD | AAC A110 | 5.90 | 0.11 | 13.16 | 0.92 | 17.24 | 0.84 | 12.42 | 0.20 | 8.90 | 0.44 | 38.72 | 1.06 |
| Winner, SD | AAC A120 | 6.08 | 0.05 | 14.10 | 0.87 | 17.32 | 0.70 | 11.59 | 0.31 | 9.60 | 0.39 | 38.32 | 0.22 |
| Winner, SD | AGR044-312D | 6.36 | 0.10 | 16.33 | 1.06 | 19.13 | 0.45 | 9.81 | 0.16 | 9.19 | 0.27 | 37.87 | 0.82 |
| Tioga, ND | AAC A120 | 6.30 | 0.11 | 13.42 | 1.66 | 17.51 | 0.74 | 12.99 | 0.74 | 7.91 | 0.74 | 39.19 | 0.74 |
| Tioga, ND | AAC A110 | 6.23 | 0.05 | 10.49 | 1.76 | 15.89 | 0.74 | 13.51 | 0.74 | 8.80 | 0.74 | 39.77 | 0.74 |

TABLE 7-continued

Fatty acid profile of oil from grain harvested in North Dakota, Soiuth Dakota and Saskatchewan trials (2015)

| Site | Name | SATS | SD | C18.1 | SD | C18.2 | SD | C18.3 | SD | C20.1 | SD | C22.1 | SD |
|---|---|---|---|---|---|---|---|---|---|---|---|---|---|
| Tioga, ND | AGR044-3A22 | 6.30 | 0.05 | 11.66 | 1.46 | 17.00 | 0.74 | 12.74 | 0.74 | 9.49 | 0.74 | 38.08 | 0.74 |
| Winner, SD | AAC A120 | 6.29 | 0.25 | 14.68 | 0.91 | 19.36 | 0.74 | 11.17 | 0.74 | 8.32 | 0.74 | 36.76 | 0.74 |
| Winner, SD | AAC A110 | 6.27 | 0.02 | 13.39 | 3.05 | 18.44 | 0.74 | 11.77 | 0.74 | 8.66 | 0.74 | 37.92 | 0.74 |
| Winner, SD | AGR044-3A22 | 6.10 | 0.06 | 14.76 | 0.61 | 18.20 | 0.74 | 11.30 | 0.74 | 10.15 | 0.74 | 36.26 | 0.74 |

Example 4: AGR044-312D Yield Performance in Florida

Two small plot yield trials were carried out in Quincy, Fla. during the winter of 2014-2015 comprising 20 entries and had four replications per entry in a randomized complete block design. The sites differ in that one field contained no traces of residual Cadre Herbicide (a commonly used herbicide in the southeastern United States, but whose residue might be of concern to potential *carinata* growers), while the other was on a piece that did have carry over of residual Cadre herbicide from previous crops. Seed yield estimates were calculated from the least square means of replicated plots estimated in kg per hectare and/or bushel per acre. Least square mean values and their standard errors were compared via REML analysis (using student method of LS mean comparison) to determine whether differences were significant. Values that do not share a group letter are significantly different at P<0.05. All statistical analysis was performed using the JMP statistical analysis software (SAS).

As can be seen in Table 8, yields of AGR044-312D were significantly higher than checks in both the Cadre residue and no residue sites. The entry AGR044-312D Improved on A120 yields by 123% and A110 by 126% in the no residue site and likewise improved on A120 by 109% and A110 by 112% in cadre residue containing site. There did not appear to be a large difference between the site with Cadre residue and the no cadre site.

TABLE 8

AGR044-312D yields relative to checks in Quincy FL yield trials (Winter 2014-2015)

| Site | Variety | Yield (bu/ac) | Yield (kg/ha) | Std Error | Group |
|---|---|---|---|---|---|
| No Residue | AGR044-312D | 65.1 | 3647 | 112 | A |
| No Residue | AAC A120 | 53.1 | 2975 | 85 | CDE |
| No Residue | AAC A110 | 51.6 | 2888 | 177 | DEF |
| Cadre Residue | AGR044-312D | 70.7 | 3958 | 55 | — |
| Cadre Residue | AAC A120 | 64.6 | 3619 | 125 | — |
| Cadre Residue | AAC A110 | 62.9 | 3520 | 94 | — |

Example 5: AGR044-312D Agronomic Traits in Florida

Frost tolerance: In Florida, *carinata* is grown as a winter cover crop, seeded optimally in November. As such it is exposed to a period where frost is a persistant risk. Evidence has indicated that *carinata* is quite frost tolerant when exposed in early spring/late fall in its more northerly ranges and commercial varieties are assessed on their ability to recover after frost damage. Due to the fact that short periods of hard frost are an annual risk for *carinata*'s use as a winter grown crop, assessing frost tolerance characteristics in new varieties is an important breeding consideration. In the 2014-15 Florida yield trials, two consecutive nights reaching −9° C. provided good frost pressure to evaluate differences in yield trial entries. Frost tolerance was assessed on all plots at the two sites one, two, and three weeks following these hard frost events. This was done by determining the relative amount of damaged or dead plants in each plot, where 1 represents no damage and 10 represents all plants being killed. Table 9 illustrates post-frost ratings for AGR044-312D and the two check varieties, at each of the three time periods following the hard frost event. More freeze damage occurred at the No Residual site than the Cadre residual site. No major differences, positive or negative, were noted in these trials between 312D and the check varieties.

TABLE 9

Frost tolerance tolerance of AGR044-312D compared with checks in Quincy, FL, 2014-15

| No Residual - More freeze damage | | | | Cadre residual - Less freeze damage | | | |
|---|---|---|---|---|---|---|---|
| Name | 1 wk | 2 | 3 | Name | 1 wk | 2 | 3 |
| AAC A110 | 8 | 7 | 7 | AGR044-312D | 9 | 5 | 4 |
| AAC A120 | 9 | 8 | 7 | AAC A110 | 9 | 5 | 4 |
| AGR044-312D | 9 | 8 | 7 | AAC A120 | 9 | 6 | 5 |

Ratings: 1-10, indicating % damage. 1 = no damage; 10 = dead (ratings taken weekly after freeze event)

Maturity Ratings:

Days to maturity is an important factor in selection of new varieties. In Florida, as a winter cover crop, it is important that *carinata* matures and is harvested early enough to allow for timely seeding of the spring cash crops, such as peanuts, soybean, sesame, etc. Days to flowering is flowering is typically correlated with days to maturity, as earlier flowering and completion of flowering allows for earlier seed maturation. Accordingly, days to flowering and days to maturity were evaluated for AGR044-312D in relation to the check lines A110 and A120. At the no residue site, mean days to flowering occurred significantly earlier for the check lines than for AGR044-312D (by 2.5 days). Mean days to maturity for A110 occurred 1.8 days earlier than AGR044-312D while mean days to maturity for A120 occurred 3.3 days earlier than AGR044-312D, the latter difference being significant. It is not clear whether fertility would affect the maturity ratings. Thus, in the winter of 2014-15, 312D matured slightly later than the check varieties.

TABLE 10

Maturity ratings at the No Residue site in 2014-15 Quincy, FL yield trials

| Days to flowering | | | Days to maturity | | |
|---|---|---|---|---|---|
| Name | DTF | Group | Name | DTM | Group |
| AAC A120 | 109.8 | B | AAC A120 | 170.0 | A |
| AAC A110 | 109.8 | B | AAC A110 | 171.5 | ABC |
| AGR044-312D | 112.3 | CD | AGR044-312D | 173.3 | BCD |

Example 6: AGR044-312D Seed Quality Data from Quincy Florida (2014-2015)

Seed harvested from the 2014-2015 Florida yield trial sites were used for seed quality analysis using the same methodology as described in earlier examples Oil Content:

As can be seen in Table 11, the mean oil content of the AGR044-312D seed was slightly lower compared to those of the check-lines A110 and A120, however this difference was not statistically significant.

TABLE 11

Seed quality versus check lines for oil content of 312D in 2014-15 Quincy, FL yield testing - Least Square Mean of two sites

| Name | Oil % (LS Mean) | Std Error | Group |
|---|---|---|---|
| AAC A110 | 46.0 | 0.4 | ABC |
| AAC A120 | 45.2 | 0.5 | ABCD |
| AGR044-312D | 44.1 | 0.4 | BCDE |

GSL Content:

Similar to what was observed in the North Dakota, South Dakota and Saskatchewan trials, GSL content of AGR044-312D seed harvested from Florida trials (Table 12) showed a significant reduction relative to check lines A110 and A120 (in the order of a 40% reduction).

TABLE 12

Seed quality versus check lines for glucosinolate content of AGR044-312D in 2014-15 Quincy, FL yield testing - Least Square Mean of two sites

| Name | GSL (µmol/g) (LS Mean) | Std Error | Group |
|---|---|---|---|
| AAC A110 | 86.5 | 2.6 | G |
| AAC A120 | 87.3 | 3.1 | G |
| AGR044-3120 | 51.5 | 1.8 | A |

Seed Protein Content:

Table 13 compares the protein contents of AGR044-312D with those of check lines A110 and A120 in seed harvested from the 2014-2015 Florida field trials. At both sites in 2014-15 Quincy, Fla. yield testing, the AGR044-312D line had approximately 2% lower protein content on a whole seed basis than the check varieties.

TABLE 13

Seed protein levels of A110, A120 and AGR044-312D expressed as percentage of seed weight from 2014-15 Quincy, FL yield testing

| Sample | Name | Protein (%) | St Dev |
|---|---|---|---|
| Quincy, Cadre residue | AAC A110 | 29.3 | 0.9 |
| Quincy, Cadre residue | AAC A120 | 29.7 | 0.8 |
| Quincy, Cadre residue | AGR044-312D | 27.5 | 0.7 |
| Quincy, No herbicide residue | AAC A110 | 27.7 | 1.1 |
| Quincy, No herbicide residue | AAC A120 | 27.3 | 0.9 |
| Quincy, No herbicide residue | AGR044-312D | 25.0 | 1.1 |

Fatty Acid Profile:

Table 14 shows the fatty acid profile of AGR044-312D and check lines A110 and A120 from grain harvested from 2014-2015 Florida trials. Similar to that of the North Dakota, South Dakota and Saskatchewan trials, the VLCFA erucic acid (C22.1) proportion in AGR044-312D oil falls very close to those of the commercial check lines in these trials, and likewise levels of saturated fatty acid (SATS) of AGR044-312D oil are close to those of the check lines. The relative proportions of the other main fatty acid constituents of AGR044-312D oil do not deviate substantially from those of the check line counterparts. Thus, it is expected that the physical properties of AGR044-312D oil that are influenced by fatty acid composition should not differ greatly from those of the check lines.

TABLE 14

Fatty acid profiles of AGR044- 312D, A120 and A110 oil, as determined by NIR analysis, from 2014-15 Quincy, FL yield testing

| Sample | Name | SATS | sd | C18.1 | sd | C18.2 | sd | C18.3 | sd | C20.1 | sd | C22.1 | sd |
|---|---|---|---|---|---|---|---|---|---|---|---|---|---|
| Quincy, Cadre residue | AAC A110 | 6.3 | 0.1 | 11.1 | 1.0 | 15.5 | 0.7 | 13.8 | 0.4 | 8.2 | 0.3 | 39.6 | 1.0 |
| Quincy, Cadre residue | AAC A120 | 6.3 | 0.1 | 11.9 | 1.2 | 15.8 | 0.4 | 13.4 | 0.4 | 8.4 | 0.3 | 39.1 | 1.1 |
| Quincy, Cadre residue | AGR044-312D | 6.4 | 0.1 | 14.1 | 0.3 | 17.7 | 0.7 | 12.0 | 0.2 | 7.8 | 0.3 | 38.4 | 0.8 |
| Quincy, No herbicide residue | AAC A110 | 6.3 | 0.1 | 10.4 | 0.7 | 15.5 | 0.6 | 13.7 | 0.3 | 8.2 | 0.7 | 40.3 | 0.5 |
| Quincy, No herbicide residue | AAC A120 | 6.5 | 0.1 | 10.9 | 0.8 | 15.8 | 0.2 | 13.2 | 0.2 | 8.3 | 0.2 | 39.8 | 0.2 |

TABLE 14-continued

Fatty acid profiles of AGR044- 312D, A120 and A110 oil, as determined by NIR analysis, from 2014-15 Quincy, FL yield testing

| Sample | Name | SATS | sd | C18.1 | sd | C18.2 | sd | C18.3 | sd | C20.1 | sd | C22.1 | sd |
|---|---|---|---|---|---|---|---|---|---|---|---|---|---|
| Quincy, No herbicide residue | AGR044-312D | 6.4 | 0.1 | 12.8 | 0.7 | 16.5 | 0.2 | 12.0 | 0.3 | 8.7 | 0.1 | 40.4 | 1.0 |

Example 7: Preparation of DNA from *Brassica carinata* A110, A120, AGR044-312D and AGR044-3A22 Leaf Tissue Approximately 50-100 mg leaf tissues was sampled from *Brassica carinata* plants and placed into a sterile 1.5 ml microfuge tube on ice using forceps sterilized by dipping in 70% ethanol or 2% solution of sodium hypochlorite (NaClO) and wiping off between samples to avoid possible cross contamination. The tubes were then sealed with Parafilm and a fine-tipped forceps was used to make approximately 2-4 small holes in the Parafilm seal. The samples were then placed at −80° C. overnight (minimally greater than 12 hours).

After the −80° C. incubation, the samples were loaded directly from −80° C. into freeze drying apparatas and lyophilized for a minimum of 42 hours. Following the lyphilization, the parafilm seals were removed from the tubes and replaced with the tube lids. At this point samples could be stored at −20° C. for up to two weeks before processing for extraction of DNA.

To extract genomic DNA from the lyophilized samples two 3 mm glass beads (Sigma or any general suppliers) were placed into each tube. Tubes were then capped and loaded on a bead beater and processed twice for 30 s each time. Tubes were then centrifuged briefly to collect contents at the bottom and 500 μl of extraction buffer (2% CTAB, 100 mM Tris, pH 8, 20 mM EDTA, 1.4M NaCl; before use beta-mercaptoethanol was added at ratio of 4 μl/ml of extraction buffer) was added to each sample tube and mixed by inversion, ensuring that all the lyophilized powder was solubilized, then placed at 65° C. for 1 h. 500 μl of chloroform was then added and to each sample then content of the tubes was mixed by inversion for 5 minutes. Sample tubes were then centrifuged for 10 min at 13,000 RPM and then 400 μl of aqueous supernatant phase was transferred to new tubes containing 250 μl of isopropanol, mixed by inversion and incubated at room temperature for 10 minutes to overnight. DNA pellets were collected by centrifugation at 13,000 rpm for 15 min. Pellets were washed 2× by addition of 250 μl of 70% followed by centrifugation at 13000 RPM for 1 min and removal of supernatant. After the completion of the second wash, the tubes were briefly centrifuged to collect any residual liquid, and the last drops of wash was removed with a micropipettor. The DNA pellets were dried at room temperature for 5 minutes, and then resuspended in 50 μl 0.1×TE (for PCR) or 1×TE (for other downstream work) containing 1 μl of RNase A (10 mg/ml). Genomic DNA (gDNA) was quantified by picogreen fluorescence using the Quanti-IT DS DNA assay kit (Invitrogen) according to the manufacturers instructions and sample concentrations were normalized to 20 ng/μl.

Example 8: GBS Library Generation and QC from DNA from *Brassica carinata* A110, A120, AGR044-312D and AGR044-3A22

GBS libraries were generated essentially as described (Poland et al. 2012). Briefly, 10 μl of DNA (20 ng/μl) was double digested with restriction enzymes Pstl (Pstl-HF, NEB, Cat.# R3140) and Mspl (NEB, Cat.# R0106) by incubating at 37° C. for 2 hrs, then 65° C. for 20 min. Digested DNA was ligated to adapters by adding 5 μl of Adapters (0.02 μM Adapter 1=0.1 pmol, 3 μM Adapter 2=15 pmol) and 15 μl ligation mix (2 μl NEB Buffer 4, 4 μl ATP (10 mM), 0.5 μl T4 DNA ligase (200 U)), and 8.5 μl $H_2O$. The reaction was incubated at 22° C. for 2 h, and then 65° C. for 20 min. Five μl from each sample ligation was pooled into a single tube and cleaned on a Qiagen column (QIAquick PCR Purification Kit (Qiagen, Cat#: 28106)). Eight PCR reactions were made for each library: 10 μl DNA (digested library), 5 μl Taq 5× Master Mix (NEB, Cat# M0285S), and 8 μl $H_2O$. PCR was run following this program: 95° C., 30 s.; 16 cycles of 95° C., 30 s, 62° C., 30 s, and 68° C. for 30 s; followed by extension at 72° C. for 5 min. The 8 PCR reactions were pooled and cleaned using QIAquick PCR Purification Kit following the manufacturer's directions and resuspended in 30 μl 1× TE buffer (pH 8.0) with addition of 1 μl of RNase A (10 mg/μl). Prior to sequencing the GBS library was checked for quality on Agilent 2100 Bioanalyzer using the Agilent DNA 1000 Kit (Cat: 5067-1504) to ensure that a majority DNA fragments ranged from 150-250 bp in size.

6. DEPOSITS

Applicant has made a deposit of at least 2500 seeds of *Brassica carinata* Cultivar AGR044-312D with the American Type Culture Collection (ATCC), Manassas, Va. 20110 USA, ATCC Deposit No. PTA-123015. The seeds deposited with the ATCC on Apr. 12, 2016 were taken from the deposit maintained by Agrisoma Biosciences Inc. since prior to the filing data of this application. This deposit of the *Brassica carinata* Cultivar AGR044-312D will be maintained in the ATCC depository, which is a public depository, for a period of 30 years, or 5 years after the most recent request, or for the effective life of the patent, whichever is longer, and will be replaced if it becomes nonviable during that period. Additionally, Applicant has satisfied all the requirements of 37 C.F.R. §§ 1.801-1.809, including providing an indication of the viability of the sample. Applicant imposes no restrictions on the availability of the deposited material from the ATCC; however, Applicant has no authority to waive any restrictions imposed by law on the transfer of biological material or its transportation in commerce. Applicant does not waive any infringement of his rights granted under this patent or under the Plant Variety Protection Act (7 USC 2321 et seq.).

Applicant has made a deposit of at least 2500 seeds of *Brassica carinata* Cultivar AGR044-3A22 with the American Type Culture Collection (ATCC), Manassas, Va. 20110 USA, ATCC Deposit No. PTA-123014. The seeds deposited with the ATCC on Apr. 12, 2016 were taken from the deposit maintained by Agrisoma Biosciences Inc. since prior to the filing data of this application. This deposit of the *Brassica carinata* Cultivar AGR044-3A22 will be maintained in the ATCC depository, which is a public depository, for a period of 30 years, or 5 years after the most recent request, or for the effective life of the patent, whichever is longer, and will be replaced if it becomes nonviable during that period. Additionally, Applicant has satisfied all the requirements of 37 C.F.R. §§ 1.801-1.809, including providing an indication of the viability of the sample. Applicant imposes no restrictions on the availability of the deposited material from the ATCC; however, Applicant has no authority to waive any restrictions imposed by law on the transfer of biological material or its transportation in commerce. Applicant does not waive any infringement of his rights granted under this patent or under the Plant Variety Protection Act (7 USC 2321 et seq.).

The foregoing invention has been described in detail by way of illustration and example for purposes of exemplification. However, it will be apparent that changes and modifications such as single gene modifications and mutations, somaclonal variants, variant individuals selected from populations of the plants of the instant cultivar, and the like, likewise are considered to be within the scope of the present invention.

7. REFERENCES

Alcántara, C., et al. (2011). "Management of cruciferous cover crops by mowing for soil and water conservation in southern Spain." Agricultural Water Management 98(6): 1071-1080.

Babic V, Datla R S, Scoles G J, Keller W A (1997) Development of an efficient *Agrobacterium* mediated transformation system for *Brassica carinata*. Plant Cell Rep 17:183-188

Barro, F. and A. Martin 1999. "Response of different genotypes of *Brassica carinata* to microspore culture." Plant Breeding 118(1): 79-81.

Bevan, M. (1984) Binary *Agrobacterium* vectors for plant transformation. Nucl. Acids Res. 12, 8711-8721.

Blackshaw, R., et al. (2011). "Alternative oilseed crops for biodiesel feedstock on the Canadian prairies." Canadian Journal of Plant Science 91(5): 889-896.

Bouaid, A., et al. (2005). "Pilot plant studies of biodiesel production using *Brassica carinata* as raw material." Catalysis Today 106(1-4): 193-196.

Cardone, M., et al. (2002). "*Brassica carinata* as an alternative oil crop for the production of biodiesel in Italy: engine performance and regulated and unregulated exhaust emissions." Environ Sci Technol 36(21): 4656-4662.

Cardone, M., et al. (2003). "*Brassica carinata* as an alternative oil crop for the production of biodiesel in Italy: agronomic evaluation, fuel production by transesterification and characterization." Biomass and Bioenergy 25(6): 623-636.

Chan T W, Chishty W A, Canteenwalla P, Buote D, Davison C R. (2015) Characterization of Emissions From the Use of Alternative Aviation Fuels. ASME. J. Eng. Gas Turbines Power. 138(1):011506-011506-9.

Cheng, B., et al. (2009). "Towards the production of high levels of eicosapentaenoic acid in transgenic plants: the effects of different host species, genes and promoters." Transgenic Research 19(2): 221-229.

Datla, R. S., et al. (1992). "Modified binary plant transformation vectors with the wild-type gene encoding NPTII." Gene 122(2): 383-384.

Drenth, A. C., et al. (2014). "Compression ignition engine performance and emission evaluation of industrial oilseed biofuel feedstocks camelina, *carinata*, and pennycress across three fuel pathways." Fuel 136(0): 143-155.

Drenth, A. C., et al. (2015). "Fuel property quantification of triglyceride blends with an emphasis on industrial oilseeds camelina, *carinata*, and pennycress." Fuel 153: 19-30.

Fromm, M., et al. (1985). "Expression of genes transferred into monocot and dicot plant cells by electroporation." Proceedings of the National Academy of Sciences of the United States of America 82(17): 5824-5828.

Gasol, C. M., et al. (2009). "Feasibility assessment of poplar bioenergy systems in the Southern Europe." Renewable and Sustainable Energy Reviews 13(4): 801-812.

Gasol, C., et al. (2007). "Life cycle assessment of a *Brassica carinata* bioenergy cropping system in southern Europe." Biomass and Bioenergy 31(8): 543-555.

Gesch, R. W., et al. (2015). "Comparison of several *Brassica* species in the north central U.S. for potential jet fuel feedstock." Industrial Crops and Products 75b: 2-7.

Getinet, A, Rakow, G. and Downey, R. K. 1996. Agronomic performance and seed quality of Ethiopian mustard in Saskatchewan. Can. J. Plant Sci. 76: 387-392.

Getinet, A., Rakow, G. and Downey, R. K. 1987. Seed coat color inheritance in *Brassica carinata* A. Braun, Cultivar S-67. Plant Breed. 99: 80-82

Gleba, Y., et al. (2004). "Engineering viral expression vectors for plants: the 'full virus' and the 'deconstructed virus' strategies." Curr Opin Plant Biol 7(2): 182-188.

Impallomeni, G., et al. (2011). "Synthesis and characterization of poly(3-hydroxyalkanoates) from *Brassica carinata* oil with high content of erucic acid and from very long chain fatty acids." International Journal of Biological Macromolecules 48(1): 137-145.

Jadhav, A., et al. (2005). "Production of 22:2Δ5413 and 20:1Δ5 in *Brassica carinata* and soybean breeding lines via introduction of Limnanthes genes." Molecular Breeding 15(2): 157-167.

Johnson, C. M., et al. (1989). "Direct gene transfer via polyethylene glycol." Methods in Cell Science 12(4): 127-133.

Lazzarini et al (2010) Use of seed flour as soil pesticide U.S. Pat. No. 7,749,549 B2

Márquez-Lema, A., et al. (2007). Genetic study of very high glucosinolate content in Ethiopian mustard seeds. Proceedings 12th International Rapeseed Congress, Wuhan, China, GCIRC.

Márquez-Lema, A., et al. (2008). "Development and characterisation of a *Brassica carinata* inbred line incorporating genes for low glucosinolate content from *B. juncea*." Euphytica 164(2): 365-375.

Miki, B. L., H. Labbe, J. Hattori, T. Ouellet, G. Sunohara, P. J. Charest, and V. N. Iyer, 1990: Transformation of *Brassica napus* canola cultivars with *Arabidopsis thaliana* acetohydroxyacid synthase genes and analysis of herbicide resistance. Theor. Appl. Genet. 80, 449-458

Mourato, M. P., et al. (2015). "Effect of Heavy Metals in Plants of the Genus *Brassica*." Int J Mol Sci 16(8): 17975-17998.

Nagaharu, U. 1935. "Genome analysis in *Brassica* with special reference to the experimental formation of *B. napus* and peculiar mode of fertilization." Japanese Journal of Botany 7: 389-452.

Newson, W. R., et al. (2014). "Effect of additives on the tensile performance and protein solubility of industrial oilseed residual based plastics." J Agric Food Chem 62(28): 6707-6715.

Ogura H. (1968) Studies on the new male-sterility in Japanese radish, with special reference to the utilization of this sterility towards the practical raising of hybrid seeds. Mem. Fac. Agric. Kagoshima Univ. 6: 39-78

Pan, X., et al. (2012). "The effect of cultivar, seeding rate and applied nitrogen on *Brassica carinata* seed yield and quality in contrasting environments." Canadian Journal of Plant Science 92(5): 961-971.

Pane, C., et al. (2013). "Screening of plant-derived antifungal substances useful for the control of seedborne pathogens." Archives of Phytopathology and Plant Protection 46(13): 1533-1539.

Petolino, J. F., et al. (2010). "Zinc finger nuclease-mediated transgene deletion." Plant Molecular Biology 73(6): 617-628.

Poland, J. A., et al. (2012). "Development of High-Density Genetic Maps for Barley and Wheat Using a Novel Two-Enzyme Genotyping-by-Sequencing Approach." PLoS ONE 7(2): e32253.

Prakash, S, Wu, X, Bhat S. R. 2012. History, evolution and domestication of *Brassica* crops. Plant Breed Rev. 35:19-84.

Rahman, M. and Tahir, M. 2010. Inheritance of seed coat colorof Ethiopian mustard (*Brassica carinata* A. Braun). Can. J Plant Sci. 90: 279-281.

Rothstein, S. J.; Lahners, K. N.; Lotstein, R. L., et al. (1987) Promoter cassettes, antibiotic-resistance genes, and vectors for plant transformation. Gene 53:153-161.

Sauer, N. J., et al. (2016). "Oligonucleotide-mediated genome editing provides precision and function to engineered nucleases and antibiotics in plants." Plant Physiol.

Schulmeister, T. M. et al (2015) Evaluation of *Brassica Carinata* as a Protein Supplement for Growing Beef Heifers. 2015 Florida Beef Research Report 137-142

Tang, G. and G. Galili (2004). "Using RNAi to improve plant nutritional value: from mechanism to application." Trends Biotechnol 22(9): 463-469.

Taylor, D. C., et al. (2010). "*Brassica carinata*—a new molecular farming platform for delivering bio-industrial oil feedstocks: case studies of genetic modifications to improve very long-chain fatty acid and oil content in seeds." Biofuels, Bioproducts and Biorefining 4(5): 538-561.

Thompson, C, N. R., Movva, R. Tizard, R. Crameri, J. E. Davies, M. Lauwereys, and J. Botterman, 1987: Characterization of the herbicide-resistance gene har from *Streptomyces hygroscopicus*. EMBO J. 6, 2519-2523.

Warwick, S. I., Francis, A. and Gugel, R. K. 2009. Guide to wild germplasm *Brassica* and allied crops (Tribe Brassiceae, Brassicaceae). 3rd ed. Agriculture and Agri-Food Canada Research Branch Publication, ECORC, Ottawa. [Online] Available: http://www.brassica.info/info/publications/guide-wild-germplasm.php [2013 Jul. 10].

Wohlleben, W., W. Arnold, W. Broer, D. Hillemann, E. Strauch, and A. Puhler, 1988: Nucleotide sequence of the phosphotrinocin Nacetyl transferase gene from *Streptomyces viridochromogenes* Tu494 and its expression in *Nicotiana tahacum*. Gene 70, 25-37

Woo, J. W., et al. (2015). "DNA-free genome editing in plants with preassembled CRISPR-Cas9 ribonucleoproteins." Nat Biotechnol 33(11): 1162-1164.

Zanetti, F., et al. (2006). "Can We "Cultivate" Erucic Acid in Southern Europe?" Ital. J. Agron./Riv. Agron. 1: 3-10.

Zanetti, F., et al. 2013. "Challenges and opportunities for new industrial oilseed crops in EU-27: A review." Industrial Crops and Products 50: 580-595.

The invention claimed is:

1. A seed of *Brassica carinata* cultivar designated AGR044-312D, wherein a representative sample of the seed has been deposited under ATCC Accession number PTA-123015.

2. A plant of *Brassica carinata* cultivar AGR044-312D, or a part thereof, produced from the seed of claim 1.

3. A *Brassica carinata* plant, or parts thereof, having essentially all of the physiological and morphological characteristics of the plant of claim 2 when grown in the same location under the same environmental conditions.

4. A tissue culture of protoplasts or regenerable cells of the plant, or part thereof, of claim 2.

5. A method for producing *Brassica carinata* seed comprising crossing *Brassica carinata* plants and harvesting the resulting *Brassica carinata* seed, wherein at least one *Brassica carinata* plant is the plant of claim 2.

6. A method for producing a first generation (F1) hybrid *Brassica carinata* seed comprising crossing the plant of claim 2, with a different *Brassica carinata* plant and harvesting the resultant F1 hybrid carinata seed, and wherein the plant of claim 2 is either a female parent or a male parent.

7. A method of producing a *Brassica carinata* variety produced from the plant of claim 2, wherein the *Brassica carinata* variety comprises a desired trait, the method comprising the steps of:
  (a) crossing a plant of cultivar AGR044-312D with another *Brassica carinata* variety comprising the desired trait;
  (b) growing the resultant F1 hybrid seed and selecting one or more progeny plants that have the desired trait;
  (c) backcrossing the selected progeny plants that have the desired trait with plants of cultivar AGR044-312D to produce backcross progeny seed; and
  (d) growing the resultant backcross progeny seed and selecting backcross progeny plants that have the desired trait to produce the *Brassica carinata* variety produced from cultivar AGR044-312D.

8. The method of claim 7, wherein steps (c) and (d) are repeated until the *Brassica carinata* variety produced from cultivar AGR044-312D has the desired trait and essentially all of the physiological and morphological characteristics of cultivar AGR044-312D when grown in the same location under the same environmental conditions.

9. The method of claim 7, wherein the desired trait is selected from the group consisting of male sterility, disease resistance, fungal resistance, pest resistance, herbicide tolerance, abiotic stress tolerance, and altered metabolism.

10. A plant, or part thereof, or seed thereof, produced by the method of claim 5.

* * * * *